United States Patent
Masel et al.

(10) Patent No.: US 8,123,834 B2
(45) Date of Patent: Feb. 28, 2012

(54) HIGH GAIN SELECTIVE METAL ORGANIC FRAMEWORK PRECONCENTRATORS

(75) Inventors: Richard I. Masel, Champaign, IL (US); Zheng Ni, Urbana, IL (US); Mark A. Shannon, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 1545 days.

(21) Appl. No.: 11/539,405

(22) Filed: Oct. 6, 2006

(65) Prior Publication Data

US 2010/0132547 A1    Jun. 3, 2010

Related U.S. Application Data

(60) Provisional application No. 60/724,313, filed on Oct. 6, 2005, provisional application No. 60/791,988, filed on Apr. 14, 2006, provisional application No. 60/828,266, filed on Oct. 5, 2006.

(51) Int. Cl.
*B01D 53/02* (2006.01)

(52) U.S. Cl. .................. 95/90; 95/82; 95/141; 96/108; 96/154; 73/23.41

(58) Field of Classification Search .............. 95/85, 88, 95/89, 90, 141; 96/105, 108, 154; 73/23.39, 73/23.41, 23.42; 423/592.1–643
See application file for complete search history.

(56) References Cited

U.S. PATENT DOCUMENTS

| | | | |
|---|---|---|---|
| 2,901,623 A | 8/1959 | Wouters | |
| 3,168,823 A | 2/1965 | Reinecke et al. | |
| 3,345,858 A | 10/1967 | Fenske | |
| 3,357,232 A | 12/1967 | Lauer | |
| 3,568,411 A | 3/1971 | Dravnieks et al. | |
| 3,585,863 A | 6/1971 | Hrdina | |
| 3,675,466 A | 7/1972 | Linenberg | |
| 3,733,908 A | 5/1973 | Linenberg | |
| 3,769,837 A | 11/1973 | Kraus | |
| 3,797,318 A | 3/1974 | Palm | |
| 3,807,217 A | 4/1974 | Wilkins et al. | |
| 3,897,679 A | 8/1975 | Guild | |
| 3,923,461 A | 12/1975 | Barden | |

(Continued)

OTHER PUBLICATIONS

Zheng NI, et al., "Rapid Production of Metal-Organic Frameworks via Microwave-Assisted Solvothermal Synthesis," J. Am. Chem. Soc.

(Continued)

*Primary Examiner* — Robert Clemente
(74) *Attorney, Agent, or Firm* — Kilpatrick Townsend & Stockton LLP

(57) ABSTRACT

Novel metal organic framework (MOF) molecules and methods of synthesizing them are described. MOFs are organometallic crystalline structures that have high sorption capacity due to high surface area, tailorable selectivity, an inert nature, and thermal stability at high temperatures. MOFs may be used as sorbents in preconcentrators for analytical devices to provide orders of magnitude of improved sensitivity in analyte detection. MOFs are also useful as sorbents in new compact and portable micropreconcentrator designs such as a modified purge and trap system and a multi-valve microelectromechanical system (MEMS) to achieve high gain in analyte detection. Further, MOFs may be used as coatings for novel microstructure arrays in micropreconcentrators where the microstructures are designed to increase the surface area to volume ratio inside the micropreconcentrator while minimizing the pressure drop across the micropreconcentrator.

24 Claims, 27 Drawing Sheets

U.S. PATENT DOCUMENTS

| | | |
|---|---|---|
| 3,925,022 A | 12/1975 | Showalter et al. |
| 3,950,980 A | 4/1976 | Braun et al. |
| 3,985,017 A | 10/1976 | Goldsmith |
| 4,040,085 A | 8/1977 | Jouanny |
| 4,040,805 A | 8/1977 | Nelms et al. |
| 4,084,440 A | 4/1978 | Carpenter et al. |
| 4,128,008 A | 12/1978 | Linenberg |
| 4,129,424 A | 12/1978 | Armond |
| 4,180,389 A | 12/1979 | Paul |
| 4,235,097 A | 11/1980 | Kring et al. |
| 4,293,316 A | 10/1981 | Block |
| 4,301,114 A | 11/1981 | Rounbehler et al. |
| 4,399,688 A | 8/1983 | Dennis |
| 4,451,816 A | 5/1984 | Ball |
| 4,498,850 A | 2/1985 | Perlov et al. |
| 4,541,268 A | 9/1985 | Odernheimer |
| 4,585,209 A | 4/1986 | Aine et al. |
| 4,599,095 A | 7/1986 | Barnes et al. |
| 4,628,576 A | 12/1986 | Giachino et al. |
| 4,647,013 A | 3/1987 | Giachino et al. |
| 4,698,071 A | 10/1987 | Elias |
| 4,701,306 A | 10/1987 | Lawrence et al. |
| 4,713,091 A | 12/1987 | Govind |
| 4,735,691 A | 4/1988 | Green et al. |
| 4,759,210 A | 7/1988 | Wohltjen |
| 4,778,666 A | 10/1988 | Chu et al. |
| 4,805,441 A | 2/1989 | Sides et al. |
| 4,819,477 A | 4/1989 | Fisher et al. |
| 4,821,999 A | 4/1989 | Ohtaka |
| 4,826,131 A | 5/1989 | Mikkor |
| 4,885,830 A | 12/1989 | Ohtaka |
| 4,895,500 A | 1/1990 | Hok |
| 4,915,051 A | 4/1990 | Martinek |
| 4,915,843 A | 4/1990 | Taniguchi et al. |
| 4,977,095 A | 12/1990 | Zaromb |
| 4,997,676 A | 3/1991 | Lefebvre |
| 5,014,541 A | 5/1991 | Sides et al. |
| 5,069,419 A | 12/1991 | Jerman |
| 5,082,242 A | 1/1992 | Bonne et al. |
| 5,083,019 A | 1/1992 | Spangler |
| 5,092,155 A | 3/1992 | Rounbehler et al. |
| 5,092,217 A | 3/1992 | Achter et al. |
| 5,092,218 A | 3/1992 | Fine et al. |
| 5,110,551 A | 5/1992 | Michal |
| 5,123,276 A | 6/1992 | Hartman et al. |
| 5,142,143 A | 8/1992 | Fite et al. |
| 5,162,652 A | 11/1992 | Cohen et al. |
| 5,173,264 A | 12/1992 | Zaromb et al. |
| 5,176,358 A | 1/1993 | Bonne et al. |
| 5,180,623 A | 1/1993 | Ohnstein |
| 5,216,273 A | 6/1993 | Doering et al. |
| 5,224,972 A | 7/1993 | Frye et al. |
| 5,288,310 A | 2/1994 | Peters et al. |
| 5,294,418 A | 3/1994 | Ramprasad et al. |
| 5,322,258 A | 6/1994 | Bosch et al. |
| 5,323,999 A | 6/1994 | Bonne et al. |
| 5,328,851 A | 7/1994 | Zaromb |
| 5,395,589 A | 3/1995 | Nacson |
| 5,417,235 A | 5/1995 | Wise et al. |
| 5,441,597 A | 8/1995 | Bonne et al. |
| 5,465,607 A | 11/1995 | Corrigan et al. |
| 5,468,851 A | 11/1995 | Seeman et al. |
| 5,481,110 A | 1/1996 | Krishnaswamy et al. |
| 5,482,677 A | 1/1996 | Yao et al. |
| 5,522,918 A | 6/1996 | Shiramizu |
| 5,532,129 A | 7/1996 | Hellar |
| 5,551,278 A | 9/1996 | Rounbehler et al. |
| 5,585,575 A | 12/1996 | Corrigan et al. |
| 5,589,396 A | 12/1996 | Frye et al. |
| 5,619,177 A | 4/1997 | Johnson et al. |
| 5,648,508 A | 7/1997 | Yaghi |
| 5,720,798 A | 2/1998 | Nickerson et al. |
| 5,753,832 A | 5/1998 | Bromberg et al. |
| 5,763,360 A | 6/1998 | Gundel et al. |
| 5,795,368 A | 8/1998 | Wright et al. |
| 5,830,427 A | 11/1998 | Bedard et al. |
| 5,836,750 A | 11/1998 | Cabuz |
| 5,854,431 A | 12/1998 | Linker et al. |
| 5,876,830 A | 3/1999 | Michl et al. |
| 5,899,218 A | 5/1999 | Dugan |
| 5,941,501 A | 8/1999 | Biegelsen et al. |
| 5,970,804 A | 10/1999 | Robbat, Jr. |
| 6,000,676 A | 12/1999 | Zengerle et al. |
| 6,085,601 A | 7/2000 | Linker et al. |
| 6,098,661 A | 8/2000 | Yim et al. |
| 6,110,247 A | 8/2000 | Birmingham et al. |
| 6,126,140 A | 10/2000 | Johnson et al. |
| 6,129,331 A | 10/2000 | Henning et al. |
| 6,165,254 A | 12/2000 | Kawakami et al. |
| 6,171,378 B1 | 1/2001 | Manginell et al. |
| 6,182,941 B1 | 2/2001 | Scheurenbrand et al. |
| 6,187,412 B1 | 2/2001 | Armacost et al. |
| 6,215,221 B1 | 4/2001 | Cabuz et al. |
| 6,223,584 B1 | 5/2001 | Mustacich et al. |
| 6,251,260 B1 | 6/2001 | Heller et al. |
| 6,345,545 B1 | 2/2002 | Linker et al. |
| 6,355,793 B1 | 3/2002 | Lin |
| 6,372,932 B1 | 4/2002 | Kepert et al. |
| 6,384,253 B1 | 5/2002 | Khan |
| 6,455,003 B1 | 9/2002 | Anvia et al. |
| 6,470,904 B1 | 10/2002 | Tai et al. |
| 6,481,263 B1 * | 11/2002 | Haley et al. .................. 73/23.41 |
| 6,491,740 B1 | 12/2002 | Wang et al. |
| 6,517,610 B1 | 2/2003 | de la Houssaye |
| 6,523,393 B1 | 2/2003 | Linker et al. |
| 6,527,835 B1 | 3/2003 | Manginell et al. |
| 6,557,820 B2 | 5/2003 | Wetzel et al. |
| 6,568,286 B1 | 5/2003 | Cabuz |
| 6,604,406 B1 | 8/2003 | Linker et al. |
| 6,607,700 B1 | 8/2003 | Apte et al. |
| 6,610,125 B2 | 8/2003 | Tripp et al. |
| 6,626,416 B2 | 9/2003 | Sharma et al. |
| 6,626,417 B2 | 9/2003 | Winger et al. |
| 6,649,129 B1 * | 11/2003 | Neal ................................ 422/89 |
| 6,656,738 B1 | 12/2003 | Vogel et al. |
| 6,663,697 B1 * | 12/2003 | Kottenstette et al. ........... 96/101 |
| 6,666,907 B1 * | 12/2003 | Manginell et al. ................. 95/87 |
| 6,685,841 B2 | 2/2004 | Lopez et al. |
| 6,706,091 B1 * | 3/2004 | Robinson et al. ................. 95/87 |
| 6,719,828 B1 | 4/2004 | Lovell et al. |
| 6,749,826 B2 | 6/2004 | Tillotson et al. |
| 6,772,513 B1 | 8/2004 | Frye-Mason et al. |
| 6,773,674 B2 | 8/2004 | Bannister et al. |
| 6,793,753 B2 * | 9/2004 | Unger et al. ................... 156/155 |
| 6,814,781 B2 | 11/2004 | Tonkovich et al. |
| 6,830,229 B2 | 12/2004 | Wetzel et al. |
| 6,834,671 B2 | 12/2004 | Cotte et al. |
| 6,837,476 B2 | 1/2005 | Cabuz et al. |
| 6,838,640 B2 * | 1/2005 | Wise et al. ..................... 219/209 |
| 6,840,120 B2 | 1/2005 | Sakairi et al. |
| 6,848,325 B2 | 2/2005 | Parmeter et al. |
| 6,875,257 B2 | 4/2005 | Rodgers |
| 6,893,564 B2 | 5/2005 | Mueller et al. |
| 6,902,701 B1 | 6/2005 | Hughes et al. |
| 6,910,394 B2 | 6/2005 | Kriel |
| 6,913,697 B2 | 7/2005 | Lopez et al. |
| 6,914,220 B2 | 7/2005 | Tian et al. |
| 6,929,679 B2 | 8/2005 | Muller et al. |
| 6,930,193 B2 | 8/2005 | Yaghi et al. |
| RE38,797 E | 9/2005 | Linker et al. |
| 6,965,026 B2 | 11/2005 | Zaworotko et al. |
| 6,967,103 B2 | 11/2005 | Schwartz et al. |
| 6,967,193 B1 | 11/2005 | Dang et al. |
| 6,968,862 B2 | 11/2005 | Cabuz et al. |
| 6,978,657 B1 | 12/2005 | Baumann et al. |
| 6,984,524 B2 | 1/2006 | Nguyen et al. |
| 6,986,365 B2 | 1/2006 | Henning et al. |
| 6,986,500 B2 | 1/2006 | Giousouf et al. |
| 6,989,044 B2 | 1/2006 | Zhang et al. |
| 7,000,452 B2 | 2/2006 | Bonne et al. |
| 7,008,193 B2 * | 3/2006 | Najafi et al. .................... 417/244 |
| 7,014,165 B2 | 3/2006 | Ji et al. |
| 7,052,677 B1 | 5/2006 | Raptis et al. |
| 7,147,695 B2 * | 12/2006 | Mitra ............................... 96/101 |
| 7,654,129 B2 * | 2/2010 | Bonne et al. .................. 73/23.21 |
| 7,695,681 B2 * | 4/2010 | Wang et al. ...................... 422/89 |
| 2002/0175302 A1 | 11/2002 | Wetzel |

| | | | |
|---|---|---|---|
| 2003/0004364 A1* | 1/2003 | Yaghi et al. | 556/46 |
| 2003/0078311 A1 | 4/2003 | Muller et al. | |
| 2003/0146401 A1 | 8/2003 | Wetzel | |
| 2003/0148165 A1 | 8/2003 | Muller et al. | |
| 2003/0222023 A1* | 12/2003 | Mueller et al. | 210/656 |
| 2003/0231967 A1* | 12/2003 | Najafi et al. | 417/322 |
| 2003/0234376 A1 | 12/2003 | Cabuz et al. | |
| 2004/0097724 A1 | 5/2004 | Muller et al. | |
| 2004/0137300 A1 | 7/2004 | Gemmen et al. | |
| 2004/0191125 A1 | 9/2004 | Kellogg et al. | |
| 2004/0225134 A1* | 11/2004 | Yaghi et al. | 549/211 |
| 2004/0249189 A1 | 12/2004 | Mueller et al. | |
| 2004/0265670 A1 | 12/2004 | Muller et al. | |
| 2005/0004404 A1 | 1/2005 | Muller et al. | |
| 2005/0067029 A1 | 3/2005 | Henning | |
| 2005/0098435 A1 | 5/2005 | Jacobson et al. | |
| 2005/0101027 A1 | 5/2005 | Haas | |
| 2005/0124819 A1 | 6/2005 | Yaghi et al. | |
| 2005/0154222 A1 | 7/2005 | Muller et al. | |
| 2005/0164870 A1* | 7/2005 | Shan et al. | 502/64 |
| 2005/0192175 A1 | 9/2005 | Yaghi et al. | |
| 2006/0037477 A1 | 2/2006 | Lopez et al. | |
| 2006/0049101 A1* | 3/2006 | Suib et al. | 210/500.21 |
| 2006/0057057 A1 | 3/2006 | Muller et al. | |
| 2006/0099398 A1* | 5/2006 | Hesse et al. | 428/312.2 |
| 2006/0200044 A1 | 9/2006 | Freeman et al. | |
| 2006/0252641 A1* | 11/2006 | Yaghi et al. | 502/401 |
| 2007/0023719 A1 | 2/2007 | Masel et al. | |
| 2007/0074717 A1* | 4/2007 | Law et al. | 126/618 |
| 2008/0149869 A1 | 6/2008 | Shannon et al. | |
| 2009/0131643 A1 | 5/2009 | Zheng et al. | |
| 2009/0178563 A1 | 7/2009 | Masel et al. | |
| 2009/0211452 A1 | 8/2009 | Masel et al. | |
| 2010/0075123 A1 | 3/2010 | Masel et al. | |

OTHER PUBLICATIONS

Jay W. Grate, et al., "Progressive Thermal Desorption of Vapor Mixtures from a Preconcentrator with a Porous Metal Foam Internal Architecture and Variable Thermal Ramp Rates," pp. 1867-1875.
R. W. Jotham, et al., "Antiferromagnetism in transition-metal complexes. Part IV. Low-lying excited states of binuclear copper(II) carboxylate complexes," J. C. S. Dalton, pp. 428-438.
K. Tamada, et al., "The steady two-dimensional flow of viscous fluid at low Reynolds numbers passing through an infinite row of equal parallel circular cylinders," Quart. J. Mech. Appl. Math., 10, 1957, 425-432.
H. Hasimoto, "On the periodic fundamental solutions of the Stokes equations and their application to viscous flow past a cubic array of spheres," J. Fluid Mech., 5, 1959, pp. 317-328.
Michinobu Kato, et al., "Copper (II) complexes with subnormal magnetic moments," Richard Chemistry Lab, Tulane University, New Orleans Louisiana, Dec. 20, 1963 pp. 99-128.
Joseph B. Keller, "Viscous flow through a grating or lattice of cylinders," J. Fluid Mech. 18, 1964, pp. 94-96.
Wolfgang Micklitz, et al., Heptadecanuclear mixed metal iron oxohydroxo complexes, $[Fe_{16}MO_{10}(OH)_{10}(O_2CPh)_{20}]$ M=Mn or Co, structurally comprised of two fragments derived from $[Fe_{11}O_6(OH)_6(O_2CPh)_{15}]$ Journal American Chemical Society (1989) vol. 111, pp. 6856-6858.
Bernard F. Hoskins, et al., "Infinite polymeric frameworks consisting of three dimensionally linked rod-like segments," Journal of the American Chemical Society, vol. 111, No. 15, (1989) pp. 5962-5964.
Sergiu M. Gorun, et al., "Magnetostructural correlations in magnetically coupled (µ-Oxo)diiron(III) complexes," Inorganic Chemistry, 1991, 30(7) pp. 1625-1630.
Vinod S. Nair, et al., "Iron Oxo aggregation: $Fe_3$ to $Fe_6$. Synthesis, structure, and magnetic properties of the hexanuclear dication $[Fe_6(\mu_4-O)_2 (\mu_2-OMe)_8(OMe)_4(tren)_2]^{2+}$, a soluble, crystalline model of iron Oxo hydroxo nanoparticles, the core of ferritin and rust formation," Inorganic Chemistry (1992) vol. 31, pp. 4048- 4050.
Steven C. Shoner, et al., "Neutral catecholate derivatives of manganese and iron: Synthesis and characterization of the metal-oxygen cubane-like species $M_4(DBCat)_4(py)_6$ (M=Mn, Fe), the trinuclear complex $Mn_3(DBCat)_4(py)_4$ and the dimers $M_2(DBCat)_2(py)_n$ (M=Mn, n=6; M=Fe, n=4,6)," Inorganic Chemistry (1992) 31, pp. 1001-1010.

C.T. Kresge, et al., "Ordered mesoporous molecular sieves synthesized by a liquid-crystal template mechanism," Nature, vol. 359, Oct. 22, 1992, pp. 710-712.
Kingsley L. Taft, et al., "Iron and manganese alkoxide cubes," Journal of American Chemical Society, (1993) vol. 115, pp. 11752-11766.
Andreas Stein, et al., "Turning down the heat: design and mechanism in solid-state synthesis," Science, vol. 259, No. 5101, Mar. 12, 1993, pp. 1558-1564.
Alan Wilson, et al., "Detection of Nitro Compounds by Organic Semiconductor Sensors," Sensors and Actuators B 18-19, 1994, pp. 511-514.
Kingsley L. Taft, et al., "Synthesis, structure, and electronic properties of a mixed-valent dodecairon Oxo complex, a model for the biomineralization of ferritin," Inorganic Chemistry, (1994) 33, pp. 1510-1520.
B.F. Abrahams, et al., "Assembly of porphyrin building blocks into network structures with large channels," Nature vol. 369, Jun. 30, 1994 pp. 727-729.
O.M. Yaghi, et al., "Hydrothermal Synthesis of a Metal-Organic Framework Containing Large Rectangular Channels," J. Am. Chem. Soc. 1995, 117, 10401-10402.
Katerina Dimitrou, et al., "The $[Co_4O_4]^{4+}$cubane as a quadruply-bridging unit: the mixed-valence cluster $[Co_8O_4(O_2 CPh)_{12}solv_4]$ (solv=DMF, MeCN, $H_2O$)," Inorganic Chemistry, 1995, 34, pp. 4160-4166.
O. M. Yaghi, et al., "Hydrothermal synthesis of a metal-organic framework containing large rectangular channels," Journal of the American Chemical Society, 1995, vol. 117, pp. 10401-10402.
O.M. Yaghi, et al., "Selective Binding and Removal of Guests in a Microporous Metal-Organic Framework," Nature, Dec. 14, 1995, vol. 378, pp. 703-706.
O.M. Yaghi, et al., "T-Shaped Molecular Building Units in the Porous Structure of Ag(4,4'-bpy)·$NO_3$," J. Am. Chem. Soc. 1996, 118, pp. 295-296.
O. M. Yaghi, et al., "Construction of porous solids from hydrogen-bonded metal complexes of 1,3,5-benzenetricarboxylic acid," Journal of the American Chemical Society, (1996), vol. 118, pp. 9096-9101.
William A. Groves, et al., "Prototype Instrument Employing a Microsensor Array for the Analysis of Organic Vapors, in Exhaled Breath," American Industrial Hygiene Association Journal 57:1103-1108, Dec. 1996.
Scott Hynek, et al., "Hydrogen storage by carbon sorption," Int. J. Hydrogen Energy vol. 22, No. 6, pp. 601-610 (1997).
Jian Lu, et al., "Coordination Polymers of $Co(NCS)_2$ with Pyrazine and 4,4'-Bipyridine: Syntheses and Stuctures," Inorganic Chemistry (1997) vol. 36, pp. 923-929.
Christoph Janiak, "Functional organic analogues of zeolites bases on metal-organic coordination frameworks," Angew. Chem. Int. Ed. Engl. (1997) 36, No. 13/14 pp. 1431-1434.
Mario V. Capparelli, et al., "X-ray crystallographic structure of $Ga_8(pz)_{12}O_4Cl_4\cdot 2thf$: a novel gallium pyrazololate complex with a $Ga_4O_4$ core," Chem. Comm., (1997) pp. 937-938.
O. M. Yaghi, et al., "Crystal growth of extended solids by nonaqueous gel diffusion," Chemical Materials, (1997) vol. 9, pp. 1074-1076.
Omar M. Yaghi, et al., "Construction of a new open-framework solid from 1,3,5-cyclohexane-tricarboxylate and zinc(II) building blocks," Journal Chem. Soc. Dalton Trans., (1997), pp. 2383-2384.
Victoria A. Russell, et al., "Nanoporous molecular sandwiches: pillared two-dimensional hydrogen-bonded networks with adjustable porosity," Science, vol. 276, Apr. 25, 1997, pp. 575-579.
Helmut Beinert, et al., "Iron-sulfur clusters: Nature's modular, multipurpose structures," Science, vol. 277, Aug. 1997, pp. 653-659.
Omar M. Yaghi, et al., "Synthetic Strategies, Structure Patterns, and Emerging properties in the chemistry of modular porous solids," Accounts of Chemical Research, vol. 31, No. 8, 1998. pp. 474-484.
William A. Groves, et al., "Analyzing organic vapors in exhaled breath using a surface acoustic wave sensor array with preconcentration: Selection and characterization of the preconcentrator adsorbent," Analytica Chimica Acta 371, 1998, pp. 131-143.
Michael W. Willer, et al., "Ligand Substitution Reactions of $[Re_6S_8Br_6]^{4-}$: A Basis Set of $Re_6S_8$ Clusters for Building Multicluster Assemblies," Inorganic Chemistry, (1998) vol. 37, pp. 328-333.

Hailian Li, et al., "Coordinatively unsaturated metal centers in the extended porous framwork of $Zn_3(BDC)_3 \cdot 6CH_3OH$ (BDC=1,4-benzenedicarboxylate)," Journal of American Chemical Society, 1998, vol. 120, pp. 2186-2187.

Stuart L. James, et al., "Anion-templated formation of a unique inorganic 'super adamantoid' cage $[Ag_6(triphos)_4(O_3SCF_3)_4]^{2+}$ [triphos=$(PPh_2CH_2)_3CMe$]," Chemical Communication (1998) pp. 2323-2324.

M. John Plater, et al., "Hydrothermal synthesis and characterization of $M(pdc) \cdot 3H_2O$ (pdc=2,5-pyridinedicarboxylate); M=Co, Ni, $Co_xNi_y$, (x=0.4-0.6, y=0.6-0.4)," Journal of Chemical Research, (1998), pp. 3356-3376.

Cameron J. Kepert, et al., "A porous chiral framework of coordinated 1,3,5-benzenetricarboxylate: quadruple interpenetration of the (10,3)-a network," Chem Communication (1998) pp. 31-32.

Christopher W. Jones, et al., "Organic-functionalized molecular sieves as shape-selective catalysts," Nature vol. 393, May 7, 1998, pp. 52-54.

Lin, et al., "A Novel Ocupolar Metal-Organic NLO Material Based on a Chiral 2D Coordination Network," J. Am Chem. Soc. 1999, 121, 11249-11250.

Chui, et al., "A Chemically Functionalizable Nanoporous Material $[Cu_3(TMA)_2(H_2O)_3]n$," Science, 1999, vol. 283, pp. 11148-1150.

Jack Y. Lu, et al., "A new type of Two-Dimensional Metal Coordination Systems: Hydrothermal Synthesis and Properties of the First Oxalate-bpy Mixed-Ligand Framework $2[M \ (ox)(bpy)] \ (M=Fe(II), Co(II), Ni(II), Zn(II); ox=C_2O_4^{2-}; bpy=4,4'$-bipyridine)," Inorganic Chem. 1999, 38, pp. 2695-2704.

Srinivasan Natarajan, et al., "Layered Tin (II) Oxalates possessing large apertures," Chemical Material, 1999, 11 pp. 1633-1639.

Mitsuru Kondo, et al., "Rational synthesis of stable channel-like cavities with methane gas adsorption properties: $[\{Cu_2(pzdc)_2(L)\}n]$ (pzdc=pyrazine-2,3-dicarboxylate; L=a pillar ligand)," Angew. Chem. Int. Ed. (1999) 38, No. 1/2, pp. 140-143.

Raphael G. Paptis, et al., "A $Fe^{III}/Oxo$ cubane contained in an octanuclear complex of T symmetry that is stable over five oxidation states," Angew. Chem. Int. Ed. (1999), vol. 38, No. 11, pp. 1632-1634.

Mohamed Eddaoudi, et al., "Design and synthesis of metal-carboxylate frameworks with permanent microporosity," Topics in Catalysis, 1999, vol. 9, pp. 105-111.

Stephen S.-Y Chui, et al., "A chemically functionalizable nanoporous material $[Cu_3(TMA)_2(H_2O)_3]_n$," Science, vol. 283, Feb. 19, 1999, pp. 1148-1150.

Hailian Li, et al., "Design and synthesis of an exceptionally stable and highly porous metal-organic framework," Nature, vol. 402, Nov. 18, 1999, pp. 276-279.

Seo, et al., "A Homochiral Metal-organic Porous Material for Enantioselective Separation and Catalysis,"Nature, 2000, 404, pp. 982-986.

Jeongim Park, et al., "Temperature and Humidity Compensation in the Determination of Solvent Vapors with a Microsensor System," The Royal Society of Chemistry, Analyst, 2000, 125, pp. 1775-1782.

Edward T. Zellers, et al., "Evaluating Porous-Layer Open-Tubular Capillaries as Vapor Preconcentrators in a Microanalytical System," Sensors and Actuators B 67, 2000, pp. 244-253.

Qing-Yun Cai, et al., "Vapor Recognition with an Integrated Array of Polymer-Coated Flexural Plate Wave Sensors," Sensors and Actuators B 62, 2000, pp. 121-130.

M.O. O'Keeffe, et al., "Frameworks for extended solids: geometrical design principles," Journal of Solid State Chemistry 152, pp. 3-20, 2000.

Shouheng Sun, et al., "Monodisperse FePt nanoparticles and ferromagnetic FePt nanocrystals superlattices," Science vol. 287, Mar. 17, 2000, pp. 1989-1992.

Xi Xiang Zhang, et al., "Cooperative magnetic behavior in the coordination polymers $[Cu_3(TMA)_2L_3]$ (L=$H_2O$, pyridine)," Journal of Applied Physics, vol. 87, No. 9, May 1, 2000, pp. 6007-6009.

R. Murugavel, et al., "Extended metal-organic solids based on benzenepolycarboxylic and aminobenzoic acids," Proc. Indian Acad. Sci. (Chem. Sci.) vol. 112, No. 3, Jun. 2000, pp. 273-290.

Jaheon Kim, et al., "Assembly of Metal-Organic Frameworks from Large Organic and Inorganic Secondary Building Units: New Examples and Simplifying Principles for Complex Structures," J. Am. Chem. Soc. 2001, 123, pp. 8239-8247.

Banglin Chen, et al., "Interwoven Metal-Organic Framework on a Periodic Minimal Surface with Extra-Large Pores," Science, Feb. 9, 2001, vol. 291, pp. 1021-1023.

Susan A. Bourne, et al., "Coexisting Covalent and Noncovalent Nets: Parallel Interpenetration of a Puckered Rectangular Coordination Polymer and Aromatic Noncovalent Nets," Chem. Comm., 2001, pp. 861-862.

Chang-Ge Zheng, et al., "A novel two-dimensional layer network composed of cadmium and bridging isophthalate ligand," Inorganic Chemistry Communications 4, (2001), pp. 165-167.

Brian Moulton, et al., "From molecules to crystal engineering: supramolecular isomerism and polymorphism in network solids," Chemical Reviews, 2001, vol. 101 No. 6, pp. 1629-1658.

Cynthia Stowell, et al., "Self-Assembled honeycomb networks of gold nanocrystals,"Nanoletters, (2001) vol. 1, No. 11, pp. 595-600.

Yucang Liang, et al., "Hydrothermal synthesis and characterization of the coordination polymer $[Zn(bbdc)(H_2O)]_n$ (bbdc=4,4'-bibenzene-dicarboxylate) possessing a 3D network structure," Inorganic Chemistry Communications 4 (2001) pp. 599-601.

Yen-Hsiang Liu, et al., "Hydrothermal synthesis, crystal structure, and magnetic property of copper (II) coordination networks with chessboard tunnels," Journal of Solid State Chemistry 158 (2001) vol. 158, pp. 315-319.

Chuan-De Wu, et al., "Hydrothermal synthesis of two new zinc coordination polymers with mixed ligands," Inorganic Chemistry Communications 4 (2001) pp. 561-564.

H. Tamura, et al., "Semiconductor ferromagnetism in quantum dot array," Physical Stat. Sol. (b) 224, No. 3, (2001), pp. 723 -725.

Ashleigh J. Fletcher, et al., "Adsorption dynamics of gases and vapors on the nanoporous metal organic framework material $Ni_2$ (4,4'-bipyridine)$_3(NO_3)_4$: Guest modification of host sorption behavior," Journal of the American Chemical Society (2001), vol. 123, pp. 10001-10011.

Kumar Biradha, et al., "2D and 1D coordination polymers with the ability for inclusion of guest molecules: nitrobenzene, benzene, alkoxysilanes," Journal of Inclusion Phenomena and Macrocyclic Chemistry 49, (2001) pp. 201-208.

Mohamed Eddaoudi, et al., "Modular Chemistry: Secondary building units as a basis for the design of highly porous and robust metal-organic carboxylate frameworks," Acc. Chem. Res. 2001, vol. 34, pp. 319-330.

Jaheon Kim, et al., "Assembly of metal-organic frameworks from large organic and inorganic secondary building units: new examples and simplifying principles for complex structures,"Journal of the American Chemical Society, (2001), vol. 123, pp. 8239-8247.

Susan A. Bourne, et al., "Self-assembly of nanometer-scale secondary building units into an undulating two-dimensional network with two types of hydrophobic cavity," Angew. Chem. Int. Ed., (2001), vol. 40, No. 11, pp. 2111-2113.

Jianjiang Lu, et al., "Polygons and faceted polydegra and nonporous networks," Angew. Chem. Int. Ed., (2001), vol. 40, No. 11, pp. 2113-2116.

Brian Moulton, et al., "Nonaballs: nanoscale faceted polyhedra with large windows and cavities," Chem. Commun., (2001), pp. 863-864.

Heba Abourahma, et al., "Hydroxylated nanoballs: synthesis, crystal structure, solubility and crystallization on surfaces," Chem. Comm., (2001), pp. 2380-2381.

Susan A. Bourne, et al., "1-D coordination polymers containing benzenedicarboxylate," Crystal Engineering, (2001), vol. 4, pp. 25-36.

Chia-Jung Lu, et al., "A Dual-Adsorbent Preconcentrator for a Portable Indoor-VOC Microsensor System," Analytical Chemistry, vol. 73, No. 14, Jul. 15, 2001, pp. 3349-3457.

Kosal, M.E., et al., "A functional zeolite analogue assembled from metalloporphyrins," Nature Materials, 2002, vol. 1, pp. 118-121.

Xingling Xu, et al., "A nanoporous metal-organic framework based on bulky phosphane ligands," Angew. Chem. Int. Ed, (2002) 41, No. 5 pp. 764-767.

Filipe A. Almeida Paz, et al., "Synthesis and characterization of a novel modular cadmium-organic framework with biphenyl1-4,4'-dicarboxylate," Eur. J. Inorg. Chem. (2002) pp. 2823-2828.

Zi-Guang Sun, et al., "Guest controlled coordination framework: syntheses, crystal structures and thermal properties of two three-dimensional structures of [Ce$_2$(adipate)$_3$(OH$_2$)$_4$]·6H$_2$O and [Ce$_2$(adipate)$_3$(OH$_2$)$_4$]·4H$_2$O·(adipic acid)," Inorganic Chemistry Communications 5 (2002) pp. 629-632.

Ljiubov Morris, et al., "Simple system for part-per-billion-level volatile organic compound analysis in groundwater and urban air," Measurement Science and Technology, 13, (2002) pp. 603-612.

Ming Wen, et al., "Porous silver (I) organometallic coordination polymer of triptycene, and the guest desorption and absorption," Inorganica Chimica Acta 340 (2002) pp. 8-14.

Edmund J. Cussen, et al., "Flexible sorption and transformation behavior in a microporous metal-organic framework," Journaal of the American Chemical Socity (2002), vol. 124, pp. 9574-9581.

Yu-Cang Liang, et al., "Hydrothermal syntheses, structural characterizations and magnetic properties of cobalt (II) and manganese(II) coordination polymeric complexes containing pyrazinercarboxylate ligand," Inorganic Chimica Acta 328, (2002), pp. 152-158.

Jun Tao, et al., "Assembly of a microporous metal-organic framework [Zn(bpdc)(DMSO)] (bpdc=4,4-biphenyldicarboxylate) based on paddle-wheel units affording guest inclusion," Inorganic Chemistry Communications, (2002), vol. 5, pp. 975-977.

Mohamed Eddaoudi, et al., "Systematic Design of Pore Size and Functionality in Isoreticular MOFs and Their Application in Methane Storage," Science, Jan. 18, 2002, vol. 295, pp. 469-472.

Yaghi, et al., "Reticular Synthesis and the Design of New Materials," Nature 423, 2003, pp. 705-714.

Smithenry, D.W., et al., "A Robust Microporous Zinc Porphyrin Framework Solid," Inorg. Chem. 2003, vol 42, pp. 7719-7721.

Jinxi Chen, et al., "A new open metal-organic framework [(Zn$_8$ )(GeO$_4$ )(C$_8$ H$_4$ 0$_4$)$_6$]$_n$ , Constructed by Heterometallic Cluster Zn$_8$ (GeO$_4$) Secondary Building Units," Chemistry Letters vol. 32, No. 5 (2003).

Enrique Colacio, et al., "Hydrothermal syntheses, crystal structures, and properties two-dimensional homo- and heterometallic cyanide-bridged complexes: [Cu$_2$(CN)$_2$(bpym)] and [Fe((bipy)$_2$(CN)$_4$Cu$_2$](bpym=2,2'-Bipyrimidine, bipy=2,2'-Bipyridine)," Inorganic Chemistry 2003, 42, pp. 4209-4214.

Li-Ping Zhang, et al., "Hydrothermal synthesis and crystal structures of three novel lanthanide coordination polymers with glutarate and 1,10-phenanthroline," Journal of Molecular Structure 646 (2003) pp. 169-178.

Li-Ping Zhang, et al., "Hydrothermal synthesis and crystal structure of neodymium(III) coordination polymers with isophthalic acid 1,10-phenanthroline," Polyhedron 22 (2003) pp. 981-987.

Hidekazu Arii, et al., "Unique three-dimensionally expanded nanoporous structure constructed with a Cu(I) and 1,3,5-triaminocyclohexane having a 3-fold axial symmetry," Chemistry Letters vol. 32 No. 1(2003) pp. 106-107.

Aleksey Vishnyakov, et al., "Nanopore structure and sorption properties of Cu-BTC metal-organic framework," Nano Letters, vol. 3, No. 6, (2003) pp. 713-718.

T. J. Prior, et al., "Designed layer assembly: a three-dimensional framework with 74% extra-framework volume by connection of infinite two-dimensional sheets," Chem. Commun., (2003), pp. 500-501.

Yang-Guang Li, et al., A novel three-dimensional metal-organic framework constructed from two-dimensional interpenetrating layers based on trinuclear cobalt clusters: [Co$_3$(btec)(C$_2$O$_4$)(H$_2$O)$_2$]$_n$. Eur. Journal of Inorganic Chemistry (2003) pp. 2567-2571.

Sujit K. Ghosh, et al., "Coexistence of water dimer and hexamer clusters in 3D metal-organic framework structures of Ce(III) and Pr(III) with pyridine-2,6-dicarboxylic acid," Inorganic Chemistry, (2003) vol. 42, pp. 8250-8254.

Hee K. Chae, et al., "Design of frameworks with mixed triangular and octahedral building blocks exemplified by the structure of [Zn$_4$O(TCA)$_2$] having the pyrite topology," Angew. Chem. Int. Ed., (2003), vol. 42, pp. 3907-3909.

Nathaniel L. Rosi, et al., "Hydrogen Storage in Microporous Metal-Organic Frameworks," Science, May 16, 2003, vol. 300, pp. 1127-1129.

Wei-Cheng Tian, et al., "Microfabricated Preconcentrator-Focuser for a Microscale Gas Chromatograph," Journal of Microelectromechanical Systems, vol. 12, No. 3, Jun. 2003, pp. 264-272.

Yun-Qi Tian, et al., "{[In$_3$ (pzdc)$_6$]$^{3-}$} Metal-Organic Framework of Distorted NbO-like Net (pzdc=Pyrazine-2,3-dicarboxylato)," Chemistry Letters, vol. 32, No. 9, pp. 796-797, Aug. 4, 2003.

Jason K. Holt, et al., "Fabrication of a Carbon Nanotube-Embedded Silicon Nitride Membrane for Studies of Nanometer-Scale mass Transport," American Chemical Society, Nano Letters 2004, vol. 4, No. 11, pp. 2245-2250.

Jessee L.C. Rowsell, et al., "Metal-organic frameworks: a new class of porous materials," Microporous and Mesoporous Materials 73, 2004, pp. 3-14.

Suman Mukhopadhyay, et al., "Honeycomb Nets with Interpenetrating Frameworks Involving Iminodiacetato-Copper (II) Blocks and Bipyridine Spacers: Syntheses, Characterization, and Magnetic Studies," Inorganic Chemistry, 2004, 43, pp. 3413-3420.

Ming-Hua Zeng, et al., "Crystal-to-crystal transformations of a microporous metal-organic laminated framework triggered by guest exchange, dehydration and readsorption," Dalton Trans., 2004, pp. 2217-2223.

Junji Ito, et al., "Discrimination of halitosis substance using QCM sensor array and a preconcentrator," Sensors and Actuators B 99 (2004) pp. 431-436.

Qiang Wei, et al., "A manganese metal-organic framework which remains crystalline on desolvation, and which gives insight into the rotational freedom of framework aromatic groups," Microporous and Mesoporous Materials 73 (2004) pp. 97-100.

Xiang-Jun Zheng, et al. "Hydrothermal syntheses, structures and magnetic properties of two transition metal coordination polymers with a square grid framework," Polyhedron 23, (2004) pp. 1257-1262.

Klaus Schlichte, et al., "Improved synthesis, thermal stability and catalytic properties of the metal-organic framework compound Cu$_3$9BTC)$_2$," Microporous and Mesoporous Materials 73(2004) pp. 81-88.

Danil N. Dybtsev, et al., "Rigid and flexible: A Highly Porous Metal-Organic Framework with Unusual Guest-Dependent Dynamic Behavior," Angew. Chem. Int. Ed. (2004) 43, pp. 5033-5036.

Danil N Dybtsev, et al., "Three-dimensional metal-organic framework with (3,4)-connected net, syntheisized from an ionic liquid medium," Chem. Commun. (2004) pp. 1594-1595.

Ryo Kitaura, et al., "Rational Design and Crystal Structure Determination of a 3-D Metal-Organic Jungle-Gym-Like Open Framework," Inorganic Chemistry, (2004), vol. 43, No. 21, pp. 6522-6524.

Filipe A. Almeida Paz, et al., "Synthesis and Characterization of a Novel Cadmium-Organic Framework with Trimesic Acid and 1,2-Bis(pyridyl)ethane," Inorganic Chemistry (2004), vol. 43, No. 13, pp. 3948-3954.

Eithne Tynan, et al., "Solvent templated synthesis of metal-organic frameworks: structural characterization and properties of the 3D network isomers {[Mn(dcbp)]·1/2 DMF}$_n$ and {[Mn(dcbp)]·2H$_2$O}$_n$," Chem. Comm. (2004), pp. 776-777.

Haitao Xu, et al., "Two new microporous coordination polymers constructed by ladder-like and ribbon-like molecules with cavities," journal of Molecular Structure 693 (2004) pp. 11-15.

Cheng-Yong Su, et al., "A three-dimensional, noninterpenetrating metal-organic framework with the moganite topology: a simple (4$^2$. 6$^2$.8$^2$)(4.6$^4$.8)$_2$ net containing two kinds of topologically nonequivalent points," Inorganic Chemistry Communication (2004), vol. 43, pp. 6881-6883.

Cheng-Yong Su, et al., "Exceptionally stable, hollow tubular metal-organic architectures: synthesis, characterization, and solid-state transformation study," Journal of the American Chemical Society, (2004) vol. 126, pp. 3576-3586.

Giannis S. Papaefstathiou, et al., "A 2D metal-organic framework with two different rhombus-shaped cavities: a rare example of a (4,4)-net with alternating metal and organic nodes," Microporous and Mesoporous Materials 71(2004) pp. 11-15.

Yan BAi, et al., "A three dimensional porous metal-organic framework [Fe$_4$L$_6$·(DMF)$_3$·(H$_2$O)$_{10}$] constructed from neutral discrete Fe$_4$L$_6$ pyramids [H$_2$L=1,3-benzodihydroxamix acid]," Chem. Commun., (2004) pp. 186-187.

M. J. Rosseinsky, "Recent developments in metal-organic framework chemistry: design, discovery, permanent porosity and flexibility," Microporous and Mesoporous Materials 73(2004), pp. 15-30.

Hye Jin Choi, et al., "Dynamic and redox active pillared bilayer open framework: single-crystal-to-single crystal transformations upon guest removal, guest exchange, and framework oxidation," Journal of the American Chemical Society, (2004), vol. 126, pp. 15844-15851.

Ashleigh J. Fletcher, et al., "Adsorption of gases and vapors on nanoporous Ni$_2$(4,4'-bipyridine)$_3$(NO$_3$)$_4$ metal-organic framework materials templated with methanol and ethanol: structural effects in adsorption kinetics," Journal of the American Chemical Society, (2004), vol. 126, pp. 9750-9759.

Xinlong Wang, et al., "Designed double layer assembly: a three-dimensional open framework with two types of cavities by connection of infinite two-dimensional bilayer," Chem. Comm., (2004), pp. 378-379.

Yaqin Guo, et al., "Synthesis and Crystal Structure of a Novel Three-Dimensional Supramolecular Network Containing One-Dimensional Honeycomb-Like Channels," Inorganica Chimica Acta, vol. 357, (2004) pp. 4582-4586.

Liying Duan, et al., "Hydrothermal synthesis and crystal structures of two novel rare earth coordination polymers based on pyridine-2,6-dicarboxylic acid," Journal of Molecular Structure 689, (2004) pp. 269-274.

Sujit K. Ghosh, et al., "Puckered-boat conformation hexameric water clusters stabilized in a 2D metal-organic framework structure built from Cu(II) and 1,2,4,5-benzenetetracarboxylic acid," Inorganic Chemistry, (2004), vol. 43, pp. 5180-5182.

Hee K. Chae, et al., "A route to high surface area, porosity and inclusion of large molecules in crystals," Nature, vol. 427, Feb. 2004, pp. 523-527.

Xuebo Zhao, et al., "Hysteretic adsorption and desorption of hydrogen by nanoporous metal-organic frameworks," Science, vol. 306, Nov. 5, 2004, pp. 1012-1015.

Dat T. Tran, et al., "Open Metal-Organic Framework Containing Cuprate Chains," Inorganic Chemistry, vol. 44, No. 18, 2005, pp. 6192-6196.

Chia-Jung Lu, et al., "First-Generation Hybrid MEMS Gas Chromatograph," Lab on a Chip, 2005, 5, pp. 1123-1131.

C.E. Davis, et al., "Enhanced Detection of $m$-xylene Using a Preconcentrator with a Chemiresistor Sensor," Sensors and Actuators B 104, 2005, pp. 207-216.

A.T. Carvalho, et al., "Improvement on Organic Compound Adsorption and/or Detection by Using Metallic Thin Films Deposited onto Highly Rough Silicon Substrates," Sensors and Actuators B 108, 2005, pp. 947-954.

Yanjun Tang, et al., "A Micro-post Preconcentrator for a Microscale Gas Chromatography System," 2005 Micro Total Analysis Systems Conference (Boston, MA, Oct. 2005); Transducers Research Foundation Proceedings of the 2005 Micro Total Analysis Systems Conference, p. 660-662 (2005).

Bing-Bing Ding, et al., "Pillared-Layer Microporous Metal-Organic Frameworks Constructed by Robust Hydrogen Bonds. Synthesis, Characterization, and Magnetic and Adsorption Properties of 2,2'-Biimidazole and Carboxylate Complexes," Inorganic Chemistry vol. 44, No. 224, 2005, pp. 8836-8845.

Qianrong Fang, et al., "A metal-organic framework with the ziolite MTN Topology containing large cages of vol. 2.5 nm3," Angew. Chem. Int. Ed. 2005, 44, pp. 3845-3848.

Banglin Chen, et al., "High H$_2$ adsorption in a microporous metal-organic framework with open metal sites," Angew; Chem. Int. Ed. 2005, 44, pp. 4745-4749.

Drew L. Murphy, et al., "A chiral, heterometallic metal-organic framework derived from a tris(chelate) coordination complex," Chemistry Communication, 2005, pp. 5506-5508.

Radu Custelcea, et al., "A metal-organic framework functionalized with free carboxylic acid sites and its selective binding of a CI(H$_2$O)$_4$-cluster," J. Am. Chem. Soc. 2005, 127, pp. 16362-16363.

Thomas Devic, et al., "MIL-103, A 3-D lanthanide-based metal organic framework with large one-dimensional tunnels and a high surface area," J. Am. Chem. Soc. 2005, 127, pp. 12788-12789.

Jarrod F. Eubank, et al., "Terminal co-ligand directed synthesis of a neutral, non-interpenetrated (10,3)-$a$ metal-organic framework," Chemical Communication, 2005, pp. 2095-2097.

Lei Wang, et al., "Two-dimensional metal-organic framework constructed from 4,4'-bipydine and 1,2,4-benzenetricarboxylate: synthesis, structure and magnetic properties," Journal of Solid State Chemistry, 178 (2005) pp. 3359-3365.

Ru-Qiang Zou, et al., "A hydrogen-bonded 3D coordination network of Co$^{II}$ with 4-($p$-benzoxy)-1,2,4-triazole: hydrothermal synthesis, characterization, crystal structure and emission property," Journal of Molecular Structure 737 (2005) pp. 125-129.

Jun Hong, "[Zn$_2$(BTDA)(bpy)(H$_2$O)]·0.5bpy: a new three-dimensional metal-organic framework constructed from flexible and rigid mixed ligands," Journal of Molecular Structure 752 (2005) pp. 166-169.

Henrik Fano Clausen, et al., "Solvothermal synthesis of new metal organic framework structures in the zinc-terephthalic acid-dimethyl formamide system" Journal of Solid State Chemistry 178, (2005) pp. 3342-3351.

Giovanni Garberoglio, et al., "Adsorption of gases in metal organic materials: comparison of simulations and experiments," Journal of Physical Chemistry B (2005) 109, pp. 13094-13103.

Gregory J. Halder, et al., "In situ single-crystal x-ray diffraction studies of desorption and sorption in a flexible nanoporous molecular framework material," Journal of the American Chemical Society (2005), 127, pp. 7891-7900.

Ryo Kitaura, et al., "Formation and characterization of crystalline molecular arrays of gas molecules in a 1-dimensional ultramicropore of a porous copper coordination polymer," Journal of Physical Chemistry B, (2005) 109, pp. 23378-23385.

Zheming Wang, et al., "Synthesis and characterization of a porous magnetic diamond framework, Co$_3$(CHOO)$_6$, and its N$_2$ sorption characteristic," Inorganic Chemistry, (2005), vol. 44, No. 5, pp. 1230-1237.

Hendrik Dathe, et al., "Metal organic frameworks based on Cu$^{2+}$ and benzene-1,3,5-tricarboxylate as host for SO$_2$ trapping agents," C. R. Chimie 8 (2005) pp. 753-763.

Jeong Yong Lee, et al., "Gas sorption properties of microporous metal organic frameworks," Journal of Solid State Chemistry 178 (2005) pp. 2527-2532.

Jeong Yong Lee, et al., "Achieving high density of adsorbed hydrogen in microporous metal organic frameworks," Advanced Materials (2005) vol. 17, pp. 2703-2706.

Carine Livage, et al., "A three-dimensional metal-organic framework with an unprecedented octahedral building unit," Angew. Chem. Int. Ed. (2005) vol. 44, pp. 6488-6491.

Andrea M. Goforth, et al., "Connecting small ligands to generate large tubular metal-organic architectures," Journal of Solid State Chemistry 178, (205) pp. 2511-2518.

Linhua Xie, et al., "A three-dimensional porous metal-organic framework with the rutile topology contructed from triangular and distorted octahedral building blocks," Chem. Comm., (2005) pp. 2402-2404.

Giannis S. Papaefstathiou, et al., "Design and construction of a 2D metal organic framework with multiple cavities: a nonregular net with a paracyclophane that codes for multiply fused nodes," Journal of the American Chemical Society, vol. 127, No. 41 (2005) pp. 14160-14161.

O.I. Lebedev, et al., "First direct imaging of giant pores of the metal-organic framework MIL-101," Chemistry Materials, (2005), vol. 17, pp. 6525-6527.

Dat T. Tran, et al., "Open metal-organic framework containing cuprate chains," Inorganic Chemistry, (2005) vol. 44, No. 18, pp. 6192-6196.

Ashleigh J. Fletcher, et al., "Flexibility in metal-organic framework materials: Impact on sorption properties,", Journal of Solid State Chemistry 178, (2005) pp. 2491-2510.

Tatsuhiko Sagara, et al., "New isoreticular metal-organic framework materials for high hydrogen storage, capacity;" The Journal of Chemical Physics 123, 214707 (2005), pp. 1-6.

Tatsuhiko Sagara, et al., "Binding energies of hydrogen molecules to isoreticular metal-organic framework materials," The Journal of Chemical Physics 123, 014701 (2005), pp. 1-4.

Eun Young Lee, et al., "Multifunctionality and crystal dynamics of a highly stable, porous metal-organic framework [$Zn_4O(NTB)_2$]" Journal of the American Chemical Society (2005) vol. 127, pp. 6374-6381.

Eun Young Lee, et al., Multifunctionality and crystal dynamics of a highly stable, porous metal-organic framework [$Zn_4O(NTB)2$]Journal of the American Chemical Society, (2005), vol. 127, pp. 6374-6381.

Xiao-Jun, et al., "A three-dimensional zinc trimesate framework:[$(CH_3)_2NH_2$][$Zn(C_9H_3O_6)$]·($C_3H_7NO$)," Applied Organometallic Chemistry (2005), vol. 19, pp. 694-695.

D. Maspoch, et al., "EPR characterization of a nanoporous metal-organic framework exhibiting a bulk magnetic ordering," Journal of Physics and Chemistry of Solids, (2005), vol. 65, pp. 819-824.

Xin-Long Wang, et al., "An unprecedented eight-connected self-penetrating network based on pentanuclear zinc cluster building blocks," Chem. Communication, (2005), pp. 4789-4791.

Xiuli Bai yanguang Li, et al., "A novel three- dimensional hybrid framework based on fishbone-like copper halide inorganic units," Inorganica Chimica Acta 358, (2005), pp. 2571-2574.

Jorge Gonzalez, et al., "Dueterium NMR studies of framework and guest mobility in the metal organic framework compound MOF-5, $Zn_4O(O_2CC_6H_4CO_2)_3$," Microporous and Mesoporous Materials 84, (2005), pp. 97-104.

Ru-Qiang Zou, et al., "Rational assembly of a 3D metal-organic framework for gas adsorption with predesigned cubic buildings blocks and ID open channels," Chem. Commun., (2005) pp. 3526-3528.

Yi-Hang Wen, et al., Hydrothermal synthesis, crystal structures and characterizations of three new copper coordination polymers, Inorganica Chimica Acta 358 (2005) pp. 3347-3354.

Sujit K. Ghosh, et al., "Infinite chains of quasi-plana hexameric water clusters stabilized in a metal-organic framework built from $Co^{II}$ and pyrazine-2,3,5,6-tetracarboxylic acid," Eur. Journal of Inorganic Chemistry (2005), pp. 4880-4885.

Miguel Fuentes-Cabrera, et al., "Electronic structure and properties of isorcticular metal-organic frameworks: the case of $M$-IRMOF1 ($M$=Zn, Cd, Be, Mg, and Ca)," The Journal of Chemical Physics vol. 123, (2005), 124713, pp. 1-5.

Jianghua He, et al., "Synthesis, structure, and luminescent property of a heterometallic metal-organic framework constructed form rod-shaped secondary building blocks," Inorganic Chemistry, (2005) vol. 44, pp. 9279-9282.

Andrew R. Millward, et al., "Metal-organic frameworks with exceptionally high capacity for storage of carbon dioxide at room temperature," Journal of the American Chemical Society, (2005), vol. 127, pp. 17998-17999.

Banglin Chen, et al., "Transformation of a metal-organic framework from the Nbo to PtS net, " Inorganic Chemistry, (2005), vol. 44, pp. 181-183.

Zhenqiang Wang, et al., "Ternary nets formed by self-assembly of triangles, squares, and tetrahedra," Angew. Chem. Int. Ed., (2005), vol. 44, pp. 2877-2880.

T. Yildirim, et al., "Direct observation of hydrogen adsorption sites and nanocage formation in metal-organic frameworks,"Physical Review Letters, Nov. 18, 2005, vol. 95, 215504 pp. 1-4.

Danil N. Dybtsev, et al., "A Homochiral Metal-Organic Material with Permanent Porosity, Enantioselective Sorption Properties, and Catalytic Activity," Agnew, Chem. Int. Ed., 2006, 45, pp. 916-920.

Flachbart, et al., "Design and fabrication of a multilayered polymer microfluidic chip with nanofluidic interconnects via adhesive contact printing," Lab-On-A-Chip, 6, 667-674, 2006.

Timothy M. Long, et al., "Water-Vapor Plasma-Based Surface Activation for Trichlorosilane Modification of PMMA," Langmuir, vol. 22, No. 9, 2006, pp. 4104-4109.

Eliphas Wagner Simoes, et al., "Study of preconcentration of no-polar compounds in microchannels with constrictions," Sensors and Actuators B 115, 2006, pp. 232-239.

Ru-Qiang Zou, et al., "Strong fluorescent emission of a new fourfold-interpenetrated diamondoid metal-organic framework of zinc(II) urocanate with one-dimensional open channels," Microporous and Mesoporous Materials 91, 2006, pp. 233-237.

Qiong Ye, et al., "Ferroelectric Metal-organic framework with a high dielectric constant," JACS, 2006, 128, pp. 6554-6555.

Banglin Chen, et al., "A microporous metal-organic framework for gas-chromatographic separation of alkanes," Angew. Chem. Int. Ed. 2006, 45, 1390-1393.

Pascal D. C. Dietzel, et al., "Hydrogen adsorption in a nickel based coordination polymer with open metal sites in the cylindrical cavities of the desolvated framework," Chemical Communication, 2006, pp. 959-961.

Lei Wang, et al., "Highly stable chiral cadmium 1,2,4-benzenetricarboxylate: Synthesis, structure, and NLO and fluourescence properties," Inorganic Chemistry, vol. 45, No. 6, 2006, pp. 2474-2478.

Feng Zheng, et al., "Single-Walled Carbon Nanotube paper as a Sorbent for Organic Vapor Preconcentration," Analytical Chemistry, 2006, vol. 78, No. 7, pp. 2442-2446.

Rasmus Damgaard Poulsen, et al., "Solvothermal synthesis, multi-temperature crystal structures and physical properties of isostructural coordination polymers, $2C_4H_{12}N^+$-[$M_3(C_8H_4O_4)_4$]$^{2-}$·$3C_{5H11}NO$ $M$=Co, Zn," Acta Crystallography (2006) B62, pp. 254-254.

Piotr Krawiec, et al., "Improved hydrogen storage in the metal-organic framework $Cu_3(BTC)_2$," Advanced Engineering Materials (2006) 8 No. 4, pp. 293-296.

Cameron J. Kepert, "Advanced functional properties in nanoporous coordination framework materials," Chemical Communication, (2006) pp. 695-700.

Long Pan, et al., "Seperation of hydrocarbons with a microporous metal-organic framework," Angew. Chem. Int. Ed., (2006) vol. 45, pp. 616-619.

Shuangquan Zang, et al., "Interweaving of triple-helical and extended metal-o-metal single-helical chains with the same helix axis in a 3D metal-organic framework," Inorganic Chemistry (2006), vol. 45, No. 10, pp. 3855-3857.

U. Mueller, et al., "Metal-organic framework—prospective industrial applications," Journal of Materials Chemistry, (2006) vol. 16, pp. 626-636.

Frank Stallmach, et al., "NMR studies on the diffusion of hydrocarbons on the metal-organic framework material ' MOF-5," Angew. Chem. Int. Ed. (2006), vol. 45, pp. 2123-2126.

Gyungse Park, et al., "Solvothermal synthesis, crystal structure, and magnetic properties of [$Co_3(SDA)_3(DMF)_2$]; 2-D layered metal-organic framework derived from 4,4' stilbenedicarboxylic acid ($H_2SDA$)," Bull. Korean Chem. Soc. (2006) vol. 27, No. 3 pp. 443-446.

Enrica Biemmi, et al., "Synthesis and characterization of a new metal organic framework structure with a 2D porous system: ($H_2Net_2$)[$Zn_3(BDC_4)$] 3DEF," Solid State Sciences 8, (2006), pp. 363-370.

Suzy Suable, et al., "An EXAFS study of the formation of a nanoporous metal-organic framework: evidence for the retention of secondary building units during synthesis," Chem Commun., (2006) pp. 1518-1520.

Cheng-Zhi Xie, et al., "A novel 3D $Cu^I$ metal-organic framework with middle-size channels despite the sixfold $ThSi_2$ interpenetrating topological structure," Eur. Journal of Inorganic Chemistry (2006) pp. 1337-1340.

Subhadip Neogi, et al., "Metal-organic frameworks of lanthanide (III) ions with a pod and bearing terminal carboxylates: Identification of water clusters of different nuclearity," Polyhedron 25 (2006) pp. 1491-1497.

C. Prestipino, et al., "Local structure of framework Cu(II) in HKUST-1 metallorganic framework: spectroscopic characterization upon activation and interaction with adsorbates," Chemical Materials, (2006), vol. 118, pp. 1337-1346.

Andrea C. Sudik, et al., "A metal-organic framework with a hierarchical system of pores and tetrahedral building blocks," Angew. Chem. Int. Ed., (2006), vol. 45, pp. 2528-2533.

Antek G. Wong-Foy, et al., "Exceptional $H_2$ saturation uptake in microporous metal-organic frameworks," Journal of the American Chemical Society, (2006), vol. 128, pp. 3494-3495.

Jianghua He, et al., "Three metal-organic frameworks prepared from mixed solvents of DMF and HAc," Microporous and Mesoporous Materials, (2006), vol. 90, pp. 145-152.

Byunghoon Bae, et al., "A Touch-Mode Capacitance Microvalve Equipped with High Speed and Pressure Microsecond Switching Performance," MEMS 2006, Istanbul, Turkey, Jan. 22-26, 2006, pp. 766-769.

Patrick R. Lewis, et al., "Recent Advancements in the Gas-Phase MicroChemLab," IEEE Sensors Journal, vol. 6, No. 3, Jun. 2006, pp. 784-795.

Shaurya Prakash, et al., "Electroosmotic Flow in 'Click' Surface Modified Microfluidic Channels," Proceedings of ASME ICNMM2006, 4$^{th}$ International Conference on Nanochannels, Microchannels and Minichannels, Jun. 19-21, 2006; Limerick, Ireland, Paper No. ICNMM2006-96153.

J. Yeom, et al., "Design and Characterization of Micropost-Filled Reactor for the Minimal Pressure Drop and Maximal Surface-Area-to-Volume Ratio," Proceedings of IMECE 2006, 2006 ASME International Mechanical Engineering angress and Exposition, Nov. 5-10, 2006, Chicago, Illinois, USA, IMECE2006-15836.

Zhuojia Lin, et al., "Microwave-Assisted Synthesis of Anionic Metal-Organic Frameworks Under Ionothermal Conditions," The Royal Society of Chemistry 2006, Chem. Commun., 2006, pp. 2021-2023.

N. Rajic, et al., "An Evidence for a Chain to Network Transformation During the Microwave Hydrothermal Crystallization of an Open-Framework Zinc Terephthalate," J. Porous Mater. 2006,vol. 13: pp. 153-156.

Kate Grudpan, et al., "Flow Injection Spectrophotometric Determination of As(III) and As(V) Using Molybdate Reagent With Solid Phase Extraction In-Valve Column," Indian Journal of Chemistry, vol. 42A, Dec. 2003, pp. 2939-2944.

Ioana Voiculescu, et al., "Micropreconcentrator for Enhanced Trace Detection of Explosives and Chemical Agents," IEEE Sensors Journal, vol. 6, No. 5, Oct. 2006, pp. 1094-1104.

International Preliminary Report on Patentability, dated May 23, 2007, in PCT/US2006/038998.

International Search Report, dated May 23, 2007.

Panda, A. B. et al., Microwave Synthesis of Highly Aligned Ultra Narrow Semiconductor Rods and Wires, J. Am. Chem. Soc., 128:2790-2791 (2006).

Tompsett, G. A. et al., Microwave Synthesis of Nanoporous Materials, ChemPhysChem, 7:296-319 (2006).

Lu, Q. et al., Biomolecule and/or Microwave-Assisted Solvothermal Syntheses of Nanomaterials, AZo Journal of Materials Online vol. 1, (2005).

Grudpan, K. et al., Flow injection spectrophotometric determination of As(III) and As(V) using molybdate reagent with solid phase extraction in-valve column, Indian Journal of Chemistry, 42A:2939-2944 (2003).

Bochobza-Degani, O. et al., on the effect of residual charges on the pull-in parameters of electrostatic actuators, Sensors and Actuators a 97-98:563-568 (2002).

Bosch, D. et al., A silicon microvalve with combined electromagnetic/electrostatic actuation, Sensors and Actuators 37-38:684-692 (1993).

Castaner, L. M. et al., Pull-in time-energy product of electrostatic actuators: comparison of experiments with simulation, Sensors and Actuators, 83:263-269 (2000).

Legtenberg, R. et al., Electrostatic Curved Electrode Actuators, Journal of Microelectromechanical Systems 6(3):257-265 (1997).

Messner, S. et al., 3-way silicon microvalve for pneumatic applications with electrostatus actuation principle, Microfluid Nanofluid 89-96 (2006).

Messner, S. et al., Electrostatic driven 3-way silicon microvalve for pneumatic applications, IEEE 88-91 (2003).

Oberhammer, J. et al., Design and fabrication aspects of an S-shaped film actuator BH based DC to RF MEMS switch, Journal of Microelectromechanical Systems 13(3):421-428.

Ohnstein, T. et al., Micromachined silicone microvalve, Proc. IEEE Micro Electro Bi Mechanical Systems, an Investigation of Micro Structures, Sensors, Actuators, Machines and Robots, Napa Valley CA 95-98 (1990).

Philpott, M. L. et al., Switchable electrostatic micro-valves with high hold-off pressure, Technical Digest of the 2000 Solid-State Sensor and Actuator Workshop, 226-229.

Sato, K. et al., An electrostatically actuated gas valve with an S-shaped film element, J. Micromech. Microeng. 4:205-209 (1994).

Schaible, J. et al., Electrostatic microvalves in silicon with 2-way-function for industrial applications, The 11th International Conference on Solid-State Sensors and Actuators, Munich, Germany 928-931 (2001).

Shikida; M. et al., Characteristics of an electrostatically-driven gas valve under high pressure conditions, Center for Materials Processing Technology 235-240 (1994).

Shikida, M. et al., Electrostatically driven gas valve with high conductance, Journal of Microelectromechanical Systems, 3(2):76-80 (1994).

Shikida, M. et al., Fabrication of an S-shaped microactuator, Journal of Microelectromechanical Systems, 6(1):18-24 (1997).

Shikida, M. et al., Micromachined S-shaped actuator, Sixth International Symposium on Miccro Machine and Human Science 167-172 (1995).

Shikida, M. et al., Response time measurement of electrostatic S-shaped film actuator related to environmental gas pressure conditions, IEEE 210-215 (1996).

Vandelli, N. et al., Development of a MEMS microvalve array for fluid flow control, Journal of Microelectromechanical Systems 7(4):395-403 (1998).

Yang, X. et al., an electrostatic, on/off microvalve designed for gas fuel delivery for the MIT microengine, Journal of Microelectromechanical Systems, 13(4):660-668 (2004).

Luis Castaner et al., Speed-energy optimization of electrostatic actuators based on Pull-in, IEEE Journal of Microelectromechanical Systems, vol. 8, No. 3, pp. 257-265 (1999).

International Search Report and Written Opinion corresponding to the PCT application PCT/US07/009243 filed Apr. 13, 2007.

International Search Report and Written Opinion corresponding to the PCT application PCT/US2008/053959 filed Feb. 14, 2008.

International Search Report and Written Opinion corresponding to the PCT application PCT/US06/29296 filed Jul. 26, 2006.

Han et al., Micro-fabricated membrane gas valves with a non-stiction coating deposited by $C_4 F_8$/Ar plasma, J. Micromech. Microeng. 18 (2008) 095015, pp. 1-9.

Yeom et al., The design, fabrication and characterization of a silicon microheater for an integrated MEMS gas preconcentrator, J. Micromech. Microeng. 18 (2008) 125001, pp. 1-12.

Han et al. Surface energy approach and AFM verification of the (CF)n treated surface effect and its correlation with adhesion reduction in microvalves, J. Micromech. Microeng. 19 (2009) 085017, pp. 1-9.

Radadia et al., The fabrication of all-silicon micro gas chromatography columns using gold diffusion eutectic bonding, J. Microtech. Microeng. 20 (2010) 015002, pp. 1-7.

Radadia et al., Micromachined GC Columns for Fast Separation of Organophosphonate and Organosulfur Compounds, Anal. Chem. 2008,80, pp. 4087-4094.

Radadia et al., Partially Buried Microcolumns for Micro Gas Analyzers, Anal. Chem. 2009; 81, pp. 3471-3477.

Han et al., Smooth Contact Capacitive Pressure Sensors in Touch- and Peeling-Mode Operation, IEEE Sensors Journal, vol. 9, No. 3, Mar. 2009, pp. 199-206.

Radadia et al., The Effect of Microcolumn Geometry on the Performance of Micro-Gas Chromatography Columns for Chip Scale Gas Analyzers, Sensors and Actuators B: Chemical (2010), doi:10.1016/j.snb.2010.07.002, pp. 1-29.

Bae et al., A Bidirectional Electrostatic Microvalve With Microsecond Switching Performance, Journal of Microelectromechanical Systems, vol. 16, No. 6, Dec. 2007, pp. 1461-1471.

Zhong et al., Characterization of a high-performance portable GC with a chemiresistor array detector, Analyst, 2009,134, pp. 283-293.

Groves et al., Analyzing organic vapors in exhaled breath using a surface acoustic wave sensor array with preconcentration: Selection and characterization of the preconcentrator adsorbent, Analytica Chimica Acta 371 (1998) pp. 131-143.

Huff et al., A pressure-balanced electrostatically-actuated microvalve, Technical Digest, 1990 Solid-State Sensor and Actuator Workshop, pp. 123-127 (1990).

* cited by examiner

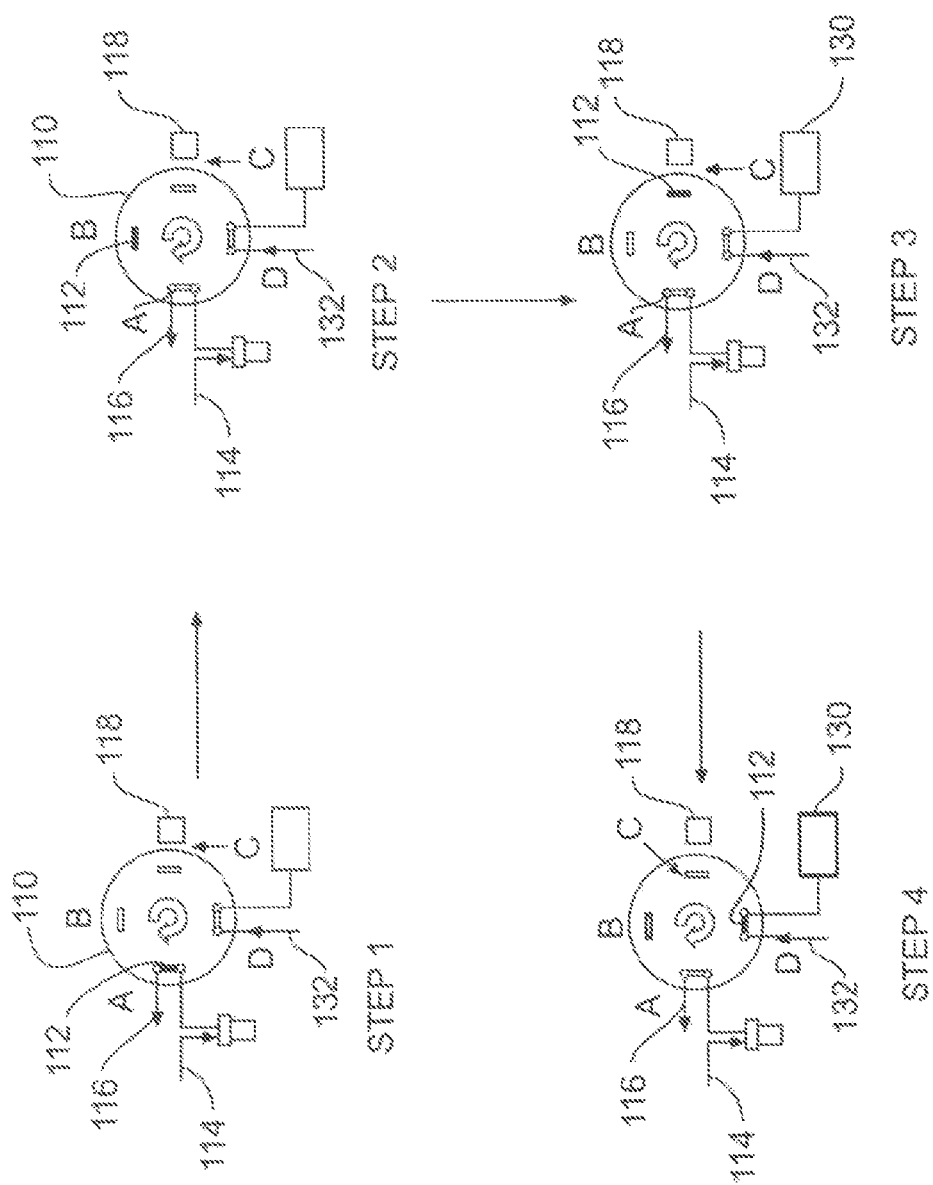

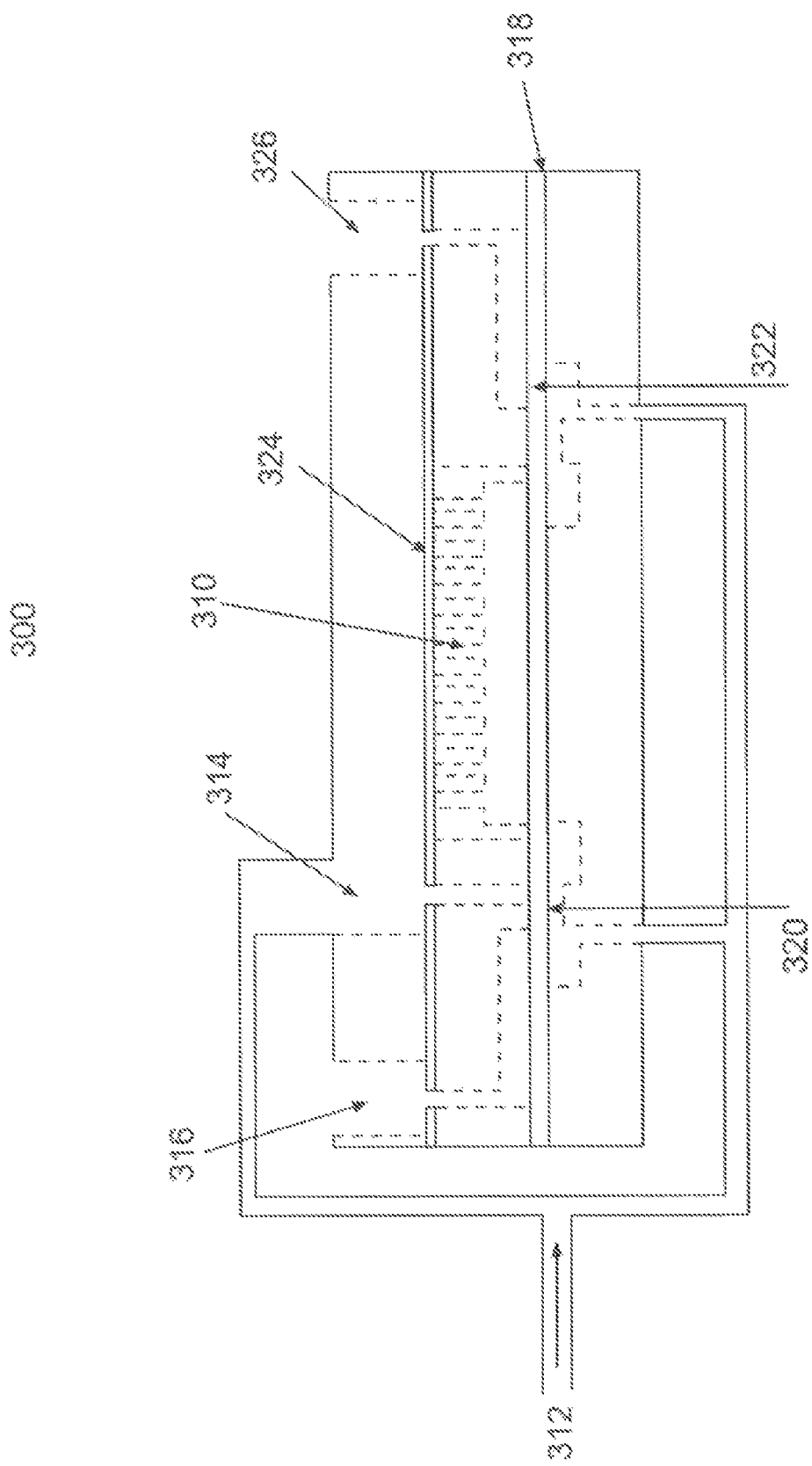

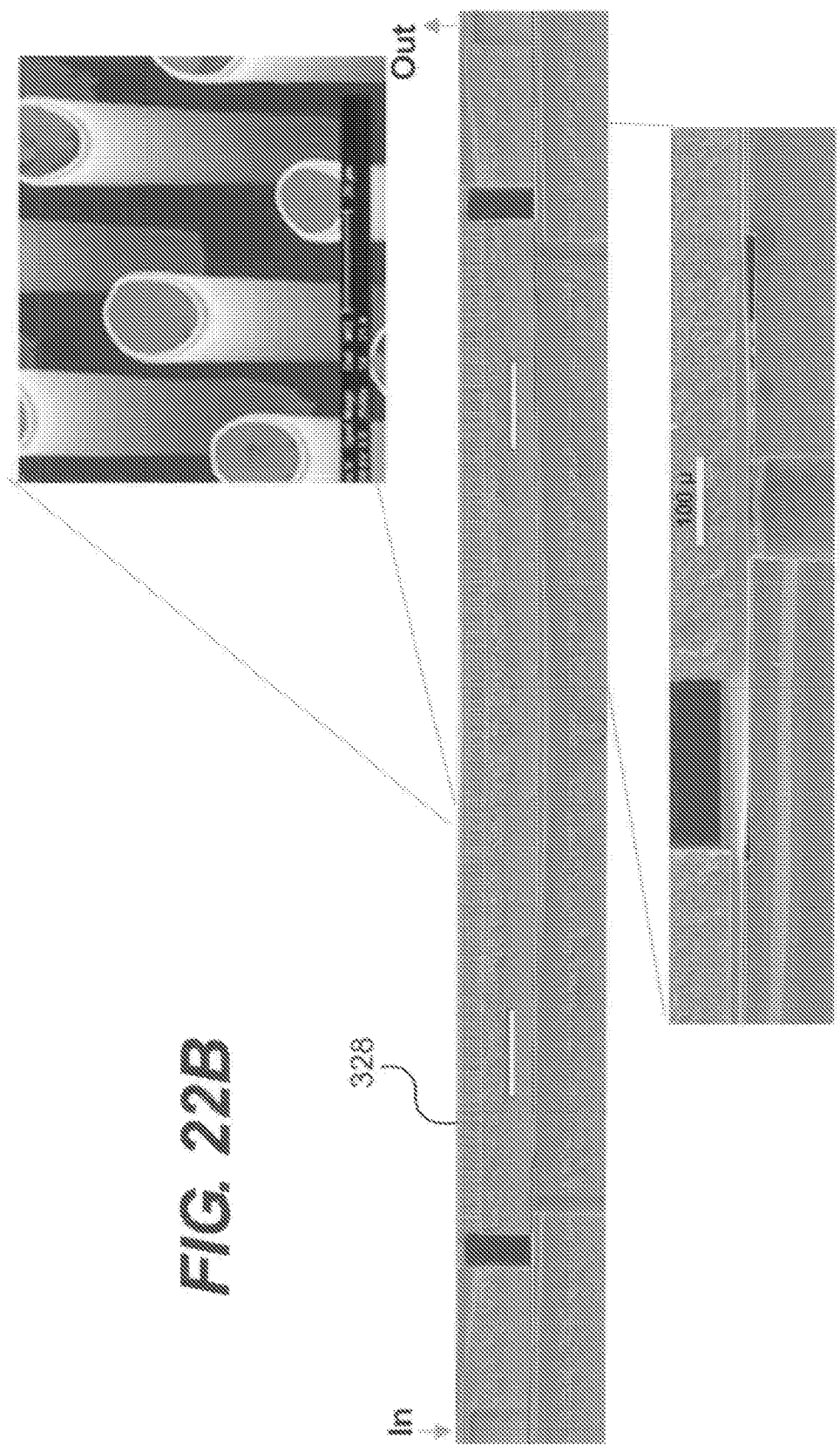

HIGH GAIN SELECTIVE METAL ORGANIC FRAMEWORK PRECONCENTRATORS

CROSS-REFERENCE TO RELATED APPLICATIONS

This application claims priority under 35 U.S.C. §119(e) to U.S. Provisional Patent Application No. 60/724,313, filed on Oct. 6, 2005, U.S. Provisional Patent Application No. 60/791,988, filed on Apr. 14, 2006, and U.S. Provisional Patent Application No. 60/828,266, filed Oct. 5, 2006, the disclosures of which are expressly incorporated by reference herein in their entirety.

STATEMENT REGARDING FEDERALLY-SPONSORED RESEARCH/DEVELOPMENT

This invention was made, at least in part, with U.S. government support under U.S. Air Force Grant No. FA8650-04-1-7121, awarded by the Defense Advanced Research Projects Agency (DARPA), and under NSF Grant No. DMI 03-28162 and NSF Grant No. CTS 01-20978, awarded by the National Science Foundation. The U.S. government may have certain rights in the invention.

BACKGROUND OF THE INVENTION

1. Field of the Invention

The invention generally relates to analyte collection and is useful, for example, in analyte detection and analysis systems and methods. In particular, the invention concerns preconcentrators, which are used in a wide variety of collection and analysis systems, and the use of metal organic framework molecules as sorbents in preconcentrators or similar devices, including particularly portable micropreconcentrators.

2. Related Art

A preconcentrator is a device that is used to collect a sample for analysis of particular constituents in the sample called analytes. A preconcentrator is particularly useful in detecting analytes that are present in very low concentrations in a sample. For example, a preconcentrator may be used in combination with a detection device to collect a sample, thereby increasing its concentration, before transferring it to a detector for analysis of analytes of interest. As a low-concentration sample gas containing a mixture of compounds passes through a preconcentrator, compounds are captured and sorbed by the preconcentrator over time. During preconcentration, the concentration of the analyte may increase by up to over 1000 times the original concentration of the analyte in the sample. The captured compounds are then desorbed, passed out of the preconcentrator, and conducted to the detector for analysis.

For example, a preconcentrator may be used with a gas chromatograph (GC), a vital instrument used to analyze complex compound mixtures in a variety of environments including clinical, aerospace, military, process control, and other applications. A preconcentrator is required in high performance GC systems because the resolving power of the GC column or the sensitivity of the sensor is often limited by the low ppb (part-per-billion) concentrations of analytes with a wide range of volatility. When connected to a GC, a discrete sample is first captured in the preconcentrator and then thermally desorbed to a polymer-coated separation column in the GC. The sample is then eluted down the column under a positive pressure of an inert carrier gas to the detector. Separation of the components of the sample by differential partitioning along the column, which is typically ramped to an elevated temperature range during the analysis, permits the identification and quantification of the components of the sample by their retention times and response profiles. The separated components are subsequently detected and recorded in a detector. Preconcentration increases the sensitivity of the detector by concentrating dilute samples that would normally not be detected.

Capillary-tube preconcentrators are conventionally used in GCs. Such preconcentrators include a stainless-steel or glass capillary tube packed with one or more granular sorbent materials. These preconcentrators are typically large in size and have significant power requirements, and as a result, the GC systems they are used with are not portable. This makes conventional GCs practically impossible to use in number of settings including subways, airports, and buildings where analysis of air samples must be performed on-site. These preconcentrators also suffer from large dead volume and limited heating efficiency due to their large thermal mass. In addition, conventional GC systems often have a long analysis cycle and require a large sampling volume. This makes them impractical for use in circumstances in which only a small sample is available for testing and rapid analysis is necessary.

Many efforts have gone into the development of portable micropreconcentrators that exhibit sufficiently high performance to be used in portable GC systems. So far, these portable systems have also been relatively large in size or weight (several kg) and have a large power requirement (tens-to-hundreds of Watts). Further, conventional micropreconcentrators have been unable to raise the concentration of dilute samples to a detectable range so that samples can be analyzed accurately. Thus, there are no commercially available fast preconcentrators that are small enough to fit into a microelectromechanical (MEMS) scale gas analysis system.

Common sorbents used in preconcentrators such as activated carbon, Tenax®, zeolites, carbon nanotubes, Carbopack®, Carbotrap®, Carbosieve®, Carboxen®, Chromosorb®, HayeSep®, silica gel, and glass beads also have several long-standing problems that make them unsuitable or undesirable for use in micropreconcentrators. For example, these sorbents do not have high enough sorption capacity or are not selective enough for specific analytes or and they cause low or incomplete desorption of analyte. In particular, it is known that many toxic gases decompose before they are desorbed from carbon-based sorbents. DB5 is another sorbent in which analytes interfere with each other and make detection difficult. In addition, these sorbents often have slow or incomplete desorption, which makes it very difficult to get accurate concentration readings.

Accordingly, there is a need for improved preconcentrators and, in particular, commercially viable micropreconcentrators, as well as sorbents that provide high gains in concentration of analytes, selective sorption of analytes, allow rapid and complete desorption of analytes, and have high sorption capacities. Further, the sorbent should have thermal stability of to temperatures of up to 300° C. to 400° C. and should not interfere with the sample gas or its analytes. In addition, micropreconcentrators should be compact in size so that they can be used with a portable analytical instrument and require only a small sample volume.

SUMMARY OF THE INVENTION

The invention meets the foregoing needs and overcomes the drawbacks and disadvantages of the prior art by providing for a new use of metal organic framework (MOF) molecules as sorbents in preconcentrators, which results in orders of magnitude improvement in the sensitivity in analyte detection in a detection device. The MOFs of the invention may be used in conventional micropreconcentrators with little structural changes. The invention also provides for new micropreconcentrators designs that are more compact and more sensitive through the use of microelectromechanical systems (MEMS) and other technologies that may use MOFs or other sorbents. While the use of MOFs as sorbents is particularly advantageous in micropreconcentrators, the principles of the invention may be used in larger preconcentrator designs with appropriate scale-ups made by the skilled artisan.

The invention may be implemented in a number of ways. Accordingly, in one aspect of the invention, metal organic frameworks (MOFs) are used as a sorbent of an analyte in a collection system. The collection system may include one of a preconcentrator, micropreconcentrator, personal respirator and dosimeter. The preconcentrator or micropreconcentrator may be a purge and trap system, microelectromechanical (MEMS) valve system, array of microstructures, dosimeter, disc, pellet, or swab. The preconcentrator or micropreconcentrator may include a MEMS valve system with at least 3 valves. In particular, the MEMS valve system may have 4 or 5 valves. The MOFs may have a thermal stability of up to about 300° C. to about 400° C. The MOFs also may sorb substantially all of the analyte. After sorbing the analyte, the MOFs may release the analyte, for example, by thermal desorption. The MOF may be in particular form or in a film. The MOF particles may have a diameter of between about 20 nanometers to about 500 microns, and, more particularly, a diameter of between about 100 nanometers to about 50 microns. The MOFs may include one or more of Zn-MOF1, Zn-MOF2, Zn-MOF3, Zn-MOF4, ZnMOF5, Cu-MOF1, Cu-MOF2, Tb-MOF1, Tb-MOF2, Cd-MOF1, Cd-MOF2, CdMOF3, Co-MOF1, Co-MOF2, Zn-MOF6, MOF-5, $Cu(4,4'-bpy)_{1.5}NO_3(H_2O)_{1.25}$, IRMOF2, $[Cu_3(TMA)2]_n$, $[Cu(OH)—(C_5H_4NCO_2]$, MOF-38, $Ag(4,4'-bpy)NO_3$, IRMOF3 and IRMOF7. The MOFs may be selective to a predetermined analyte or group of analytes. This selectivity may be enhanced by adjusting the pore size of the MOFs and adding a functional group to the MOFs. The MOFs may sorb analytes including explosives and chemical warfare agents in general and more particularly, analytes such as XV, sarin, DMMP, PMP, diethyl methylphosphonate (DEMP), diisopropyl methylphophonate (DIMP), dichlorohexane, malathion, acetic anhydride, TNT, and RDX.

According to another aspect of the invention, a method of concentrating an analyte in a sample includes using a sorbent to collect the analyte, wherein the sorbent has high sorption capacity, selective sorptivity, thermal stability at temperatures up to about 300° C. to about 400° C., a particle size range from about 20 nm to about 150 microns, and does not substantially decompose the analyte during sorption. The sorbent may include a metal organic framework (MOF) molecule, such as at least one of Zn-MOF1, Zn-MOF2, Zn-MOF3, Zn-MOF4, Zn-MOF5, Cu-MOF1, Cu-MOF2, Tb-MOF1, Tb-MOF2, Cd-MOF1, Cd-MOF2, Cd-MOF3, Co-MOF1, Co-MOF2, Zn-MOF6, MOF-5, $Cu(4,4'-bpy)_{1.5}NO_3(H_2O)_{1.25}$ IRMOF2, $[Cu_3(TMA)_2]_n$, $[Cu(OH)—(C_5H_4NCO_2]$, MOF-38, $Ag(4,4'-bpy)NO_3$, IRMOF3, and IRMOF7.

In yet another aspect of the invention, a micropreconcentrator includes a sorbent that is highly selective to an analyte or group of analytes. The sorbent may have a thermal stability of up to about 300° C. to about 400° C., and may include particles having a diameter of between about 20 nanometers to about 500 microns, and, more particularly, a diameter of between about 100 nanometers to about 150 microns. The sorbent may include a MOF. The sorbent may be adhered to an array of microstructures, such as microposts.

In yet another aspect of the invention, a system for collecting an analyte from a sample may include an inlet to receive the sample, a collection chamber containing at least one of i) a sorbent highly selective to the analyte and ii) an array of microstructures having a radius of a, and a half-spacing between microstructures of s, and wherein a dimensionless parameter, β, is defined as a/s such that flow through the collection chamber for β>0.65 substantially obeys the lubrication Stokes approximation of Navier-Stokes equation, and for β≦0.65 substantially obeys Oseen's approximation of Navier-Stokes equation, and an outlet to conduct the analyte out of the system. The sorbent may have high sorption capacity, thermal stability at temperatures up to about 300° C. to about 400° C., a particle size range from about 20 nm to about 500 microns, and does not substantially decompose the analyte. The sorbent may include one or more metal organic frameworks (MOFs). The system may further include at least one valve controlling the flow to or from the collection chamber. The system may be a micropreconcentrator and the valve may be a microelectromechanical (MEMS) valve. The system may include a purge and trap system and the collection chamber may include a groove in a rotary injection valve. The inlet may be coupled to a carrier gas containing the sample, and the analyte may be sorbed onto the sorbent in the collection chamber. The system may also include a release mechanism to desorb the analyte from the sorbent, such as a heater to heat the sorbent. The desorbed analyte may be conducted through the outlet. The outlet may be coupled with a detector. The detector may be coupled with an analytical device, such as a gas chromatograph, surface acoustic wave, evanescent wave detector, a piezoelectric detector, an ion mobility spectrometer, and a chemiresistor detector. The collection chamber may be coupled with a MEMS valve system having a plurality of electrodes and at least one membrane electrode operable to open and close the MEMS valves in a coordinated manner. The membrane electrode may be electrostatically actuated. The MEMS valve system may include at least three valves. The microstructures may be disposed within the collection chamber. The microstructures may be coated with a sorbent selective to the analyte. The sorbent may include one of a low surface area compound and a high surface area compound. The low surface area compounds may include polymers and the high surface area compounds may include MOFs. The microstructures may include generally cylindrical members, and may be arranged in a square array.

In yet another aspect of the invention, a method of collecting an analyte from a sample for analysis may include concentrating the analyte by sorbing it on a sorbent highly selective to the analyte, desorbing the analyte from the sorbent, and conducting the desorbed analyte to a device for analysis, such as a gas chromatograph, surface acoustic wave, evanescent wave, a piezoelectric detector, an ion mobility spectrometer, or a chemiresistor detector. The concentrating step may include using a sorbent having high selectivity to polar molecules, thermal stability at temperatures up to about 300° C. to about 400° C., a particle size range from about 20 nm to about 500 microns, and which does not substantially decompose the analyte during sorption. The sorbent may include a metal organic framework (MOF) molecule, which may be at least one of Zn-MOF1, Zn-MOF2, Zn-MOF3, Zn-MOF4, Zn-MOF5, Cu-MOF1, Cu-MOF2, Tb-MOF1, Tb-MOF2, Cd-MOF1, Cd-MOF2, Cd-MOF3, Co-MOF1, Co-MOF2, Zn-MOF6, MOF-5, $Cu(4,4'-bpy)_{1.5}NO_3(H_2O)_{1.25}$ IRMOF2, $[Cu_3(TMA)_2]_n$, $[Cu(OH)—(C_5H_4NCO_2]$, MOF-38, $Ag(4,4'-bpy)NO_3$, IRMOF3, and IRMOF7. The method may also include the step of at least one of adjusting the pore size of the MOF and adding a functional group to the MOF. The sorbent may fully sorb the analyte during the collecting step. After the desorbing step, the analyte may be fully released from the sorbent, e.g., by thermal desorption. The MOF may be in particular form or in a film. The analytes may include XV, sarin, DMMP, PMP, diethyl methylphosphonate (DEMP), diisopropyl methylphosphonate (DIMP), dichlorohexane, malathion, acetic anhydride, TNT, and RDX. The method may further include the step of synthesizing the sorbent to be selective to a predetermined group of analytes.

In yet a further aspect of the invention, a process for making a selectively sorbent MOF, Zn-MOF1, having a cubic crystalline structure with crystals in the range of 2 to 4 microns may include (a) dissolving 0.239 g of 4,4',4'',4'''-(21H, 23H-Porphine-5,10,15,20-tetrayl)tetrakis(benzoic acid) (H2TPP) and 0.18 g of $Zn(NO_3)_2 \cdot 6H_2O$ in 60 mL DEF; (b) stirring the dissolved solution; (c) sealing the dissolved solution in a closed vessel; and (d) heating the vessel to 100° C. at 2° C./minute. Zn-MOF1 may be made by following the above process.

In yet another aspect of the invention, a process for making a selectively sorbent MOF, Zn-MOF1, having a cubic crystalline structure with crystal sizes in the range from about 10 microns to about 30 microns may include (a) dissolving $Zn(NO_3)_2 \cdot 6H_2O$ (0.18 g, 0.605 mmol) and 4,4',4'',4'''-(21H, 23H-porphine-5-10-15-20-tetrayl)tetrakis(benzoic acid) (0.199 g, 0.252 mmol) in 10 mL diethylformamide; (b) sealing the dissolved solution, and (c) heating in a microwave oven. Zn-MOF1 may be made by following the above process.

In yet another aspect of the invention, a process for making a selectively sorbent MOF, Zn-MOF2, having a cubic crystalline structure with crystal sizes in the range from 2 to 4 microns may include (a) mixing $Zn(NO_3)_2 \cdot 6H_2O$ (0.1 g, 0.336 mmol) and 2-anilino-5-bromoterephthalic acid, (2-anilino-5-BrBDCH2) (0.0847 g, 0.252 mmol); (b) dissolving the mixture in 10 mL diethylformamide; (c) sealing the dissolved mixture; and (d) heating in a microwave oven. Zn-MOF2 may be made by following the above process.

In yet another aspect of the invention, a process for making a selectively sorbent MOF, Zn-MOF3, having a cubic crystalline structure with crystals ranging from 4 to 7 microns, may include (a) mixing $Zn(NO_3)_2 \cdot 6H_2O$ (0.15 g, 0.504 mmol) with 2-trifluoromethoxy terephthalic acid, (2-trifluoromethoxy-BDCH2) (0.0946 g, 0.378 mmol); (b) dissolving the mixture in 10 mL diethylformamide; (c) sealing the dissolved mixture; and (d) heating the dissolved mixture in a microwave oven. Zn-MOF3 may be made by following the above process.

In yet another aspect of the invention, a process for making a selectively sorbent MOF, Zn-MOF4, having crystals of irregular shape may include (a) mixing $Zn(NO_3)_2 \cdot 6H_2O$ (0.1 g, 0.336 mmol) with nitroterephthalic acid (0.0532 g, 0.252 mmol); (b) dissolving the mixture in 10 mL diethylformamide, sealing the dissolved mixture; and (c) heating the dissolved mixture in a microwave oven. Zn-MOF4 may be made by following the above process.

In yet another aspect of the invention, a process for making a selectively sorbent MOF, Zn-MOF5, may include (a) mixing $Zn(NO_3)_2 \cdot 6H_2O$ (0.15 g, 0.504 mmol) with cis-cyclobutane-1,2-dicarboxylic acid (0.0545 g, 0.378 mmol); (b) dissolving the mixture in 10 mL diethylformamide; (c) sealing the dissolved mixture; and (d) heating the dissolved mixture in a microwave oven. Zn-MOF5 may be made by following the above process.

In yet another aspect of the invention, a process for making a selectively sorbent MOF, Cu-MOF1, may include (a) mixing $Cu(NO_3)_2 \cdot 2.5H_2O$ (0.15 g, 0.645 mmol) with 2,5-thiophenedicarboxylic acid (0.0833 g, 0.484 mmol); (b) dissolving the mixture in 10 mL diethylformamide (c) sealing the dissolved mixture; and (d) heating the dissolved mixture in a microwave oven. Cu-MOF1 may be made by following the above process.

In yet another aspect of the invention, a process for making a selectively sorbent MOF, Cu-MOF2, may include (a) mixing $Cu(NO_3)_2 \cdot 2.5H_2O$ (0.1 g, 0.430 mmol) with 2-(trifluoromethoxy)terephthalic acid (2-trifluoromethoxy-$BDCH_2$) (0.0807 g, 0.322 mmol); (b) dissolving the mixture in 10 mL diethylformamide; (c) sealing the dissolved mixture; and (d) heating the dissolved mixture in a microwave oven. Cu-MOF2 may be made by following the above process.

In yet another aspect of the invention, a process for making a selectively sorbent MOF, Tb-MOF1, having a rod-shaped crystalline structure, may include (a) mixing $Tb(NO_3)_3 \cdot 5H_2O$, (0.1 g, 0.230 mmol), with terephthalic acid (BDC) (0.0286 g, 0.172 mmol); (b) dissolving the mixture in 10 mL diethylformamide; (c) sealing the dissolved mixture; and (d) heating the dissolved mixture in a microwave oven. Tb-MOF1 may be made by following the above process.

In yet another aspect of the invention, a process for making a selectively sorbent MOF, Tb-MOF2, may include (a) mixing $Tb(NO_3)_3 \cdot 5H_2O$, (0.1 g, 0.230 mmol), with 2,5-thiophenedicarboxylic acid (0.0297 g, 0.172 mmol); (b) dissolving the mixture in 10 mL diethylformamide; (c) sealing the dissolved mixture; and (d) heating the dissolved mixture in a microwave oven. Tb-MOF2 may be made by following the above process.

In yet another aspect of the invention, a process for making a selectively sorbent MOF, Cd-MOF1, may include (a) mixing $Cd(NO_3)_2 \cdot 4H_2O$, (0.1 g, 0.324 mmol), with cis-cyclobutane-1,2-dicarboxylic acid (0.0350 g, 0.243 mmol); (b) dissolving the mixture in 10 mL diethylformamide; (c) sealing the dissolved mixture; and (d) heating the dissolved mixture in a microwave oven. Cd-MOF1 may be made by following the above process.

In yet another aspect of the invention, a process for making a selectively sorbent MOF, Cd-MOF2, may include (a) mixing $Cd(NO_3)_2 \cdot 4H_2O$ (0.1 g, 0.324 mmol) with nitroterephthalic acid (0.0456 g, 0.216 mmol); (b) dissolving the mixture in 15 mL diethylformamide; (c) sealing the dissolved mixture; and (d) heating the dissolved mixture in a microwave oven. Cd-MOF2 may be made by following the above process.

In yet another aspect of the invention, a process for making a selectively sorbent MOF, Cd-MOF3, may include (a) mixing $Cd(NO_3)_2 \cdot 4H_2O$ (0.1 g, 0.324 mmol) with terephthalic acid (0.0404 g, 0.243 mmol); (b) dissolving the mixture in 10 mL diethylformamide; (c) sealing the dissolved mixture; and (d) heating the dissolved mixture in a microwave oven. Cd-MOF3 may be made by following the above process.

In yet another aspect of the invention, a process for making a selectively sorbent MOF, Co-MOF1, may include (a) mixing $Co(NO_3)_2 \cdot 6H_2O$, (0.1 g, 0.343 mmol), with terephthalic acid (0.0428 g, 0.258 mmol); (b) dissolving the mixture in 10 mL diethylformamide; (c) sealing the dissolved mixture; and (d) heating the dissolved mixture in a microwave oven. Co-MOF1 may be made by following the above process.

In yet another aspect of the invention, a process for making a selectively sorbent MOF, Co-MOF2, may include (a) mixing $Co(NO_3)_2 \cdot 6H_2O$, (0.1 g, 0.343 mmol) with 1,3,5-benzenetricarboxylic acid (0.0542 g, 0.258 mmol); (b) dissolving the mixture in 10 mL diethylformamide; (c) sealing the mixture; and (d) heating in a microwave oven. Co-MOF2 may be made by following the above process.

In yet another aspect of the invention, a process for making a selectively sorbent MOF, Zn-MOF6, may include (a) mixing $Zn(NO_3)_2*6H_2O$ (0.05 g, 0.168 mmol) with 3,3-bis(trifluoromethyl)-1-oxo-5-isobenzofurancarboxylic acid (0.0396 g, 0.126 mmol); (b) dissolving the mixture in 7 mL diethylformamide/3 mL $H_2O$; (c) sealing the dissolved mixture; and (d) heating the dissolved mixture in a microwave oven. Zn-MOF6 may be made by following the above process.

In yet a further aspect of the invention, a system for collecting an analyte from a sample may include (a) an inlet to receive the sample; (b) a collection chamber containing a sorbent; and (c) a series of at least three valves to control flow of the sample through the system. The series of valves may be microelectromechanical system (MEMS) valves and may include four or five valves.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and the various ways in which it may be practiced. In the drawings:

FIG. 5A shows the difference in signal over time when MOF-5 is used to sorb 2434 ppb dodecane vapor in helium gas. FIG. 5B shows a similar graph when the analyte is 642 ppb DMMP vapor in helium gas;

FIGS. 13 and 14 schematically illustrate the loading and operation of a micropreconcentrator in the form of a purge and trap system with a modified rotor design containing MOFs according to the principles of the invention;

FIG. 22A is a cross-sectional view of a micropreconcentrator constructed according to the principles of the invention housing a MEMS valve system incorporating microposts in the collection chamber; and FIG. 22B is an SEM photograph that provides an enlarged view of the microposts present in the collection chamber.

DETAILED DESCRIPTION OF THE INVENTION

Figure 1:
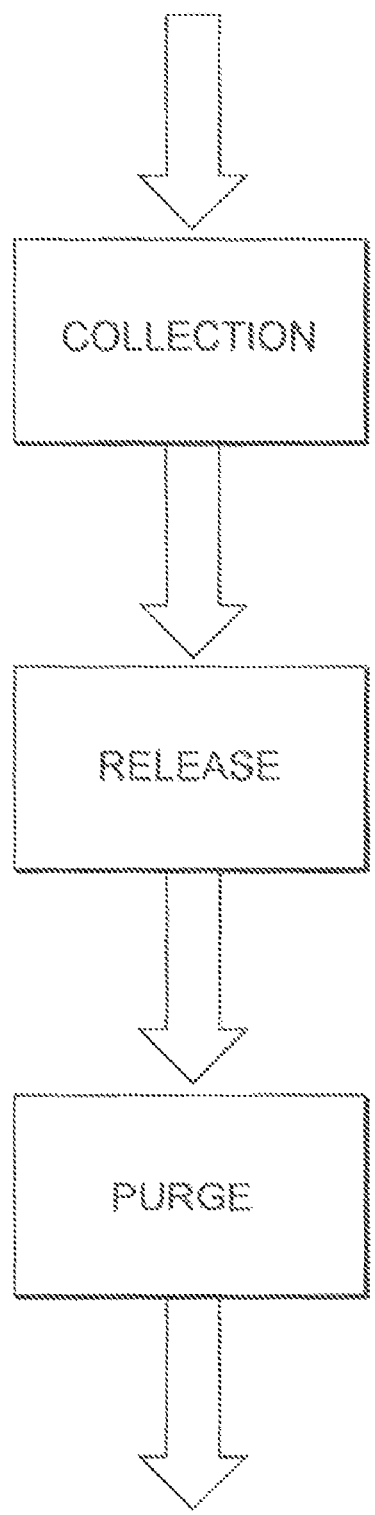
FIG. 1 is a flow chart depicting the basic functional steps carried out by a typical preconcentrator.

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law.

Moreover, it is noted that like reference numerals represent similar parts throughout the several views of the drawings. It is understood that the invention is not limited to the particular methodology, protocols, devices, apparatus, materials, and reagents, etc., described herein, as these may vary. It is also to be understood that the terminology used herein is used for the purpose of describing particular embodiments only, and is not intended to limit the scope of the invention. It must be noted that as used herein and in the appended claims, the singular forms "a," "an," and "the" include plural reference unless the context clearly dictates otherwise. Thus, for example, a reference to "a MOF" is a reference to one or more MOFs and equivalents thereof known to those skilled in the art and so forth.

Moreover, provided immediately below is a "Definition" section, where certain terms to the invention are defined specifically for clarity and consistent with the broadest meaning that would be attributed to these terms by an ordinarily skilled artisan. Particular methods, devices, and materials are described, although any method and materials or equivalents to those described herein may be used in the practice or testing of the invention. All references cited herein are incorporated by reference herein in their entirety. Words not specifically defined are to be accorded the definition as would be understood by a person skilled in the art consistent with the specification.

Definitions

The term, "preconcentrator" refers to a device that is operable to collect, remove, and/or concentrate a trace component and/or an analyte from a gas or liquid stream. As used herein, preconcentrators include micropreconcentrators, which refer to a preconcentrator that is small enough to be readily portable and capable of being carried by a person from site to site. Preconcentrators and micropreconcentrators may be used in conjunction with analytical instruments and devices.

The term "analyte" refers to a substance which a laboratory or other entity seeks to detect and/or identify using analytical procedures or other techniques.

The term "metal-organic framework" (MOF) refers to a one, two, or three dimensional polymer including both organic and metal or metal oxide structural units, where at least one of the metal units is bonded to least one bi-, tri- or poly-dentate organic unit.

The term "adsorption" refers to the adhesion of an extremely thin layer of atoms, molecules, or ions to the surfaces of solid bodies or liquids with which they are in contact.

The term "absorption" refers to a physical or chemical process by which atoms, molecules, or ions enter the volume of a bulk phase material.

The term "sorption" is used in its broadest sense to refer to the total effect of atoms, molecules, or ions being incorporated into a material's volume, and/or of atoms, molecules, or ions adhering to a material's surface by any mechanism, including, but not limited to adsorption and absorption.

The term "sorbent" also is used in its broadest sense to refer to a material that incorporates atoms, molecules, or ions into its volume and/or adheres atoms, molecules, or ions to its surface by "sorption" as defined above.

The term "desorption" refers to a process by which a sorbed material is released from its "sorbent."

The term "highly selective" refers to at least about 100 times greater selectivity of a sorbent to a desired analyte in a sample, compared to another substance in the sample being analyzed.

As described earlier, a preconcentrator functions by collecting a sample and raising the concentration of certain analytes of interest that are present in the sample. When used with an analytical instrument such as a GC, this increase in concentration of analytes, referred to herein as "gain," allows a detector to more accurately sense the analytes.

Common examples of preconcentrators include purge and trap devices used in the front end of analytical instruments, dosimeters used to measure exposure to chemicals, toxins and other components, sample tubes used to collect samples for analysis of air, water, breath, urine, or blood. Further, gas masks and other protective clothing may function as preconcentrators in that they collect and remove trace compounds.

FIG. 1 is a flowchart depicting the basic functional steps carried out by a typical preconcentrator. As shown in FIG. 1, the first step involves collection of a sample containing an analyte in the preconcentrator. For example, the analyte may be collected by sorption on a chemical sorbent contained in the preconcentrator. In the second step, the analyte is released from the preconcentrator. When used with a sorbent, this release may be accomplished by desorbing the analyte from the sorbent. For example, the sorbent may be heated to desorb the analyte. Finally, in step three, the sample and analyte are purged from the preconcentrator and conducted to the detector of an analytical instrument such as a GC, for analysis. The preconcentrator may be purged, for example, by flushing a carrier gas through the preconcentrator.

This invention provides new ways to collect and release the analyte, as set forth in steps 1 and 2 and novel micropreconcentrator designs in which these steps may be carried out. The micropreconcentrators of the invention may include a high surface area sorbent to selectively sorb analytes. In particular, Applicants discovered that metal-organic framework (MOF) molecules, which are a known, but relatively new class of compounds, may be used as sorbents in preconcentrators.

MOFs have been the focus of intense activity in recent years because of their extremely high porosity and tailorable molecular cavities. MOFs have been studied for a variety of applications including hydrogen storage, selective sorption, non-linear optical materials, and as catalysts e.g., catalysts to store $H_2$ (in fuel cells) or $CO_2$. Applicants have discovered that MOFs have properties that make them highly advantageous as preconcentrators including, for example, high sorption capacity due to their high surface area, high selectivity to specific analytes, inert nature which does not decompose the analyte, thermal stability, and result in unexpectedly high gains in detection, which will be described in detail later.

Accordingly, in one aspect of the invention, MOFs are used in the collection step of FIG. 1 to selectively sorb specific analytes in a preconcentrator. For example, MOFs may be used in particle form, or they may be incorporated into a film inside the preconcentrator. Once the analytes are fully sorbed by the MOFs, the analytes are released in the second step of FIG. 1, e.g., by thermal desorption. Then, they can be purged and transferred from the preconcentrator to a detector, for example. The structure and properties of MOFs that make them highly suitable for use as selective sorbents in preconcentrators are discussed below.

Figure 2:
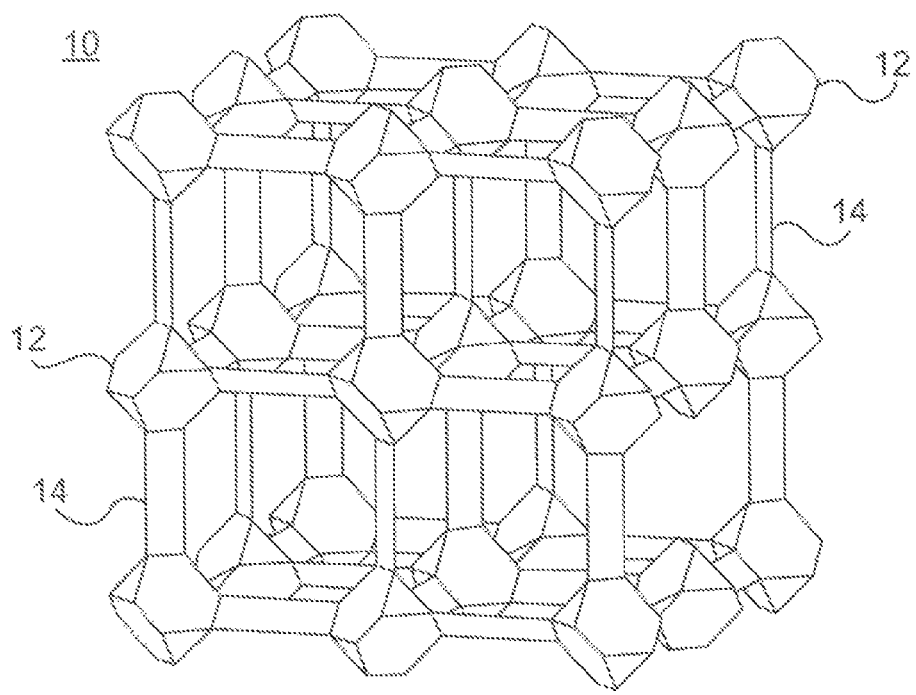
FIG. 2 is a diagram showing a typical crystalline structure of a MOF.
Figure 3:
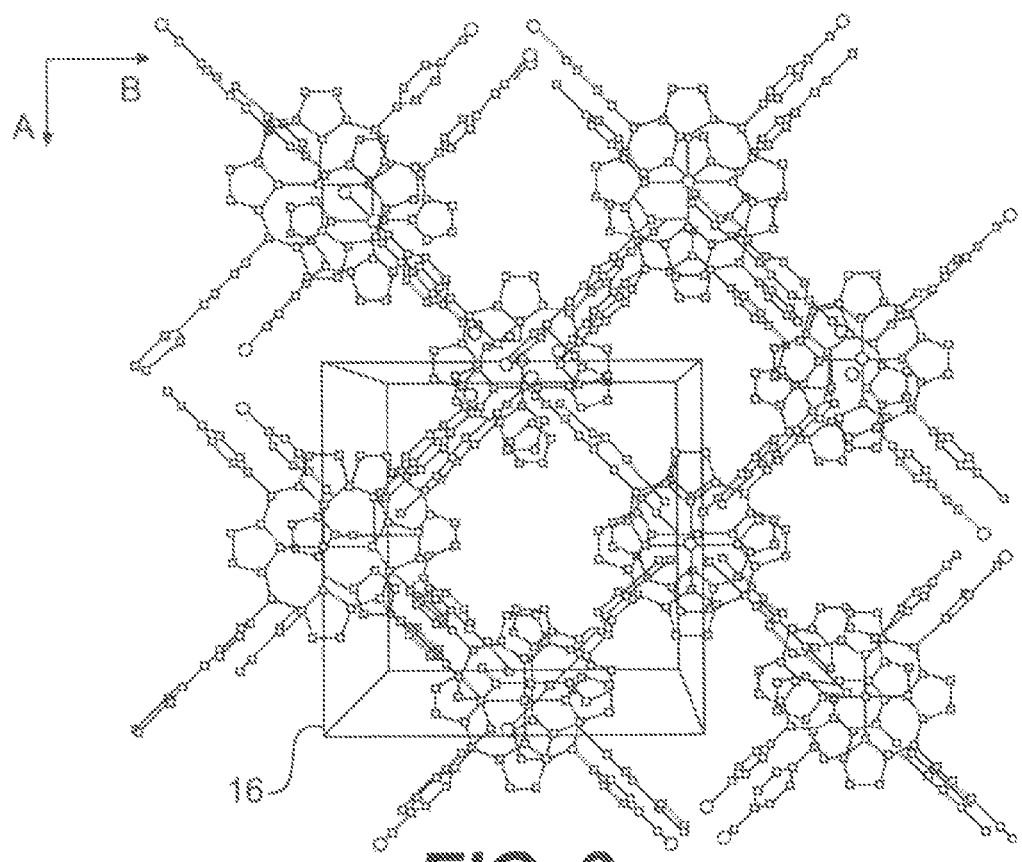
FIG. 3 is a view of the structure and channels of a specific MOF, Zn-MOF1, constructed according to the principles of the invention.

MOFs are organometallic structures with high surface area and tailorable selectivity, which makes them suitable for sorption of selected molecules. They have a cubic crystalline structure that is formed by copolymerization of metals or metal oxides with organic ligands. FIG. 2 is a diagram of a typical MOF's crystalline structure 10 including metal or metal oxides, here shown as polyhedrons 12, having polymer ligands 14 extending between them. This highly ordered structure facilitates the creation of interior pores and channels. MOFs are known to have 1-3 nanometer (nm) pores. FIG. 3 is a view of the structure and channels 16 of one of the new MOFs discovered by Applicants and disclosed herein, Zn-MOF-1. As shown in FIG. 3, Zn-MOF-1 has channels 16 of about 10 Å×10 Å. MOF crystals are known to have an average diameter of 200 microns.

The surfaces of MOFs' pores and channels increase the overall surface areas of MOFs and allow them to sorb analytes in the collection step of FIG. 1. MOFs have high porosity which is comparable to or larger than that of zeolites. For example, MOF-5, a known MOF, may have a surface area of about 2900 $m^2/g$ and IRMOF-177 may have a surface area of about 4500 $m^2/g$. The very high surface area of MOFs thus results in MOFs having very high sorption capacities, which makes them desirable candidates for use in preconcentrators.

Experiments performed by Applicants determined the sorption capacity of certain MOFs. For example, the sorption capacity of MOF-5 was measured using thermal gravimetric analysis (TGA). In order to perform TGA, MOF-5 crystals, prepared as described in Example 18 below, were first ground to a mesh size of less than 120 mesh. The crystals were then evacuated in vacuum at 150° C. for one day. Five milligrams of the ground MOF-5 was packed into a 3 mm GC capillary with glass wool. DMMP vapor was carried by 15 sccm of He gas through a saturator at room temperature (which is 107 ppm) and then passed through the sample capillary at 50° C. After 10 μL of solvent loss was observed from the saturator, the samples removed from the system. TGA was then carried out on a Perkin-Elmer TGA7 instrument heating from 25° C. to 300° C. at 10° C./min.

Figure 4:
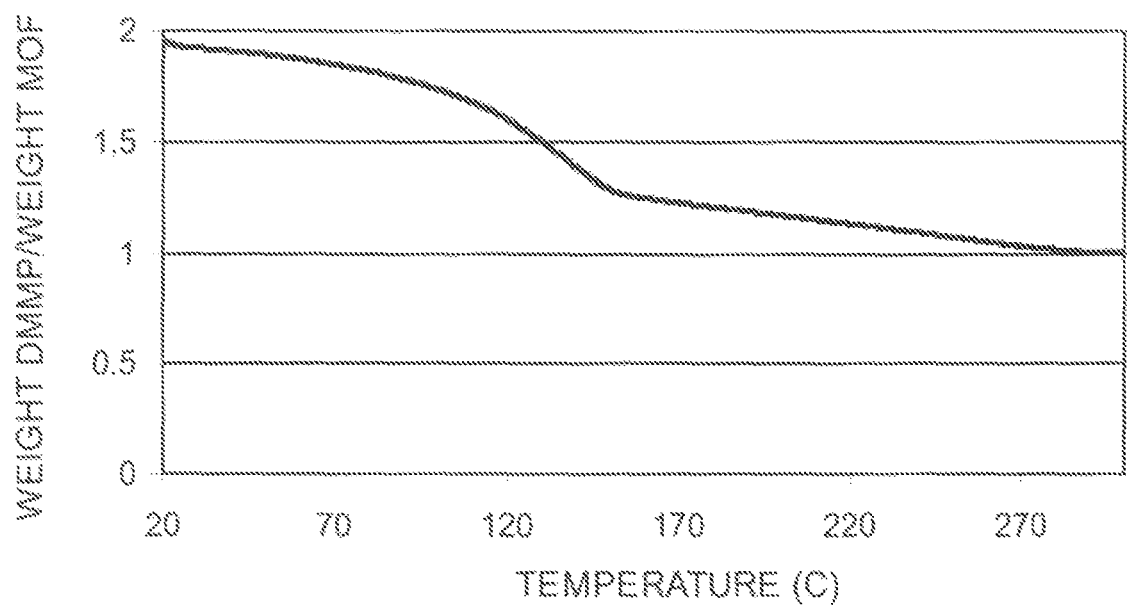
FIG. 4 is a graph of the ratio of the weight of an analyte (dimethyl methylphosphonate, DMMP) to the weight of MOF-5, used as a sorbent in a micropreconcentrator, as a function of temperature.

FIG. 4 is a graph of the ratio of the weight of dimethyl methylphosphonate, DMMP, a substance of interest for detection, to the weight of MOF-5 as a function of temperature, according to the TGA measurement described above. As shown in FIG. 4, at 20° C., MOF-5 has tremendous sorption capacity as it is able to sorb almost its own weight of DMMP. The MOF-5 became saturated when the DMMP concentration in the MOF-5 was about 0.7 $g/cm^3$. This compares to a gas phase density at room temperature of $6\times10^{-7}$ $g/cm^3$. Thus, MOF-5 raised the DMMP concentration by about $10^6$ in the preconcentrator.

Figure 5A:
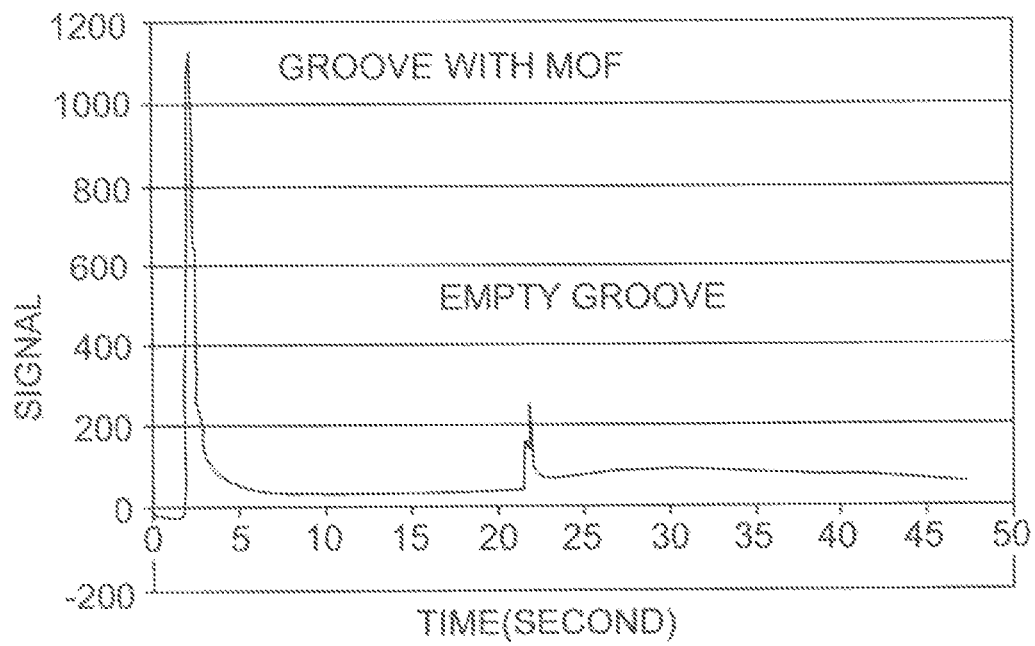
FIGS. 5A and 5B are graphs demonstrating the sorptivity of MOFs as being selective to a polar molecule.
Figure 5B:
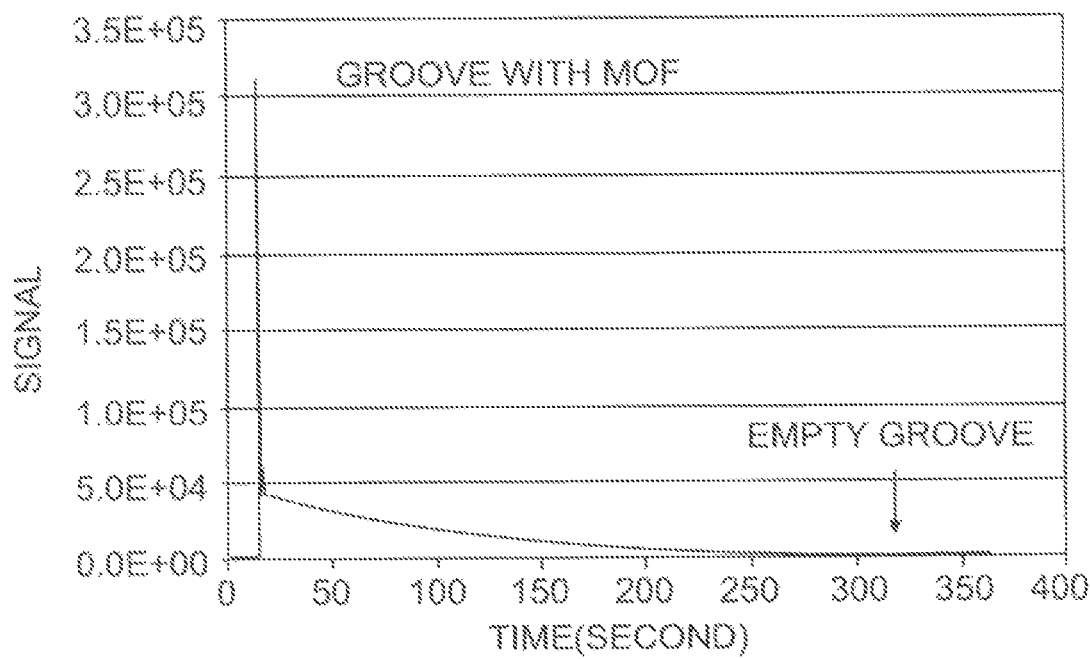

Further, MOFs are highly advantageous for use in preconcentrators because of their highly selective sorptivity. In particular, MOFs selectively sorb polar compounds. Although the mechanism for this selectivity is currently unknown, the details of the mechanism are not necessary to practice the invention. FIGS. 5A and 5B demonstrate the highly selective sorptivity of MOFs to a polar molecule measured using a modified purge and trap preconcentrator similar to that shown in FIGS. 13 and 14 discussed below.

FIG. 5A shows the difference in signal over time between when a MOF-5, synthesized as described below in Example 16, is used to sorb 2434 ppb dodecane vapor in helium gas, designated as "groove with MOF" and when no MOF-5 is used, designated as "empty groove." Dodecane, a non-polar molecule, exhibits limited improvements in gain when used with MOF-5 and Zn-MOF-1. According to FIG. 5A, when MOF-5 is used, a signal of 1150 is generated by the detector. When no MOF-5 is used, a signal of 275 is generated by the detector. Thus, the gain for dodecane is only about 4.2 (~1150/275).

FIG. 5B is a graph similar to FIG. 5A that shows the signal when the analyte is 642 ppb DMMP vapor in helium gas. As shown in FIG. 5B, MOF-5 markedly raises the concentration of DMMP and results in a gain of about 10,000. Thus, although almost 4 times (=2434/642) more dodecane than DMMP was used in these experiments, the selectivity of MOF-5 to polar molecules resulted in a much higher gain of about 10,000 for DMMP than the gain for dodecane of about 4.2.

Selective sorption in MOFs is significantly better than in previous sorbents, such as activated carbon, which sorb a wide variety of compounds and do not allow a specific analyte to be isolated. Moreover, MOFs may be selectively tailored to detect to specific compounds, which is particularly useful when trying to isolate a particular analyte. For example, the pore size may be adjusted by replacing a dicarboxylic ligand with one, two or three benzene rings in a row, so that the sorbent is size-selective. Also specific functional groups may be attached to the sorbent. For example, a $(CF_3)O$ functional group may be added to repel water and yet bind analytes of interest.

Figure 6:
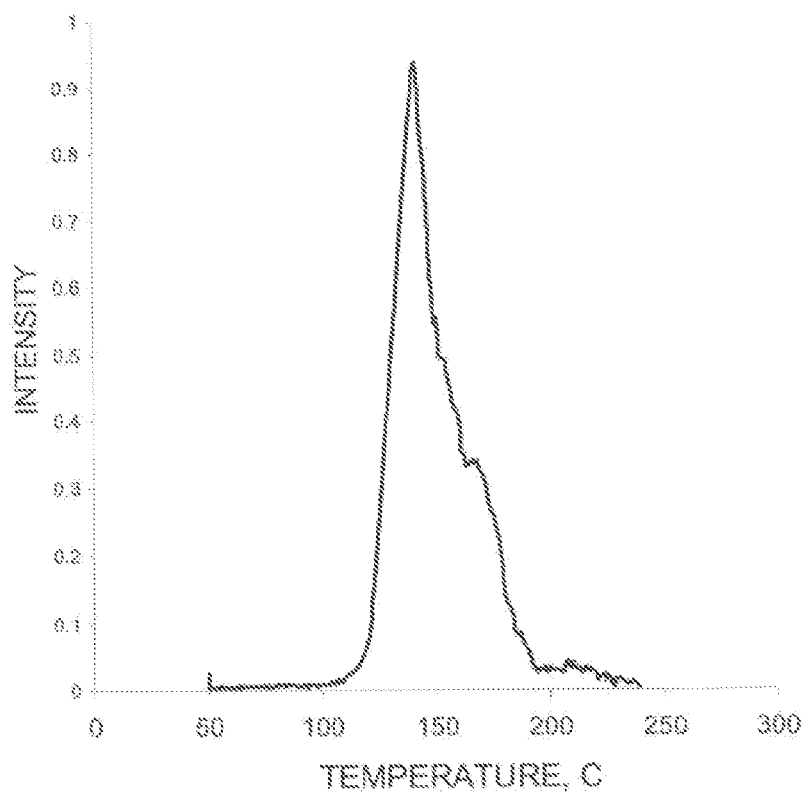
FIG. 6 is a graph that shows the desorption of DMMP from MOF-5 as a function of temperature.

As described above in the release step in FIG. 1, the analyte may be released from the MOF in the preconcentrator by desorption. Desorption of the analyte from the MOF is typically achieved by heating the preconcentrator and sorbent to release the sorbed analyte. Other methods of desorption include vacuum and electron or photon stimulated desorption. FIG. 6 is a graph that shows the thermal desorption of DMMP from MOF-5 as a function of temperature. As shown in FIG. 6, substantially all of the sorbed analyte is desorbed by 230° C.

Figure 7:
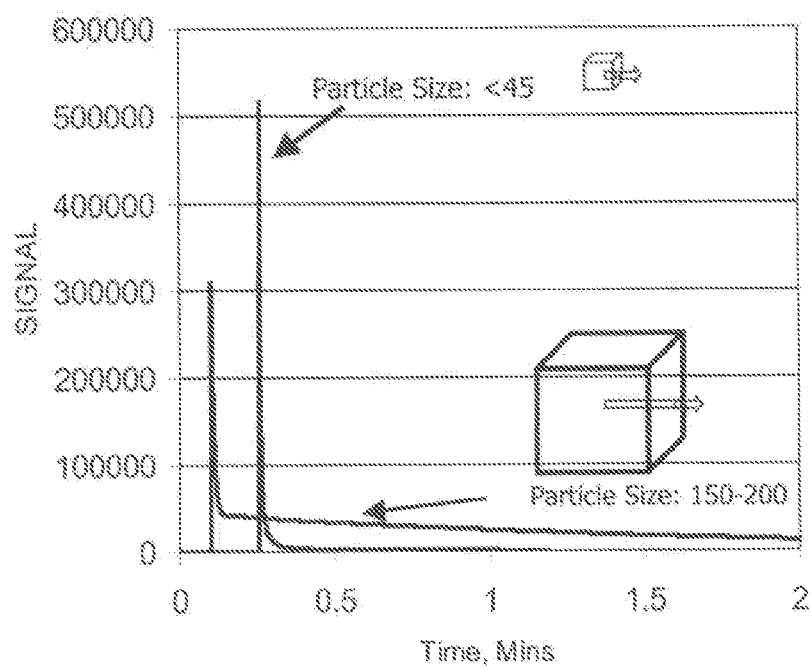
FIG. 7 is a graph that shows the desorption speed of DMMP from MOF-5 of two different particle sizes.

Experiments conducted by Applicants have shown that smaller MOF particles allow faster desorption of sorbed analytes. FIG. 7 is a graph showing the desorption speed of DMMP from MOF-5 particles of two different sizes, <45 μm and 150-200 μm, as measured in the purge and trap system illustrated in FIGS. 13 and 14. In the experiment, the DMMP concentration was 642 ppb and the sampling volume was 10 $cm^3$. As shown in FIG. 7, the MOF-5 particles with a particle size of <45 μm exhibited a sharp peak that started at about 15 seconds and did not taper off much beyond 30 seconds. In contrast, the desorption peak for the 150-200 μm size MOF-5 particles started well before the 45 μm particles (about 9-10 seconds), but the peak was much shorter and it tapered off for longer than 2 minutes. This indicates that mass transfer in the larger MOF particles is much slower. These results confirm that the use of smaller MOF particles in a preconcentrator is preferable because faster desorption allows faster detection of the sample.

Initial observations indicate that for optimal results in the preconcentrators of the invention, MOF particles with a diameter of about 20 nanometers to about 500 microns may be used, preferably between about 20 nanometers and about 150 microns, and more preferably between about 100 nanometers and about 50 microns. If the MOF particles are much smaller than about 100 nanometers, the structures tend to collapse tend to cluster in the preconcentrator, leading to poor mass transfer. Particles larger than about 50 microns give tailing during desorption, as shown in FIG. 7. Particles with diameters in the range of about 1 to about 10 microns have been observed to provide favorable results.

Figure 8:
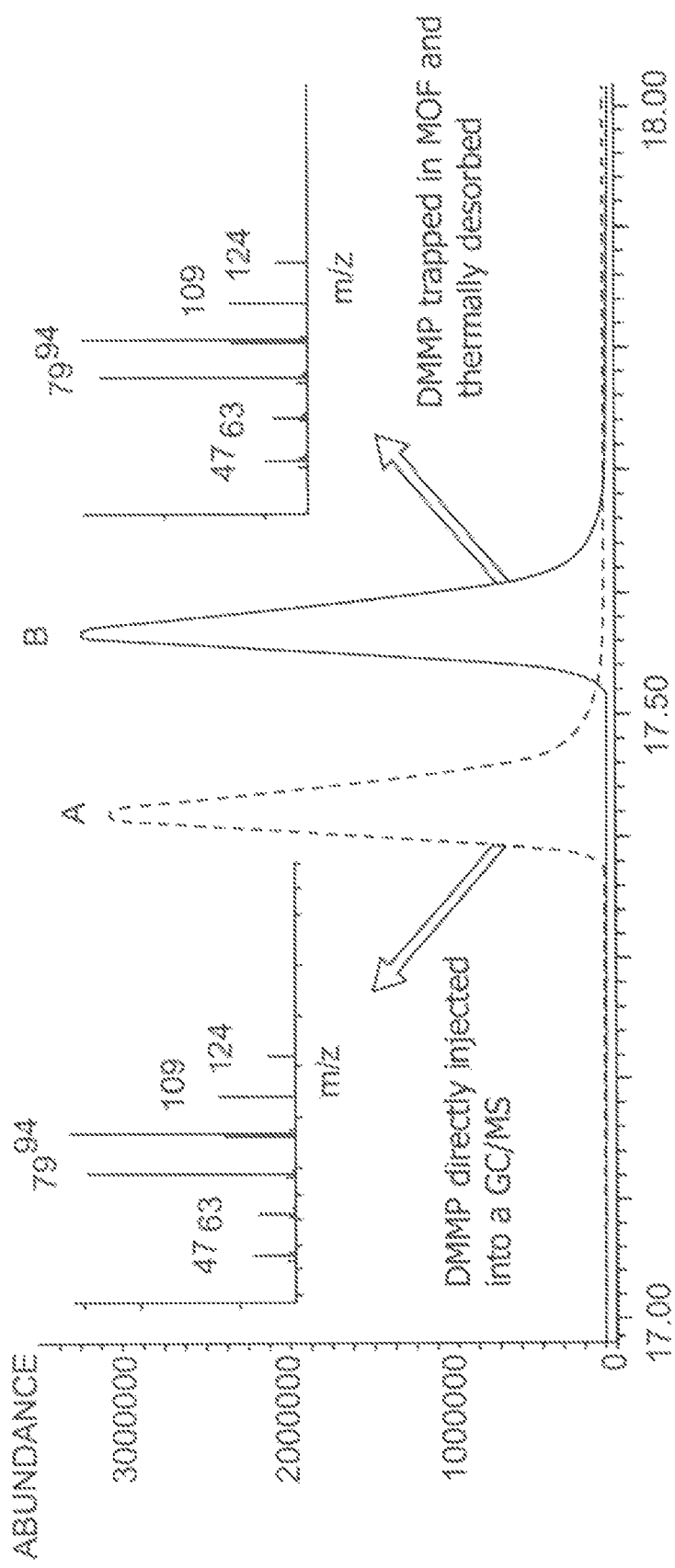
FIG. 8 is a graph depicting the results of a breakdown test in which a signal was obtained by directly injecting DMMP into a GC/MS and another signal was obtained by trapping DMMP in MOF-5 and desorbing it according to the invention.
Figure 13:
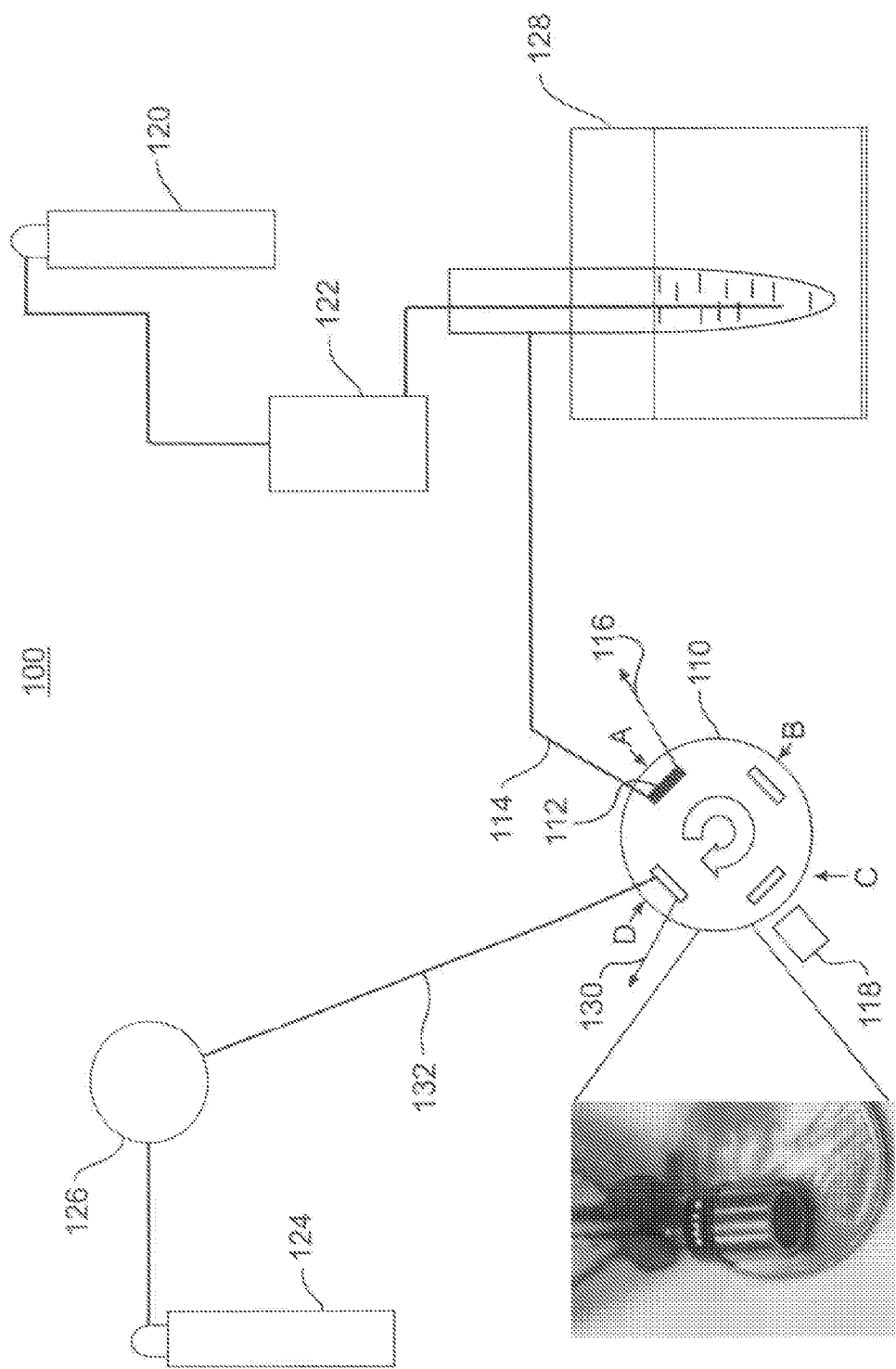

Further, tests of various MOFs conducted by Applicants using MOF-5 and Zn-MOF-1 in the modified purge and trap system shown in FIGS. 13 and 14 demonstrated that MOFs do not decompose analyte while sorbing or desorbing them. FIG. 8 is a graph depicting the results of a breakdown test of DMMP during desorption from MOF-5. Peak A and the corresponding mass spectrometer (MS) peaks follow from a direct injection of DMMP into the GC and MS. These peaks coincide well with Peak B and the corresponding MS peaks that follow from a sample in which DMMP was trapped in a MOF and then thermally desorbed. This test demonstrates that MOF-5 did not alter the DMMP molecules as it was sorbed and thermally desorbed on the MOF's surface. Similar results were obtained with similar tests using Zn-MOF-1. This property of MOFs is important for accurate detection of an analyte because if the MOF altered the analyte, the sample could not be analyzed accurately by the GC or MS.

In addition to not decomposing an analyte, MOFs themselves do not decompose at relatively high temperatures. Specifically, MOFs have thermal stability up to temperatures of about 300° C. to about 400° C. For example, PIZA-1 MOF begins to decompose at 375° C., MOF-5 is thermally stable up to 350° C., and Zn-MOF-1 is thermally stable up to 400° C. Having thermal stability up to high temperatures allows use of MOFs in preconcentrators, which are often heated to high temperatures (above 200° C.) during thermal desorption.

Figures 9A, 9B:
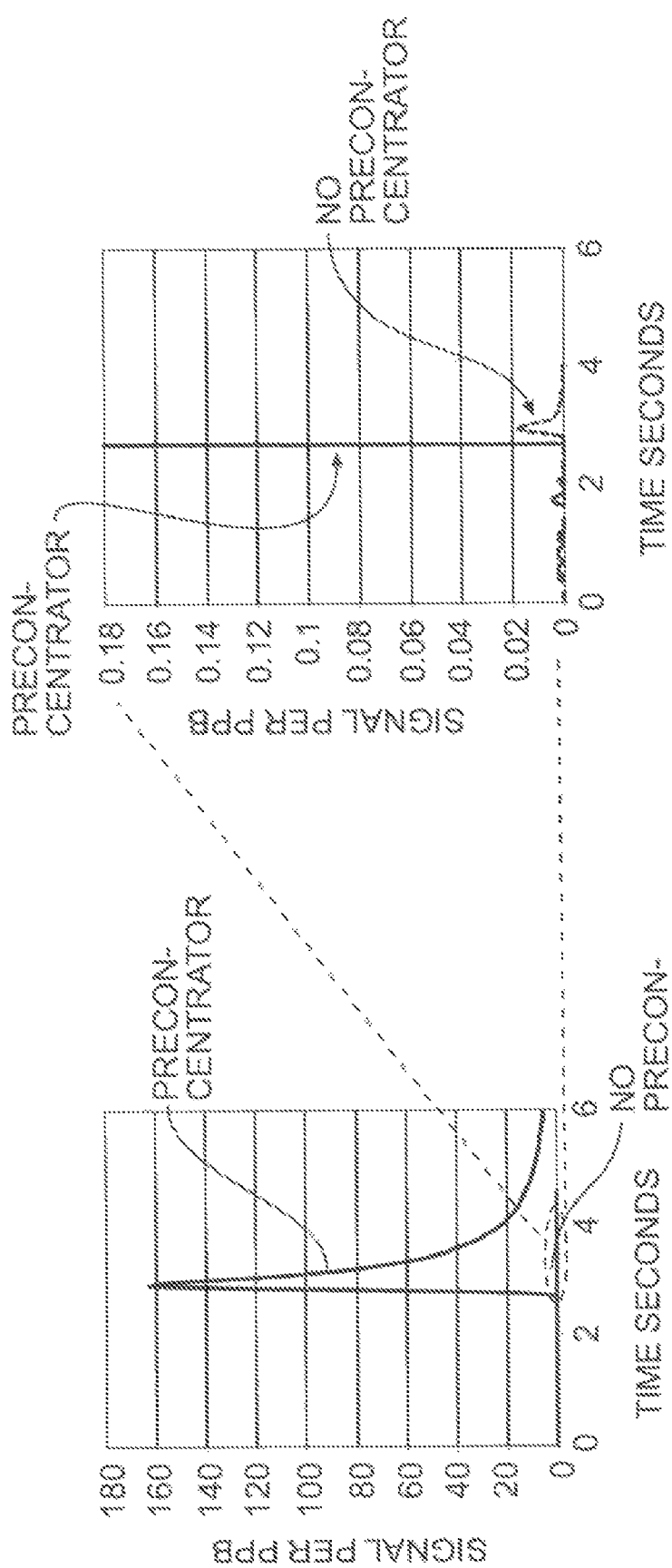
FIGS. 9A, 9B, and 10 are graphs demonstrating gains of about 8,000 to 10,000 using MOF-5 for detecting DMMP in accordance with the invention, compared to conventional detection without use of a MOF micropreconcentrator.
Figure 10:
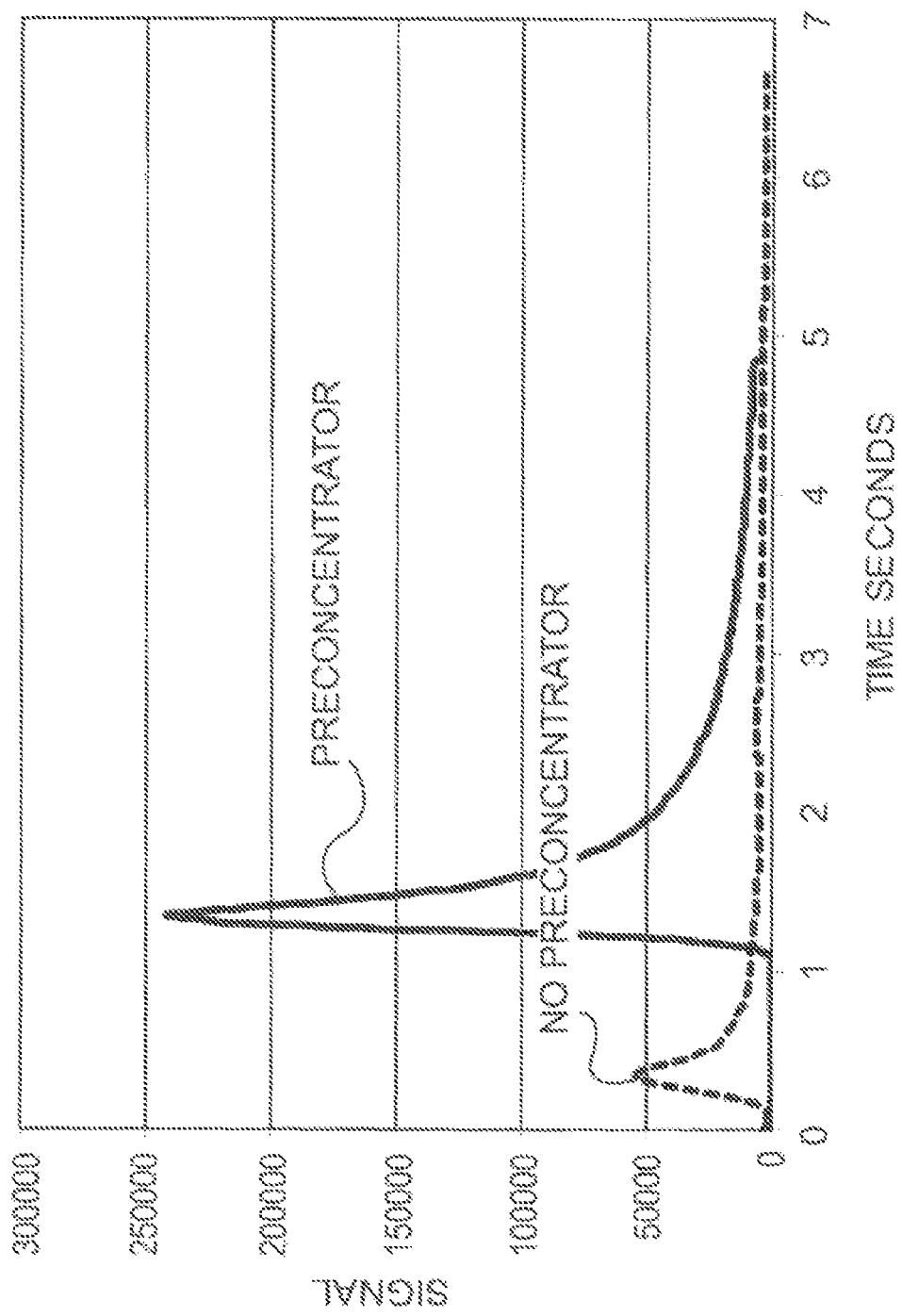

FIGS. 9A, 9B, and 10 are graphs that plot GC signals obtained during desorption of DMMP used with the preconcentrator shown in FIGS. 13 and 14 containing MOF-5 and without any preconcentrators, as a function of time. In particular, FIG. 9B is an enlargement of the dotted portion of FIG. 9A showing the peak obtained when no preconcentrator was used. Examining FIGS. 9A, 9B, and 10, it is evident that the peaks obtained when using MOF-5 in the preconcentrator are significantly larger than the peaks obtained with a conventional detector used without a MOF in the preconcentrator. In fact, FIGS. 9A, 9B, and 10 show that a significant gain of about 8,000 to about 10,000 can be achieved using the MOFs of this invention. Similar measurements using Zn-MOF-1 demonstrate a similar trend. This unexpectedly high gain demonstrates that use of a MOF in accordance with the invention greatly improves sensitivity of the GC detector.

Figure 11:
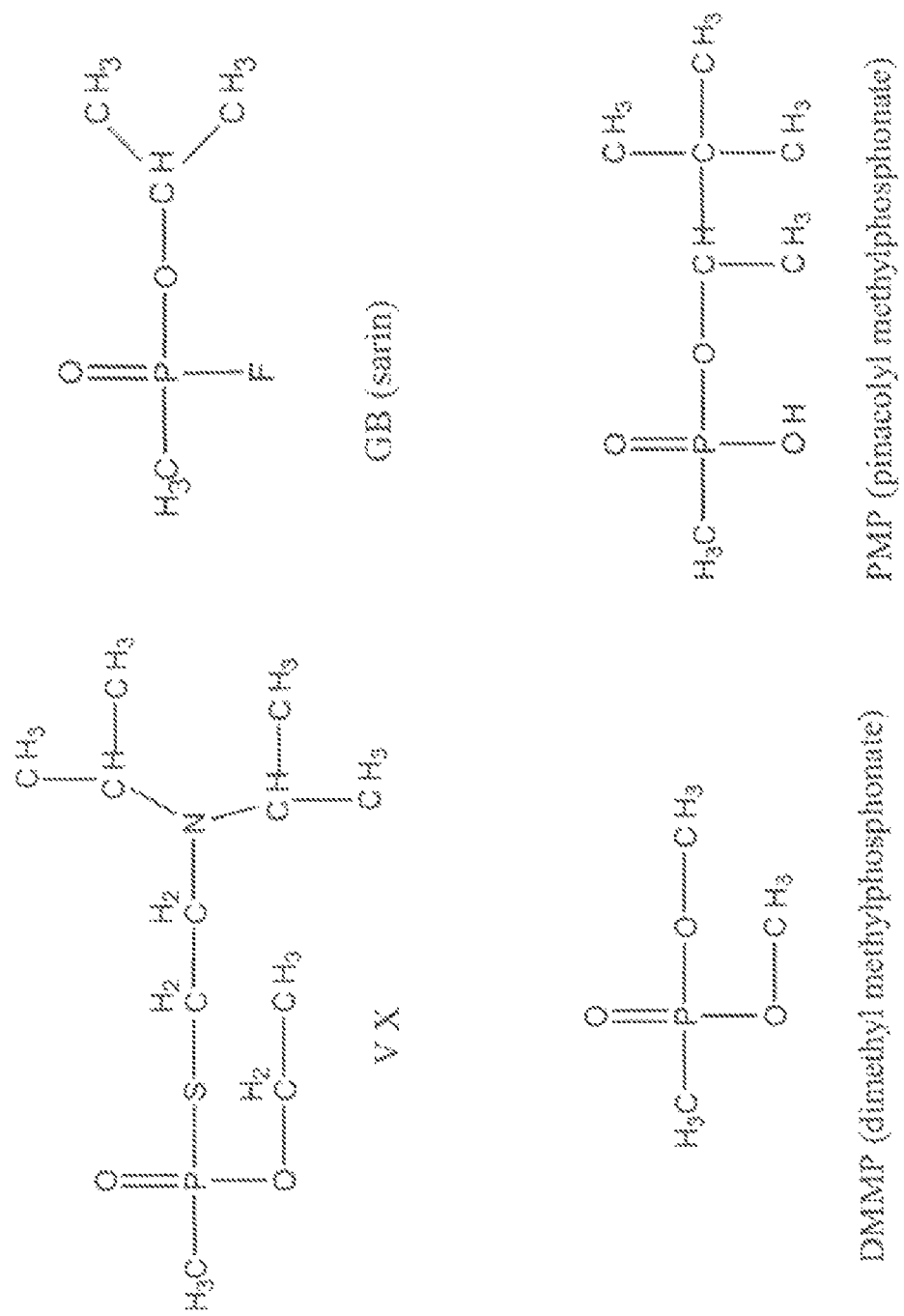
FIG. 11 illustrates a small subset of the chemical structures of various analytes that may be detected according to principles of the invention including VX, sarin, DMMP, and PMP.

In accordance with principles of the invention, MOFs may be used as sorbents in preconcentrators to detect various chemical substances and/or their precursors. FIG. 11 illustrates the chemical structures of various substances including VX, sarin, DMMP, and PMP that can be sorbed by MOFs during preconcentration and subsequently detected. Other suitable substances that have chemical structures that would be concentrated by MOFs may include, but are not limited to, diethyl methylphosphonate (DEMP), diisopropyl methylphosphonate (DIMP), dichlorohexane, malathion, acetic anhydride, TNT, RDX, and other explosives or chemical warfare agents. As described earlier, MOFs may be tailored to selectively detect specific compounds for use in various applications.

Numerous methods have been developed for synthesizing MOFs using precursors including a metal precursor and corresponding spacing ligand. The MOFs of the invention may be made according to any method known in the art, in addition to proprietary microwave methods developed by Applicants described subsequently. Solvothermal and hydrothermal synthesis methods using these precursors have conventionally been employed to form MOF crystals. Solvothermal synthesis is a method where precursors for MOF crystal formation are heated in a solvent other than water. In hydrothermal synthesis, precursors for MOF crystals are heated in water. Hydrothermal synthesis is suitable when the ligand precursor is soluble in water.

In solvothermal and hydrothermal synthesis, a solution with MOF precursors is typically maintained at a predetermined equilibrium temperature for an extended period to induce crystallization. Solvothermal and hydrothermal synthesis methods are typically slow, often taking hours and even days.

General information on different known MOFs and conventional synthesis methods are reported in a number of publications, including, "Design and Synthesis of an Exceptionally Stable and Highly Porous Metal-Organic Framework," Yaghi et al., Nature 402 (1999) 276-279; "Interwoven Metal-Organic Framework on a Periodic Minimal Surface with Extra-Large Pores, B. Chen, M. Eddaoudi," Yaghi et al. Science 291 (2001) 1021-1023; "Systematic Design of Pore Size and Functionality in Isoreticular MOFs and Their Application and Methane Storage," Yaghi et al, Science 295 (2002) 469-472; "Reticular Synthesis and Design of New Materials, Yaghi et al., Nature 423 (2003) 705-714; "Hydrogen Storage in Microporous Metal-Organic Frameworks, Yaghi et al., Science 300 (2003) 1127-1129.

Reported solvothermal synthesis methods are slow, typically taking a day or more. U.S. Published Application No. 2003/0004364 discloses a solvothermal process to form MOF materials that takes about one day to several days. In the synthesis method of the above-referenced application, a metal salt and a linear ditropic carboxylate are dissolved in a solvent to form a solution. The solution is then crystallized, which involves at least one of leaving the solution at room temperature, adding a diluted base to the solution to initiate the crystallization, diffusing a diluted base into the solution to initiate the crystallization, and transferring the solution to a closed vessel and heating to a predetermined temperature.

A multi-day hydrothermal synthesis process has also been proposed for the production of nonlinear optically active MOF material. (See e.g., "A Novel Optical Metal-Organic NLO Material Based on a Chiral 2D Coordination Network," Lin, et al., *J. Am. Chem. Soc.* 1999, 121, 11249-11250.) Others have reported a thermally stable $[Cu_3(TMA)_2(H_2O)_3]_n$, framework structure produced through a 12 hour solvothermal synthesis. (See e.g., "A Chemically Functionalizable Nanoporous Material $[Cu_3(TMA)_2(H_2O)_3]_n$," Chui, et al., Science, 1999, 283, 1148.) Catalytic active homochiral metal-organic materials formed by a two-day liquid diffusion method or solvothermal method have been reported. (See e.g., "A Homochiral Meta-organic Porous Material for Enantioselective Separation and Catalysis," Seo, et al., *Nature*, 2000, 404, 982-986; "A Homochiral Metal-Organic Material with Permanent Porosity, Enantioselective Sorption Properties, and Catalytic Activity", Dybtsev, et al., *Angew. Chem. Int. Ed.*, 2006, 45, 916-920.) Others have reported porphyrin MOF structures by a two-day solvothermal synthesis. (See e.g., "A functional zeolite analogue assembled from metalloporphyrins," Kosal, M. E.; Chou, J.-H., Wilson, S. R.; Suslick, K. S. *Nature Materials*, 2002, 1, 118-121.) Synthesis by one-week deprotonating vapor diffusion has also been reported. (See e.g., "A Robust Microporous Zinc Porphyrin Framework Solid", Smithenry, D. W. et al. *Inorg. Chem.* 2003, 42, 7719.)

As an alternative to the solvothermal and hydrothermal synthesis methods, a microwave-assisted process has been developed by the Applicants to rapidly produce a metal organic framework (MOF) material. As described in U.S. Provisional Patent Appl. No. 60/791,988, according to this method, a reactant solution including MOF precursors is exposed to microwaves for a period sufficient to achieve crystallization. The time period required may be, for example, a few seconds to a few minutes or more. The time period required for crystallization depends upon the microwave power and the solution concentration. Example formation times have ranged from about 5 seconds to about 2.5 minutes, which is a significant improvement over the conventional synthesis methods that typically take several hours or days.

Microwave-assisted MOF synthesis methods such as those described above may be particularly advantageous to the synthesis of MOFs for purposes of the invention. For example, the method of U.S. Provisional Patent Appl. No. 60/791,988 provides materials with uniform crystal size and well-defined shape. The resulting micro-sized or nano-sized crystals produced by these methods can be engineered for use in preconcentrators. Reaction conditions may be tailored to provide, for example, particle size control, larger functioning surfaces, or faster sorption kinetics. In addition, post-processing after initial synthesis may be conducted to provide larger crystals. For example, these synthesis methods provide well-defined crystals that may serve as seeds for the synthesis of larger crystals through a secondary growth process.

Another advantage of microwave-assisted MOF synthesis is that it allows one to determine the optimum conditions for crystal growth in a short amount of time. For example, one can use the microwave synthesis method to determine the conditions at which crystals of the desired structure grow, and then repeat the crystal growth under those conditions using published methods to obtain larger crystals for other purposes.

Several new MOFs were synthesized by Applicants according to the microwave-assisted method, as described in the following Examples 1-16, for use as sorbents in preconcentrators, but they may also be made by any other methods known in the art.

EXAMPLE 1

Zn-MOF1 synthesis: An exact amount of zinc nitrate hexahydrate, $Zn(NO_3)_2 \cdot 6H_2O$, (0.18 g, 0.605 mmol) and 4,4',4'',4'''-(21H,23H-porphine-5-10-15-20-tetrayl)tetrakis (benzoic acid), (0.199 g, 0.252 mmol) were dissolved in 10 mL diethylformamide. The solution was then sealed with a Pyrex sample vial and heated with a household microwave oven (800 W) for a reaction time of 80 seconds. The crystals obtained were dark purple with a cubic shape with sizes ranging from about 10 to about 30 microns.

EXAMPLE 2

Zn-MOF2 synthesis: An exact amount of zinc nitrate hexahydrate, $Zn(NO_3)_2 \cdot 6H_2O$, (0.1 g, 0.336 mmol) and 2-anilino-5-bromoterephthalic acid, (2-anilino-5-BrB-DCH2) (0.0847 g, 0.252 mmol) were dissolved in 10 mL diethylformamide. The solution was then sealed with a Pyrex sample vial and heated with a household microwave oven (800 W) for a reaction time of 80 seconds. The obtained crystals were light yellow with a cubic shape with sizes ranging from 2 to 4 microns.

EXAMPLE 3

Zn-MOF3 synthesis: An exact amount of zinc nitrate hexahydrate, $Zn(NO_3)_2 \cdot 6H_2O$, (0.15 g, 0.504 mmol) and 2-trifluoromethoxy terephthalic acid, (2-trifluoromethoxy-BDCH2) (0.0946 g, 0.378 mmol) were dissolved in 10 mL diethylformamide. The solution was then sealed with a Pyrex sample vial and heated with a household microwave oven (800 W) for a reaction time of 80 seconds. The obtained crystals were yellow with a cubic shape, with sizes ranging from about 4 to about 7 microns.

EXAMPLE 4

Zn-MOF4 synthesis: An exact amount of zinc nitrate hexahydrate, $Zn(NO_3)_2 \cdot 6H_2O$, (0.1 g, 0.336 mmol) and nitroterephthalic acid, (0.0532 g, 0.252 mmol) were dissolved in 10 mL diethylformamide. The solution was then sealed with a Pyrex sample vial and heated with a household microwave oven (800 W) for a reaction time of 80 seconds. The obtained crystals had an irregular shape.

EXAMPLE 5

Zn-MOF5 synthesis: An exact amount of zinc nitrate hexahydrate, $Zn(NO_3)_2 \cdot 6H_2O$, (0.15 g, 0.504 mmol) and cis-cyclobutane-1,2-dicarboxylic acid (0.0545 g, 0.378 mmol) were dissolved in 10 mL diethylformamide. The solution was then sealed with a Pyrex sample vial and heated with a household microwave oven (800 W) for a reaction time of 105 seconds. The obtained crystals had a square plate shape.

EXAMPLE 6

Cu-MOF1 synthesis: An exact amount of cupric nitrate, $Cu(NO_3)_2 \cdot 2.5H_2O$, (0.15 g, 0.645 mmol) and 2,5-thiophene-dicarboxylic acid, (0.0833 g, 0.484 mmol) were dissolved in 10 mL diethylformamide. The solution was then sealed with a Pyrex sample vial and heated with a household microwave oven (800 W) for a reaction time of 80 seconds.

EXAMPLE 7

Cu-MOF2 synthesis: An exact amount of cupric nitrate, $Cu(NO_3)_2 \cdot 2.5H_2O$, (0.1 g, 0.430 mmol) and 2-(trifluoromethoxy)terephthalic acid (2-trifluoromethoxy-BDCH$_2$) (0.0807 g, 0.322 mmol) were dissolved in 10 mL diethylformamide. The solution was then sealed with a Pyrex sample vial and heated with a household microwave oven (800 W) for a reaction time of 80 seconds.

EXAMPLE 8

Tb-MOF1 synthesis: An exact amount of terbium (III) nitrate pentahydrate, $Tb(NO_3)_3 \cdot 5H_2O$, (0.1 g, 0.230 mmol)

and terephthalic acid (BDC) (0.0286 g, 0.172 mmol) were dissolved in 10 mL diethylformamide. The solution was then sealed with a Pyrex sample vial and heated with a household microwave oven (800 W) for a reaction time of 80 seconds. The obtained crystals had a rod shape.

EXAMPLE 9

Tb-MOF2 synthesis: An exact amount of terbium (III) nitrate pentahydrate, $Tb(NO_3)_3*5H_2O$, (0.1 g, 0.230 mmol) and 2,5-thiophenedicarboxylic acid (0.0297 g, 0.172 mmol) were dissolved in 10 mL diethylformamide. The solution was then sealed with a Pyrex sample vial and heated with a household microwave oven (800 W) for a reaction time of 80 seconds.

EXAMPLE 10

Cd-MOF1 synthesis: An exact amount of cadmium nitrate hexahydrate, $Cd(NO_3)_2*4H_2O$, (0.1 g, 0.324 mmol) and cis-cyclobutane-1,2-dicarboxylic acid (0.0350 g, 0.243 mmol) were dissolved in 10 mL diethylformamide. The solution was then sealed with a Pyrex sample vial and heated with a household microwave oven (800 W) for a reaction time of 60 seconds.

EXAMPLE 11

Cd-MOF2 synthesis: An exact amount of cadmium nitrate tetrahydrate, $Cd(NO_3)_2*4H_2O$, (0.1 g, 0.324 mmol) and nitroterephthalic acid (0.0456 g, 0.216 mmol) were dissolved in 15 mL diethylformamide. The solution was then sealed with a Pyrex sample vial and heated with a household microwave oven (800 W) for a reaction time of 60 seconds.

EXAMPLE 12

Cd-MOF3 synthesis: An exact amount of cadmium nitrate tetrahydrate, $Cd(NO_3)_2*4H_2O$, (0.1 g, 0.324 mmol) and terephthalic acid (0.0404 g, 0.243 mmol) were dissolved in 10 mL diethylformamide. The solution was then sealed with a Pyrex sample vial and heated with a household microwave oven (800 W) for a reaction time of 90 seconds.

EXAMPLE 13

Co-MOF1 synthesis: An exact amount of cobalt (II) nitrate hexahydrate, $Co(NO_3)_2*6H_2O$, (0.1 g, 0.343 mmol) and terephthalic acid (0.0428 g, 0.258 mmol) were dissolved in 10 mL diethylformamide. The solution was then sealed with a Pyrex sample vial and heated with a household microwave oven (800 W) for a reaction time of 60 seconds.

EXAMPLE 14

Co-MOF2 synthesis: An exact amount of cobalt (II) nitrate hexahydrate, $Co(NO_3)_2*6H_2O$, (0.1 g, 0.343 mmol) and 1,3,5-benzenetricarboxylic acid (0.0542 g, 0.258 mmol) were dissolved in 10 mL diethylformamide. The solution was then sealed with a Pyrex sample vial and heated with a household microwave oven (800 W) for a reaction time of 60 seconds.

EXAMPLE 15

Zn-MOF6 synthesis: An exact amount of zinc nitrate hexahydrate, $Zn(NO_3)_2*6H_2O$, (0.05 g, 0.168 mmol) and 3,3-bis(trifluoromethyl)-1-oxo-5-isobenzofurancarboxylic acid (0.0396 g, 0.126 mmol) were dissolved in 7 mL diethylformamide/3 mL $H_2O$. The solution was then sealed with a Pyrex sample vial and heated with a household microwave oven (800 W) for a reaction time of 120 seconds. The obtained crystals had a hexagonal cylinder shape, with size ranging from about 2 to about 4 microns.

In addition, new MOFs were synthesized according to the methods described in U.S. Patent Publication No. 2005/0192175, the disclosure of which is expressly incorporated by reference herein in its entirety, as described in the following Example 16, for use as sorbents in preconcentrators.

EXAMPLE 16

Zn-MOF1 synthesis: 0.239 g of 4,4',4",4'''-(21H, 23H-Porphine-5,10,15,20-tetrayl)tetrakis(benzoic acid) (H2TPP) and 0.18 g of $Zn(NO_3)_2.6H_2O$ were dissolved in 60 mL DEF. The solution was stirred for 3 hours and then sealed in a closed vessel. The vessel was heated to 100° C. at 2° C./minute. Dark purple crystals were collected after 3 days for a yield of 40%.

Specific known MOFs were synthesized either using microwave synthesis or according to the methods described in U.S. Patent Publication No. 2005/0192175, as described in the following Examples 17-35.

EXAMPLE 17

50-1,000 micron MOF-5 synthesis: 0.200 g $Zn(NO_3)_2.6H_2O$ and 0.084 g 1,4-dibenzenedicarboxylate ($H_2BDC$) ligand in were dissolved 20 mL N,N' diethylformamide (DEF). The solution was stirred for 30 minutes and then heated in a closed vessel at 80° C. After 1-3 days, small transparent crystals were obtained with a size distribution between about 50 and about 1,000 microns.

EXAMPLE 18

30-50 micron MOF-5 synthesis: The MOF-5 crystals in Example 17 were ground with a mortar and pestle. They were then sorted with a 120 mesh sieve to produce particles that were between about 30 and about 45 microns in diameter.

EXAMPLE 19

4-6 micron MOF-5 synthesis: An exact amount of $Zn(NO_3)_2.6H_2O$ (0.2 g, 0.67 mmol) and 1,4-benzenedicarboxylate acid (BDCH2) (0.083 g, 0.50 mmol) were dissolved in 10 mL of the N,N'-diethylformamide (DEF) resulting in a clear solution. One mL of the solution was sealed in a 4-mL Pyrex sample vial. The vial was then placed inside a hood behind a blast shield and heated by a microwave synthesizer (Resonance Instrument Inc. Model 520A) at 150 W for about 25 seconds. A yellow suspension formed after the microwave treatment. The product was rinsed (centrifuged and re-dispersed in DEF by sonicating) for 3 times before analysis. Light yellow crystals with a particle size of about 4-6 microns were observed.

EXAMPLE 20

3 micron MOF-5 synthesis: An exact amount of $Zn(NO_3)_2.6H_2O$ (0.2 g, 0.67 mmol) and 1,4-benzenedicarboxylate acid (BDCH2) (0.083 g, 0.50 mmol) were dissolved in 10 mL of the N,N'-diethylformamide (DEF) resulting in a clear solution. The solution was diluted with DEF until the $BDCH_2$ concentration was approximately 25 mmol/L. One mL of the solution was sealed in a 4-mL Pyrex sample vial. The vial was then placed inside a hood behind a blast shield and heated by a microwave synthesizer (Resonance Instrument Inc. Model 520A) at 150 W for about 33 seconds. A yellow suspension formed after the microwave treatment. The product was rinsed (centrifuged and re-dispersed in DEF by sonicating) for 3 times before analysis. Light yellow crystals with average particle size of about 3 micron were observed.

EXAMPLE 21

1.5 micron MOF-5 synthesis: An exact amount of $Zn(NO_3)_2 \cdot 6H_2O$ (0.2 g, 0.67 mmol) and 1,4-benzenedicarboxylate acid (BDCH2) (0.083 g, 0.50 mmol) were dissolved in 10 mL of the N,N'-diethylformamide (DEF) resulting in a clear solution. The solution was diluted with DEF until the $BDCH_2$ concentration was approximately 12.5 mmol/L. One mL of the solution was sealed in a 4-mL Pyrex sample vial. The vial was then placed inside a hood behind a blast shield and heated by a microwave synthesizer (Resonance Instrument Inc. Model 520A) at 150 W for about 41 seconds. A yellow suspension formed after the microwave treatment. The product was rinsed (centrifuged and re-dispersed in DEF by sonicating) for 3 times before analysis. Light yellow crystals with average particle size of about 1.5 micron were observed.

EXAMPLE 22

0.75 micron MOF-5 synthesis: An exact amount of $Zn(NO_3)_2 \cdot 6H_2O$ (0.2 g, 0.67 mmol) and 1,4-benzenedicarboxylate acid (BDCH2) (0.083 g, 0.50 mmol) were dissolved in 10 mL of the N,N'-diethylformamide (DEF) resulting in a clear solution. The solution was diluted with DEF until the $BDCH_2$ concentration was approximately 6.25 mmol/L. One mL of the solution was sealed in a 4-mL Pyrex sample vial. The vial was then placed inside a hood behind a blast shield and heated by a microwave synthesizer (Resonance Instrument Inc. Model 520A) at 150 W for about 49 seconds. A yellow suspension formed after the microwave treatment. The product was rinsed (centrifuged and re-dispersed in DEF by sonicating) for 3 times before analysis. Light yellow crystals with average particle size of about 0.75 micron were observed.

EXAMPLE 23

MOF-5 synthesis: An exact amount of $Zn(NO_3)_2 \cdot 6H_2O$ (0.2 g, 0.67 mmol) and 1,4-benzenedicarboxylate acid (BDCH2) (0.083 g, 0.50 mmol) were dissolved in 10 mL of the N,N'-diethylformamide (DEF) resulting in a clear solution. The solution was diluted with DEF until the $BDCH_2$ concentration was approximately 3.13 mmol/L. One mL of the solution was sealed in a 4-mL Pyrex sample vial. The vial was then placed inside a hood behind a blast shield and heated by a microwave synthesizer (Resonance Instrument Inc. Model 520A) at 150 W for about 57 seconds. A yellow suspension formed after the microwave treatment. The product was rinsed (centrifuged and re-dispersed in DEF by sonicating) for 3 times before analysis. Light yellow crystals with average particle size of about 0.5 micron were observed.

EXAMPLE 24

MOF-5 synthesis: An exact amount of $Zn(NO_3)_2 \cdot 6H_2O$ (0.2 g, 0.67 mmol) and 1,4-benzenedicarboxylate acid (BDCH2) (0.083 g, 0.50 mmol) were dissolved in 10 mL of the N,N'-diethylformamide (DEF) resulting in a clear solution. The solution was diluted with DEF until the $BDCH_2$ concentration was approximately 1.56 mmol/L. One mL of the solution was sealed in a 4-mL Pyrex sample vial. The vial was then placed inside a hood behind a blast shield and heated by a microwave synthesizer (Resonance Instrument Inc. Model 520A) at 150 W for about 65 seconds. A yellow suspension formed after the microwave treatment. The product was rinsed (centrifuged and re-dispersed in DEF by sonicating) for 3 times before analysis. Light yellow crystals with an average particle size of about 0.5 micron were observed.

EXAMPLE 25

0.4 micron MOF-5 synthesis: An exact amount of $Zn(NO_3)_2 \cdot 6H_2O$ (0.2 g, 0.67 mmol) and 1,4-benzenedicarboxylate acid (BDCH2) (0.083 g, 0.50 mmol) were dissolved in 10 mL of the N,N'-diethylformamide (DEF) resulting in a clear solution. The solution was diluted with DEF until the $BDCH_2$ concentration was approximately 0.78 mmol/L. One mL of the solution was sealed in a 4-mL Pyrex sample vial. The vial was then placed inside a hood behind a blast shield and heated by a microwave synthesizer (Resonance Instrument Inc. Model 520A) at 150 W for about 73 seconds. A yellow suspension formed after the microwave treatment. The product was rinsed (centrifuged and re-dispersed in DEF by sonicating) for 3 times before analysis. Light yellow crystals with average particle size of 0.4 micron were observed.

EXAMPLE 26

0.3 micron MOF-5 synthesis: An exact amount of $Zn(NO_3)_2 \cdot 6H_2O$ (0.2 g, 0.67 mmol) and 1,4-benzenedicarboxylate acid (BDCH2) (0.083 g, 0.50 mmol) were dissolved in 10 mL of the N,N'-diethylformamide (DEF) resulting in a clear solution. The solution was diluted with DEF until the $BDCH_2$ concentration was approximately 0.39 mmol/L. One mL of the solution was sealed in a 4-mL Pyrex sample vial. The vial was then placed inside a hood behind a blast shield and heated by a microwave synthesizer (Resonance Instrument Inc. Model 520A) at 150 W for about 81 seconds. A yellow suspension formed after the microwave treatment. The product was rinsed (centrifuged and re-dispersed in DEF by sonicating) for 3 times before analysis. Light yellow crystals with average particle size of 0.3 micron were observed.

EXAMPLE 27

100-300 nm MOF-5 synthesis: An exact amount of $Zn(NO_3)_2 \cdot 6H_2O$ (0.2 g, 0.67 mmol) and 1,4-benzenedicarboxylate acid (BDCH2) (0.083 g, 0.50 mmol) were dissolved in 10 mL of the N,N'-diethylformamide (DEF) resulting in a clear solution. The solution was diluted with DEF until the $BDCH_2$ concentration was approximately 0.20 mmol/L. One mL of the solution was sealed in a 4-mL Pyrex sample vial. The vial was then placed inside a hood behind a blast shield and heated by a microwave synthesizer (Resonance Instrument Inc. Model 520A) at 150 W for about 90 seconds. A yellow suspension formed after the microwave treatment. The product was rinsed (centrifuged and re-dispersed in DEF by sonicating) for 3 times before analysis. Light yellow crystals with average particle size of about 0.1 to about 0.3 microns (i.e. 100 to 300 nm) were observed.

EXAMPLE 28

IRMOF2 synthesis: An exact amount of 2-bromoterephthalic acid, (2-BrBDCH2) (0.040 g, 0.160 mmol), and zinc nitrate hexahydrate, $Zn(NO_3)_2 \cdot 6H_2O$, (0.0594 g, 0.20 mmol)

were dissolved in 15 mL diethylformamide. The solution was then sealed with a Pyrex sample vial and heated at 150 W for a reaction time of about 40 seconds. A yellow suspension formed after the microwave treatment.

EXAMPLE 29

IRMOF3 synthesis: An exact amount of 2-aminoterephthalic acid, (2-Amino-BDCH2) (0.2 g, 0.67 mmol) and zinc nitrate hexahydrate, $Zn(NO_3)_2.6H_2O$, (0.0913 g, 0.504 mmol) were dissolved in a mixture of 39 mL diethylformamide and 3 mL ethanol. The solution was then sealed with a Pyrex sample vial and heated at 150 W for a reaction time of about 35 seconds. An orange suspension formed after the microwave treatment.

EXAMPLE 30

$Cu(4,4'-bpy)_{1.5}NO_3(H_2O)_{1.25}$ synthesis described in detail in JACS 1995, 117, 10401-10402: An exact amount of $Cu(NO_3)_2.2.5H_2O$ (0.1133 g, 0.487 mmol), 4,4'-dipyridyl (0.114 g, 0.730 mmol), and 1,3,5-triazine (0.026 g, 0.323 mmol) were dissolved in 15 mL of deionized water. The solution was then sealed with a Pyrex sample vial and heated with a household microwave oven (800 W) for a reaction time of about 60 seconds.

EXAMPLE 31

$[Cu_3(TMA)_2]_n$ synthesis described in detail in Science 1999, 283, 1148-1150: An exact amount of cupric nitrate $Cu(NO_3)_2.2.5H_2O$ (0.1 g, 0.430 mmol) and 1,3,5-benzenetricarboxylic acid (0.05 g, 0.239 mmol) were dissolved in 10 mL of DEF. The solution was then sealed with a Pyrex sample vial and heated with a household microwave oven (800 W) for a reaction time of about 60 seconds.

EXAMPLE 32

$[Cu(OH)—(C_5H_4NCO_2]_n$ synthesis described in detail in Inorg. Chem. 2005, 44, 6192-6196: An exact amount of cupric nitrate $Cu(NO_3)_2.2.5H_2O$ (0.1 g, 0.430 mmol) and isonicotinic acid (0.067 g, 0.430 mmol) were dissolved in 4 mL of deionized water. The solution was then sealed with a Pyrex sample vial and heated with a household microwave oven (800 W) for a reaction time of about 60 seconds.

EXAMPLE 33

MOF-38 synthesis described in detail in JACS, 2001, 123, 8239-8247: An exact amount of zinc nitrate hexahydrate, $Zn(NO_3)_2.6H_2O$ (0.1 g, 0.336 mmol) and 1,3,5-benzene-tricarboxylic acid (0.039 g, 0.187 mmol) were dissolved in 10 mL of DEF. The solution was then sealed with a Pyrex sample vial and heated with a household microwave oven (800 W) for a reaction time of about 60 seconds.

EXAMPLE 34

$Ag(4,4'-bpy)NO_3$ synthesis described in detail in JACS, 1996, 118, 295-296: An exact amount of silver nitrate, $Ag(NO_3)$ (0.050 g, 0.294 mmol) and 4,4'-dipyridyl (0.051 g, 0.325 mmol) were dissolved in 10 mL of deionized water. The solution was then sealed with a Pyrex sample vial and heated with a household microwave oven (800 W) for a reaction time of about 60 seconds.

EXAMPLE 35

IRMOF7 synthesis: An exact amount of 1,4 naphthalene dicarboxylic acid, (0.109 g, 0.504 mmol) and zinc nitrate hexahydrate, $Zn(NO_3)_2.6H_2O$, (0.2 g, 0.673 mmol) were dissolved in a 15 mL diethylformamide. The solution was then sealed with a Pyrex sample vial and heated at 150 W for a reaction time of about 60 seconds.

Of the MOF-5 samples prepared by the procedures described above, those in Examples 21, 22 and 23 worked better in sorption experiments than those prepared by the procedures in Examples 20, 24, 25, 26, and 27. MOF-5 with particle sizes above 10 microns showed slower sorption and desorption, which limited their utility in experiments where the sorption/desorption time needed to be under 4 seconds. The particles with sizes below 1 micron gave high pressure drops. In addition, the weight of MOF that adhered to the epoxy (discussed below) in the preconcentrator in FIG. 14, decreased as the particle size was reduced, thus reducing the preconcentrators' effectiveness. Thus, the particles that were smaller than 1 micron were less effective in the preconcentrator design of FIGS. 13 and 14.

Figure 12:
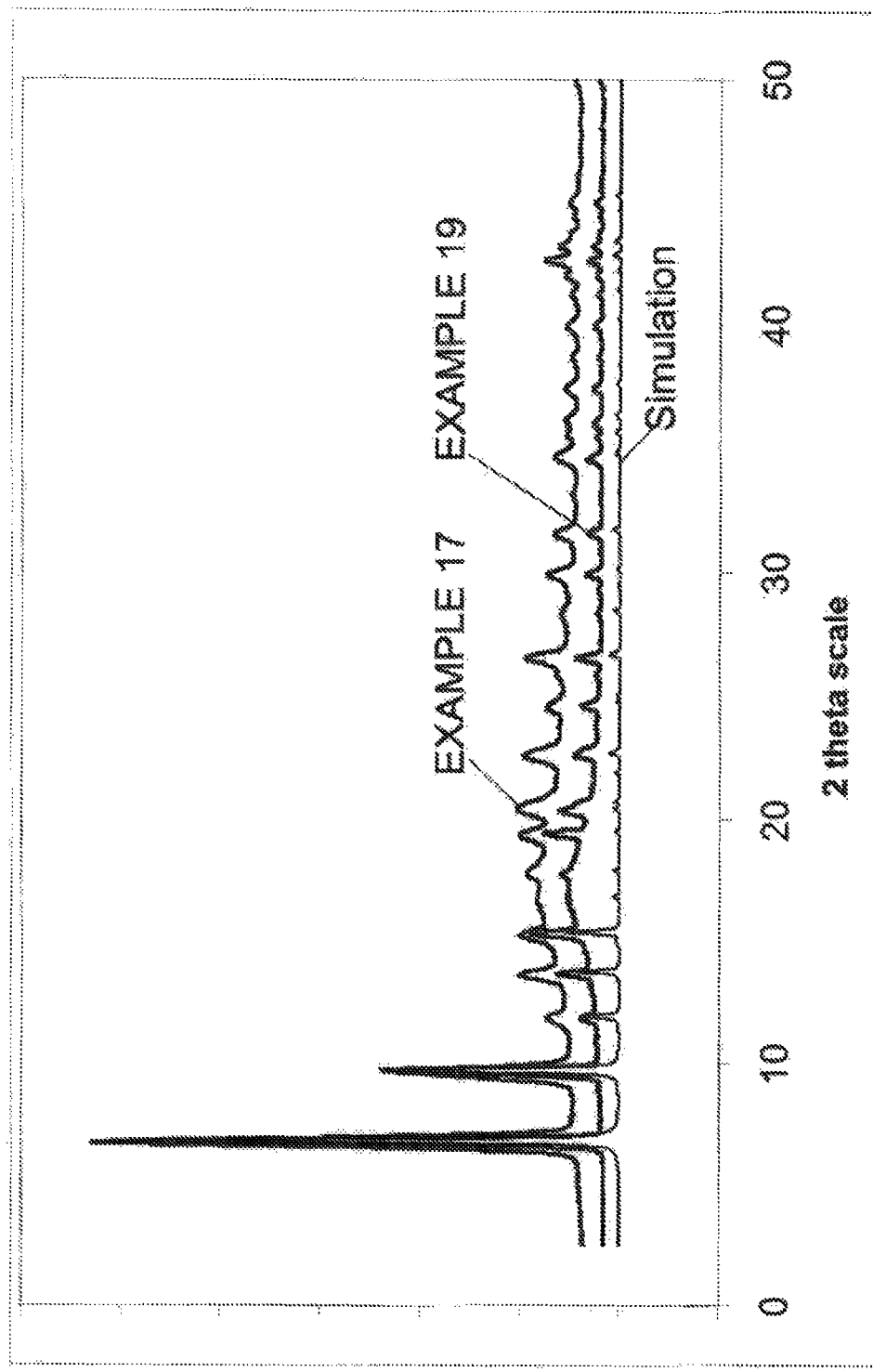
FIG. 12 shows a plot of an x-ray powder diffraction (XRPD) pattern for the MOF-5 synthesized according to the principles of the invention, along with a simulated pattern obtained from literature.

Once the MOFs were formed, they were characterized using x-ray powder diffraction (XRPD) to confirm their composition. XRPD patterns were collected on a Bruker General Area Detector Diffraction System for 900 seconds with an 8.5 cm sample-to-detector distance. Solvated crystals used for XRPD measurements were transferred along with a mother liquor into a 0.7 mm capillary tube. For example, FIG. 12 plots an XRPD pattern for the MOF-5 obtained in Example 16 along with a simulated pattern obtained from literature. It is evident from FIG. 12 that the XRPD pattern for laboratory-synthesized MOF-5 and the simulated pattern coincide closely, indicating that the laboratory-synthesized MOF-5 was formed correctly.

As mentioned previously, the MOFs described in this invention can be used in various known or new types of preconcentrators for use in a wide range of analytical instruments and detectors. Specific embodiments of preconcentrators of the invention that may employ MOFs include a conventional purge and trap system using a modified rotor (such as that described in connection with FIGS. 13-14), a MEMS valve system (such as the valve designs described in FIGS. 15-22B which may or may not include microposts), vacuum cleaner assisted preconcentrator, dosimeter, swab, and disc or pellet, as described in more detail below. While the detailed embodiments disclosed herein are directed to microreconcentrators, the skilled artisan will recognize that the principles of the invention may be scaled up and practiced as a preconcentrator.

FIGS. 13 and 14 schematically illustrate the loading and operation of a purge and trap micropreconcentrator system, 100, with a modified rotor design containing MOFs, according to an embodiment of the invention. This system provides high gain because most of the analyte is collected from a large volume sample and is then trapped in a small space. As shown in FIG. 13, MOF crystals are mounted into the rotor of a conventional Valco® injector valve 110. Specifically, the rotor has four 0.05 µL grooves and the MOF is loaded into one of the grooves referred to as the sample groove 112.

Three methods were used to hold the MOF in the grooves. In the first method, MOF particles that were approximately the same diameter as the groove were placed in the groove and held via friction. In a second method, a thin layer of Locktite quickset epoxy was placed in the groove. Then, MOF powder was pressed into the grove on top of the epoxy, the epoxy was allowed to dry, and then any loose particles were blown off of the groove using a nitrogen stream. According to a third method, particles were put in a small capillary which was then placed or glued into the groove.

During the operation of the purge and trap microprecentrator 100, the sample groove 112 is rotated to each of the four positions labeled A-D in FIGS. 13 and 14. Position A couples the sample groove 112 to the sample and carrier gas inlet 114 and the vent 116. Position B has no connections, so when the sample groove 112 is in this position, its contents have no outlet. Position C couples the sample groove 112 to a heater 118, for example, for the desorption step. Position D couples the sample groove 112 to a purge gas inlet 132 and to a detector through a GC column 130, for example.

As described in more detail below, a carrier gas is supplied from a carrier gas cylinder 120, for example, and may pass through a mass flow controller 122 before being supplied to the valve 110 at position A. A purge gas may be supplied from a purge gas cylinder 124, for example, through a purge gas pressure gauge 126 before being supplied to the valve 110 at position D.

As shown in FIG. 13, the sample groove 112, shown at position A, may be loaded with MOFs in any suitable manner. For example, the sample groove may be loaded with a predetermined number, e.g., five cubic MOF crystals, or the sample groove 112 may also be covered with 1-10 micron MOF particles. Referring to Step 1 of FIG. 14, the sample groove 112 is in or is moved to position A where a sample gas from the sample and carrier gas inlet 114 containing an analyte such as DMMP vapor is allowed to flow from an ice-bath bubbler 128 (as shown in FIG. 13) to the sample groove 112 at 20 sccm, for example, at room temperature for about one minute, for example. The MOFs in the sample groove 112 sorb and trap the analyte in the sample groove 112 at position A. Excess gas is allowed to leave through the vent 116.

Next, in Step 2, the valve 110 is rotated so that the sample groove 112 is in position B. The MOF and analyte stay trapped in sample groove 112 because position B provides no connections to the outside. Then in Step 3, the sample groove 112 containing the analyte and MOF are rotated to position C where they are heated by means known in the art, such as a suitable heater 118, to a temperature to cause desorption of the analyte, e.g., to about 220° C. In this step, the analyte desorbs from the MOF but stays trapped in the sample groove 112.

Last, in Step 4, the valve 110 is rotated such that the sample groove 112 is in position D and is thus coupled to the GC column 130. During Step 4, the desorbed analyte leaves the sample groove 112 and a purge gas such as hydrogen or helium may be introduced to assist in injecting or pushing the analyte out of the sample groove from the purge gas inlet 132 at position D. As known in the art, the flow rate of the purge gas is adjusted to avoid diluting the analyte. After the analyte are purge gas are transferred from the sample groove 112 in Step 4, to the column 130, they then flow to a detector (not shown). For example, the injected vapor may be passed from the column to a flame ionization detector (FID) of a GC.

Another embodiment of a preconcentrator according to the invention involves use of multiple electrostatically actuated MEMS valves. In one embodiment, a preconcentrator includes five microvalves that may be constructed according to the teachings of U.S. patent application Ser. No. 11/493, 376, the disclosure of which is expressly incorporated by reference herein in its entirety, and which work together to supply a concentrated analyte to a detector. The five microvalve system may be used with MOFs as well as other high surface area sorbents, as described below. In addition to the five microvalve configuration, the preconcentrator may be actuated with only two valves, inlet and outlet valves, as well as without an active valve in the split "Y" valve configuration more commonly found in large scale preconcentrator systems.

Figure 15A:
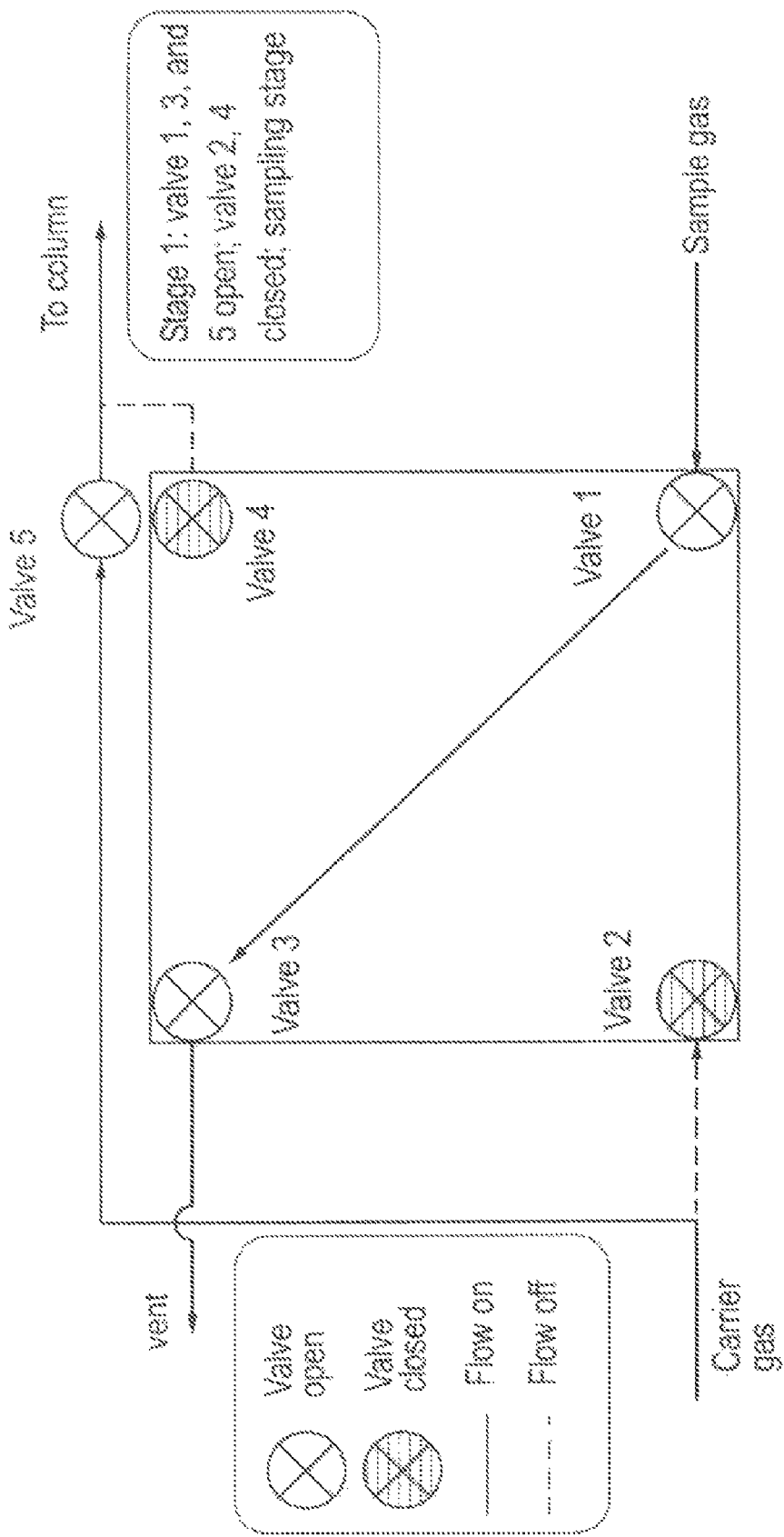
FIG. 15A is a conceptual flow diagram that describes the operation of a five microvalve preconcentrator constructed according to the principles of the invention.

FIGS. 15A-15H are schematic diagrams illustrating the operation of the five microvalve preconcentrator, the basic design of which may be constructed according to teachings of U.S. patent application Ser. No. 11/493,376. FIG. 15A is a conceptual flow diagram that describes the operation of a five microvalve preconcentrator. Valve 1 is the sample gas input valve through which the sample gas is supplied to the preconcentrator. Valve 2 is the carrier gas input valve that is used to introduce carrier gas through the preconcentrator. Valve 3 is the vent valve, through which sample gas and carrier gas are vented to the atmosphere. Valve 4 is the column injection valve from the preconcentrator through which the sample gas passes. Valve 5 is an optional bypass valve for carrier gas that bypasses the preconcentrator and goes directly from the carrier gas inlet to the column. In FIGS. 15A-H, the valves shown without cross-hatching are open and those with cross-hatching are closed.

If valve 5 is not used for the bypass, valve 4 may simply feed a split "Y" valve with carrier gas continually flowing. The addition of valve 5 allows sharper insertion of the desorbed gas into a separation column. In one embodiment, valves 1, 2, and 3 have the same structure as the single valve design disclosed in U.S. patent application Ser. No. 11/493, 376. In a second embodiment, valves 4 and 5 are integrated and operated opposite each other such that when one valve is closed, the other valve is open.

Figure 15B:
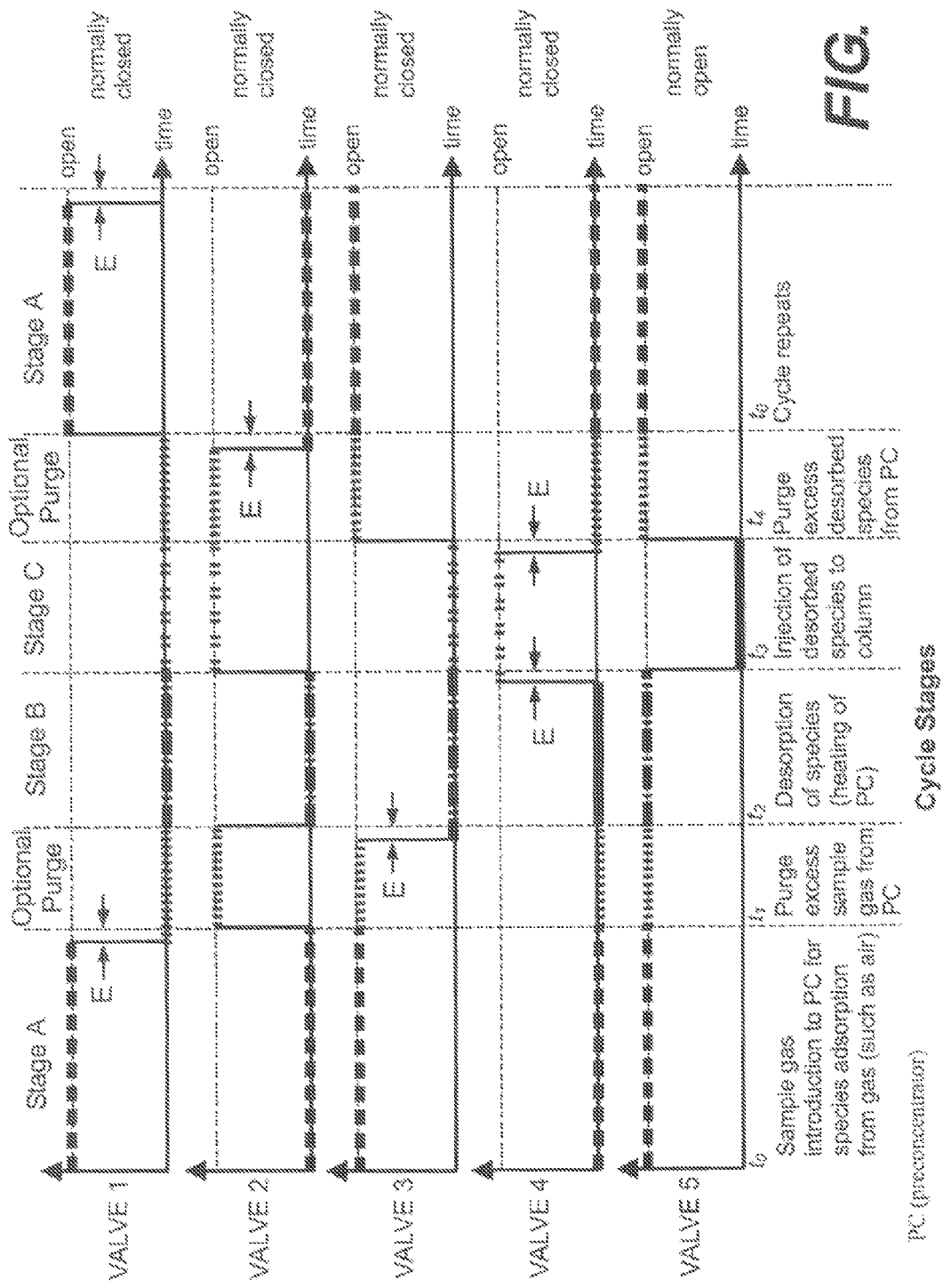
FIG. 15B is a diagram that demonstrates an exemplary timing cycle for a five microvalve preconcentrator constructed according to the principles of the invention.

FIG. 15B is a diagram that demonstrates an exemplary timing of the five microvalves. Referring to FIG. 15B, there are three main stages, A, B, and C and two optional purge stages. In Stage A, which begins at time $t_0$, the preconcentrator is loaded with the sample gas. Loading is accomplished by supplying the sample gas through the preconcentrator by opening sampling valve 1, as shown in FIG. 15A. The sorbent is contained in a collection chamber 236 which communicates with and/or is integrated with the valves as shown in FIGS. 15G and 15H. Vent valve 3 is also open during Stage A, as shown in FIG. 15A, allowing sample gas to exit the preconcentrator through the vent, after passing by the sorbent in the collection chamber 236. The duration of loading, $t_0$-$t_1$, determines the amount of analyte carried in the sample gas that is sorbed within the preconcentrator by the sorbent. The longer the duration of loading for a given flow rate, the more the desired species are sorbed, and the higher the gain, up to saturation of the sorbent. Carrier gas valve 2 and injection valve 4 are closed and bypass valve 5 is open during Stage A, as shown in FIG. 15A.

Figure 15C:
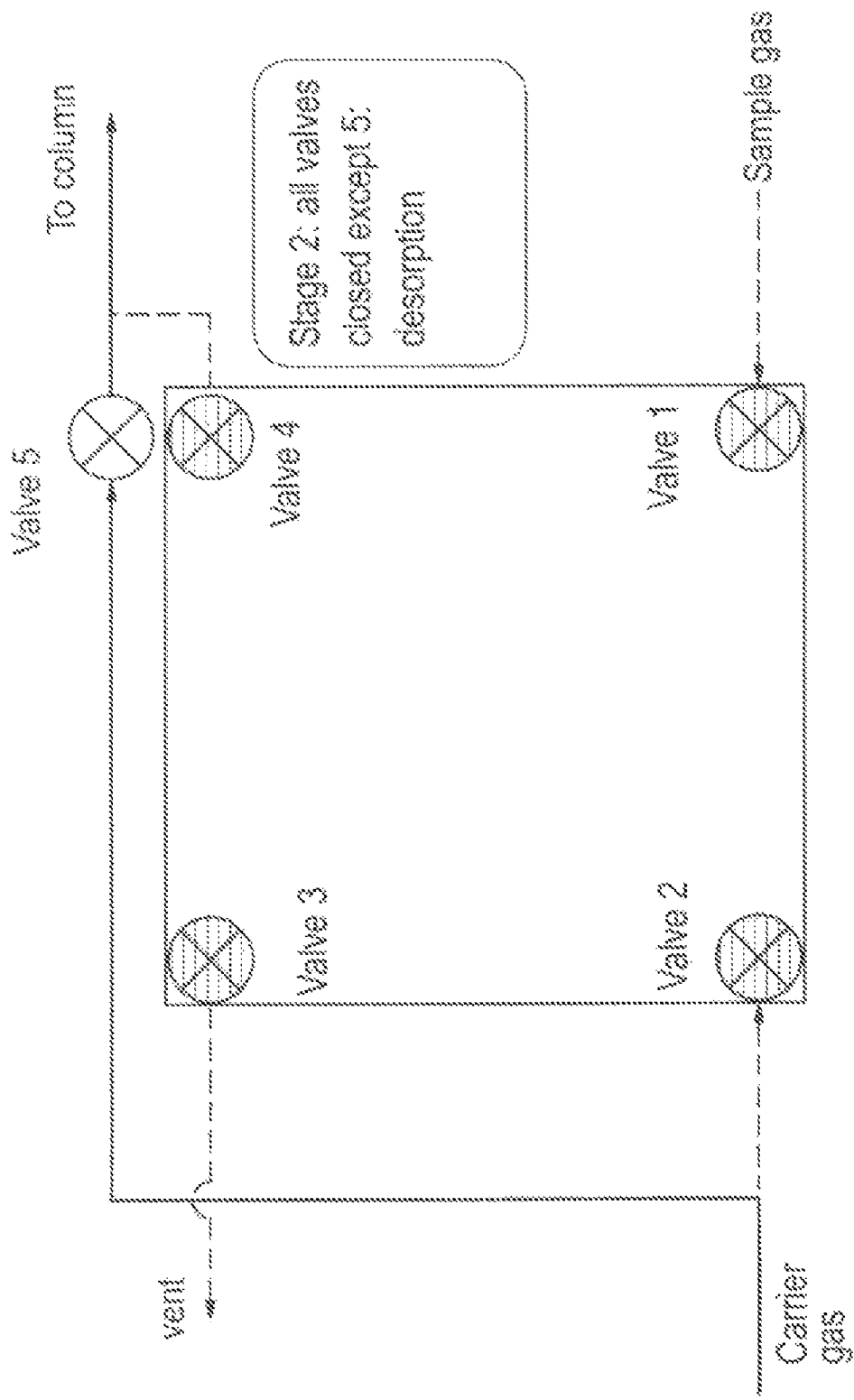
FIG. 15C is a conceptual flow diagram that shows the position of the valves during desorption in Stage B at time $t_2$ according to the timing diagram of FIG. 15B.

FIG. 15C illustrates desorption in Stage B at time $t_2$. As shown in FIG. 15B, valves 1, 2, 3, and 4 are closed and the preconcentrator is heated to a temperature sufficient to desorb all or most of the analyte off the sorbent. Pressure rises in the preconcentrator during Stage B.

Figure 15D:
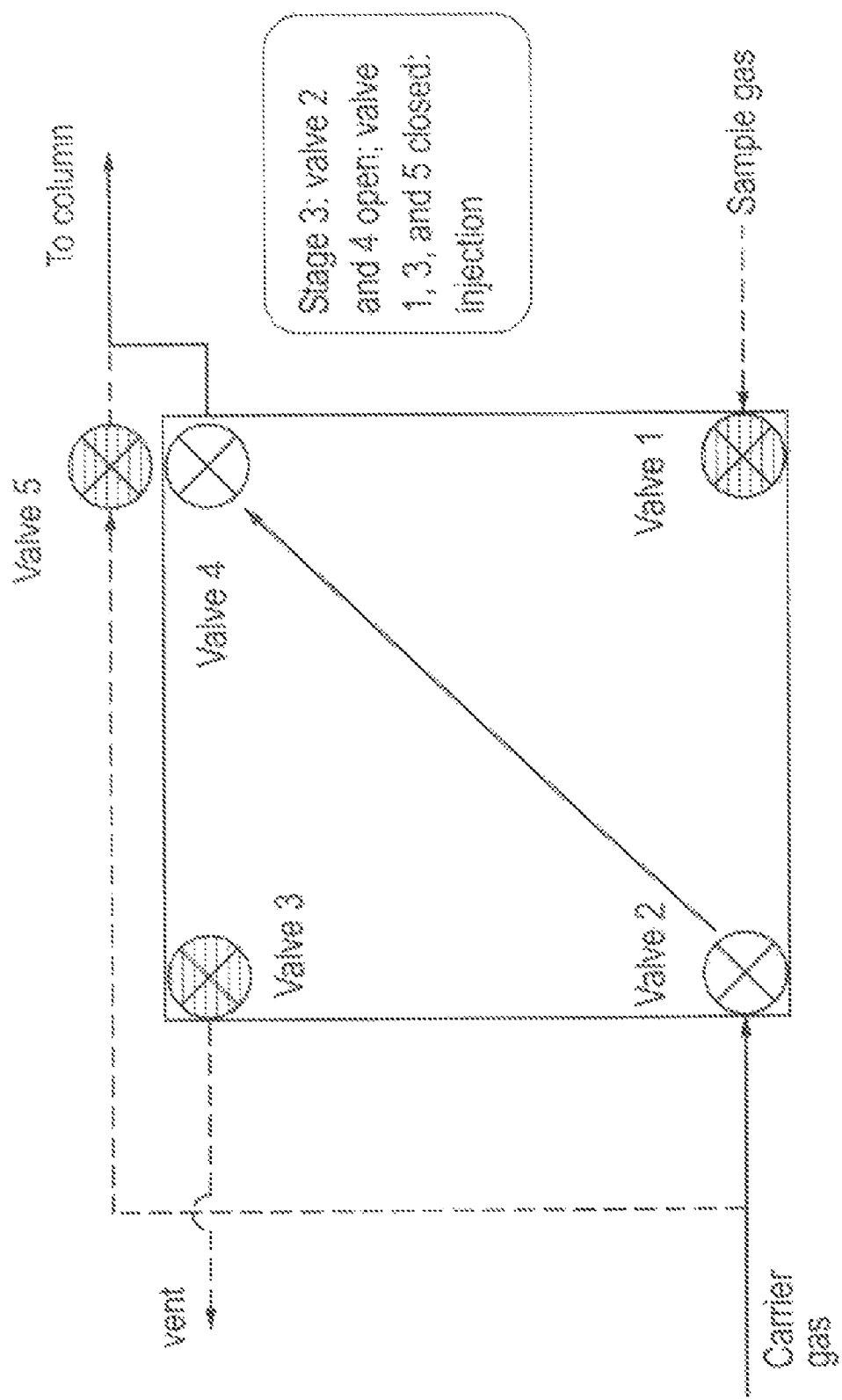
FIG. 15D is a conceptual flow diagram that shows the positions of the valves when the desorbed analyte is injected out of the preconcentrator and into a GC in Stage C at time $t_3$ according to the timing diagram of FIG. 15B.

Stage C begins at time $t_3$ and is illustrated in FIG. 15D. FIG. 15D shows how the sample gas is injected out of the preconcentrator and into a column, for example. Injection valve 4 is opened and bypass valve 5 is closed, starting the flow of gas in the preconcentrator. Shortly thereafter, carrier gas valve 2 is opened, allowing the carrier gas to be passed through the preconcentrator to the detector, such as a FID, through the column of a GC. The injection from the preconcentrator is stopped by closing valve 4 and reopening bypass valve 5 after time $t_4$. If an optional purge is not used, valve 2 is also closed at $t_4$.

There are two optional purge stages that may be taken between Stage A and Stage B at time $t_1$, and then again at time $t_4$ between Stage C and the next Stage A. These steps can be added to prevent the sample gas from being eluted into the column and so that analyte from a sample gas is eliminated from the preconcentrator to avoid cross-contamination of consecutive samples. The purge gas also reduces the impact of dead volume between the preconcentrator and the valves, since this volume is filled with carrier gas, and not sample gases.

In addition to Stages A, B, C, and the two optional purge stages, offset times, δ, may be added to the stage timing so that the valve pairs 1 and 3, 2 and 4, and 4 and 5 are not opened and closed at exactly the same time. This is illustrated in FIG. 15B. These offsets may be employed to reduce crossover between sample and carrier gases, column and vent, etc., as well as to reduce fluid flow surges between valve switching.

Valves 1, 2, 3, and 4 may have substantially the same design such as that described in U.S. patent application Ser. No. 11/493,376 as described above, while valve 5 may have a different design. Valves 1, 2, 3, and 4 are normally closed valves, and only open on actuation. Valve 5 is a normally open valve that only closes on actuation to allow bypass of the carrier gas past the preconcentrator, except during the injection stage. Valve 4 and valve 5 may be combined together into a single unit such that when valve 4 opens, valve 5 closes, and vice versa.

The ports in valves 1 and 3 are matched in size and are typically larger than the ports in valves 2 and 4, which are also matched in size. Alternatively, all the valves may be the same size or different sizes. The valve ports have approximately the same dimensions in terms of hydraulic diameter as the column into which the gases are being injected. Capillary columns used in separations often range from 50 to 500 microns in diameter. If the ports are much smaller, i.e. more than one order of magnitude, the pressure drop across the valves may be too high for suitable performance. If the ports are much larger, i.e. more than one order of magnitude, the valves will be unnecessarily large and require more space and power to operate.

Figure 15E:
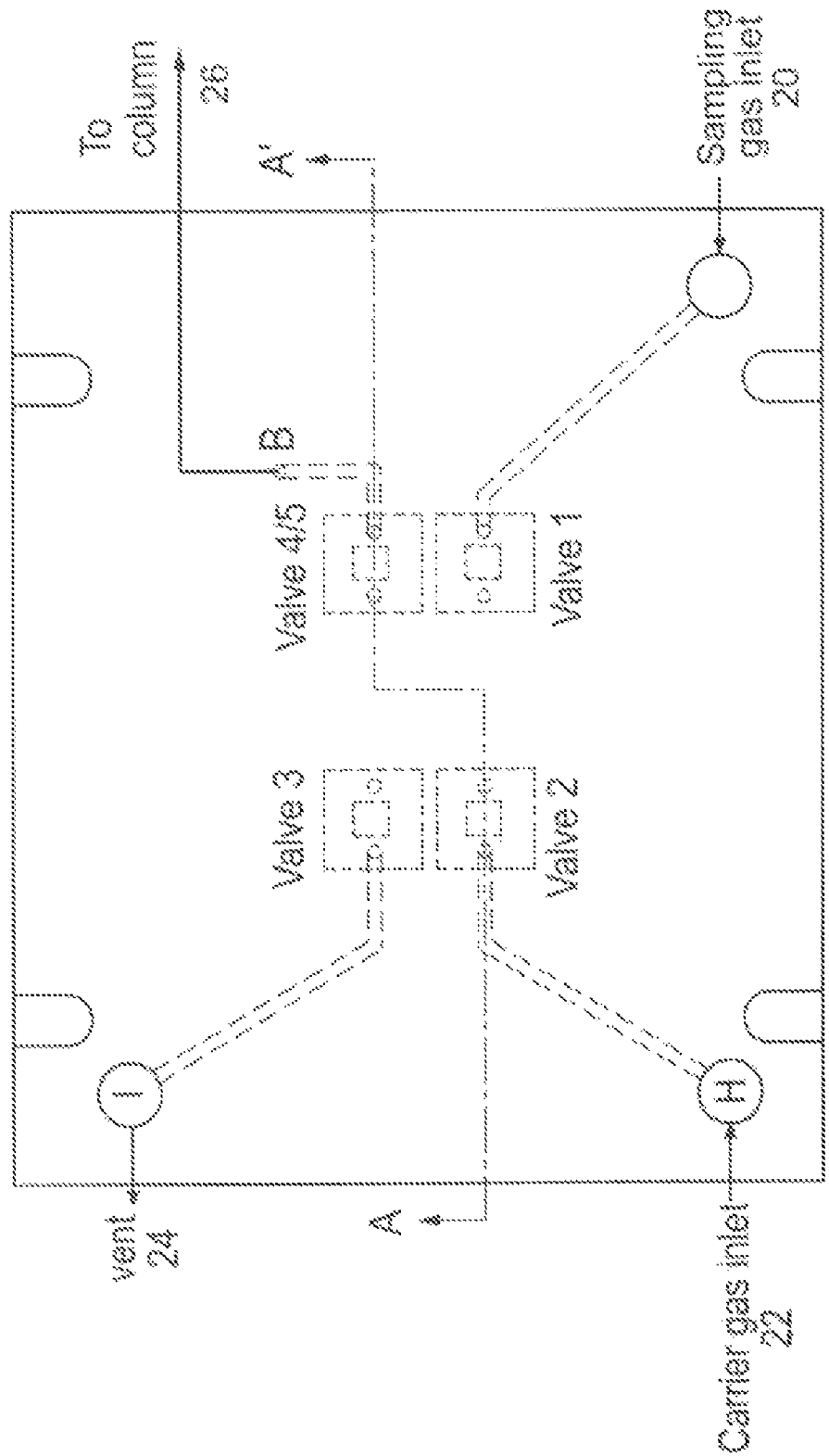
FIG. 15E is a top view of the upper electrode of the five microvalve preconcentrator of the invention showing the orientation of valves 1-5, the sample gas inlet, carrier gas inlet, vent, and the line to the GC column.
Figure 15F:
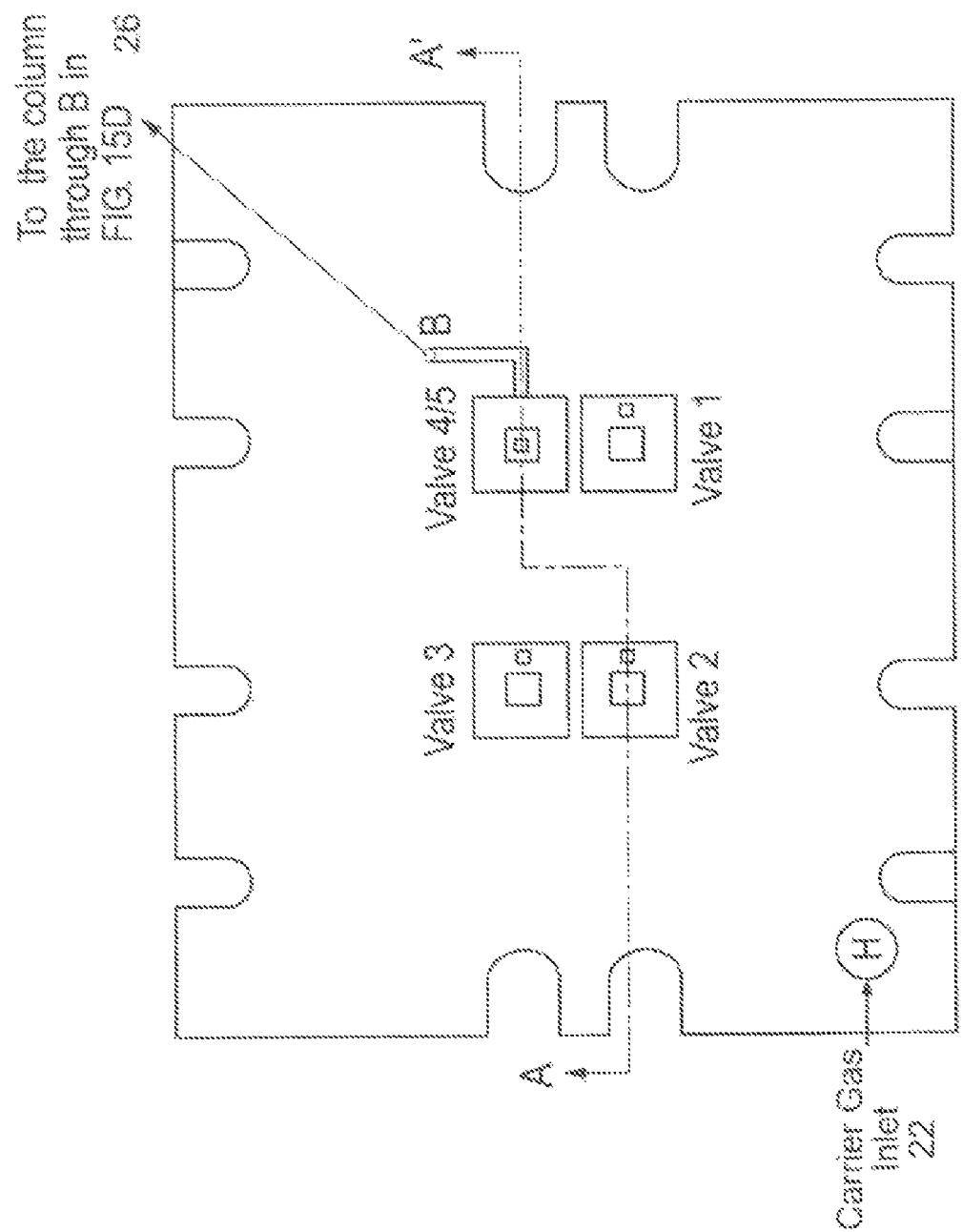
FIG. 15F is a top view of the lower electrode of the five microvalve preconcentrator of the invention showing the orientation of valves 1-5, the carrier gas inlet, and the line to the GC column.
Figure 15G:
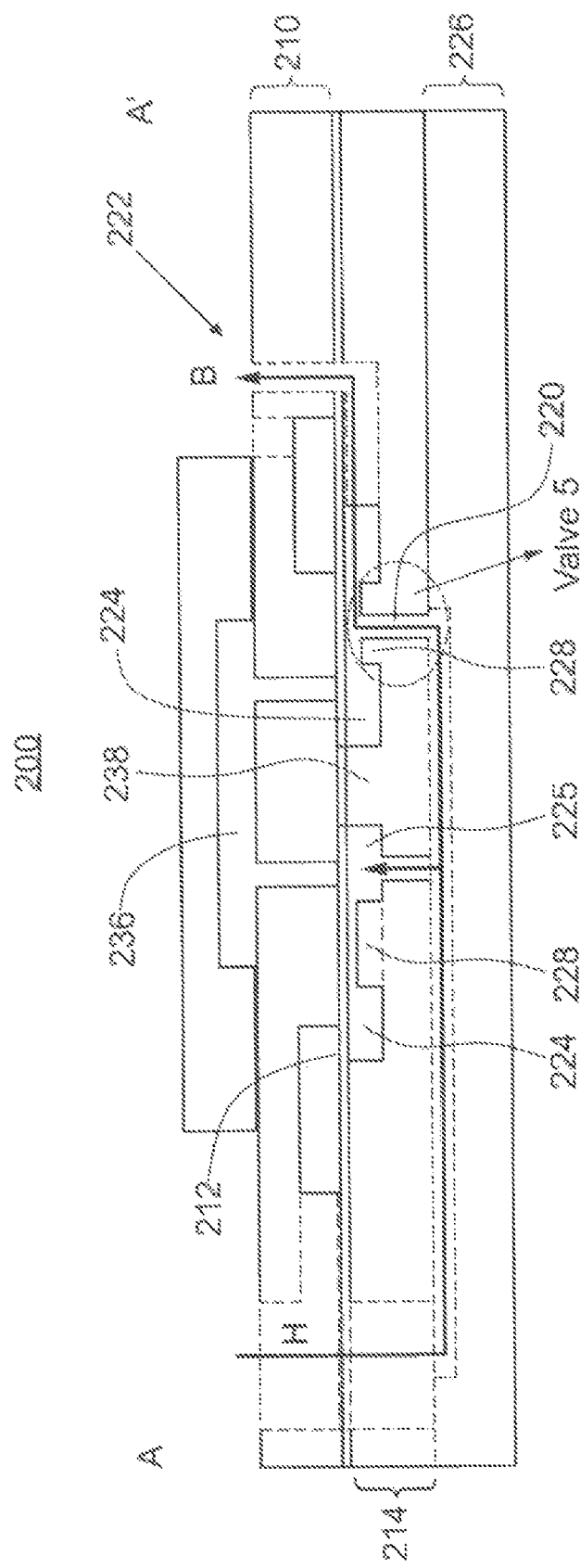
FIG. 15G is a cross-sectional diagram of the five microvalve preconcentrator of the invention taken along line AA' in FIGS. 15E and 15F showing valves 2 and 4 closed and valve 5 open.
Figure 15H:
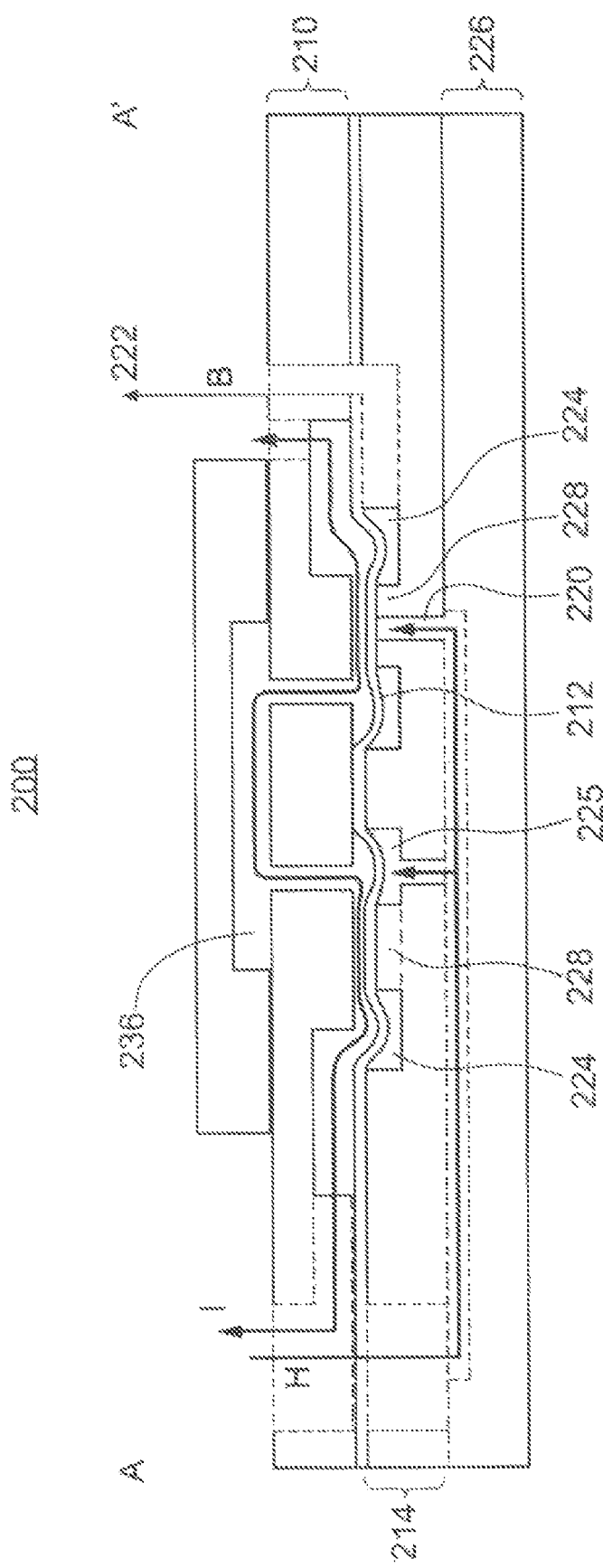
FIG. 15H is a cross-sectional diagram of the five microvalve preconcentrator similar to FIG. 15G showing valves 2 and 4 open and valve 5 closed.

As described in U.S. patent application Ser. No. 11/493,376, microvalves 1-5 of the five microvalve system may be opened and closed by an electrostatically actuated MEMS employing three electrodes. The electrodes include an upper electrode, a membrane electrode, and a lower electrode. FIG. 15E is a top plan view of the upper electrode showing the orientation of valves 1-5 the sample gas inlet 20, carrier gas inlet 22, vent 24, and the line to column 26. FIG. 15F is a top plan view of the lower electrode showing the orientation of valves 1-5, the carrier gas inlet 22, and the line to column 26.

FIGS. 15G and 15H are cross-sectional diagrams of the five microvalve preconcentrator 200 taken along line AA', as shown in FIGS. 15E and 15F. FIG. 15G illustrates that during desorption in Stage B, valve 2 and valve 4 are closed and valve 5 is open. In FIG. 15H, valve 2 and valve 4 are open and valve 5 is closed.

As illustrated in FIGS. 15G and 15H, the five microvalve system includes an upper fixed electrode 210, a movable membrane electrode 212, and a lower fixed electrode 214. The upper fixed electrode 210 defines transverse fluid ports including an inlet 220 and an outlet 222 with microfluidic channels leading to and from the ports. The membrane electrode 212 is positioned against the inlet 220 and outlet 222. While a single inlet and outlet are illustrated in the upper fixed electrode 210, that electrode may include multiple inlets and outlets which can be controlled by the membrane electrode 212. The lower fixed electrode 214 defines a microcavity 224 to accommodate deformation of the membrane electrode 212.

As shown in FIGS. 15G and 15H, the five microvalve system includes a collection chamber 236 to direct flow between microchannels valves. In addition, sorbents such as MOFs or other materials suitable as sorbents in microconcentrators may be placed inside the collection chamber 236. The microvalve is symmetrical about a post 238 that separates two separate microcavities 224. Operation on the left and right sides of the microvalve may be independent or may be synchronized as the membrane electrode 212 may have multiple metal patterns. In FIG. 15G, valve 2 and valve 4 are closed (and valve 5 is open). In FIG. 15H, the membrane electrode 212 is fully open into both of the left and right microcavities 224 and in contact with the central pads 228.

A pressure balance layer 226 is disposed at the lower portion of the lower fixed electrode 214 and provides fluid channels in communication with the inlet 220. In addition, the pressure balance layer 226 provides a pressure balance port 225 communicating with one of the microcavities 224, which provides a space into which the membrane electrode 212 may deform, as shown in FIG. 15H. The pressure balance port 225 is maintained at a pressure near that of the inlet 220 pressure. When the pressure in the pressure balance port 225 is exactly the same as the pressure on the inlet 220, the pressure is balanced and the electrostatic force needed to open the valve by overcoming the sticking force of the membrane electrode 212 on the upper electrode 210 is reduced. In addition, to counteract the pressure on the membrane electrode 212, the electrostatic force must counteract any tension in the membrane electrode 212 and the pressure differential between the pressure balance layer 226 and the outlet 222. Thus, if the pressure in the pressure balance port 225 is less than the pressure on the inlet 220, less electrostatic force is required to move the membrane electrode 212, and vice versa. In particular, the pressure balance layer 226 allows the electrostatic force required to hold the membrane electrode 212 to the upper electrode 210 to be adjusted to be zero when the pressures balance. By adjusting the pressure within the pressure balance port 225, the operational speed of the microvalves may be adjusted.

A central pad 228 reduces a gap between a portion of the lower fixed electrode 14 and the membrane electrode 212. The central pad 228 is aligned between the inlet 220 and outlet 222 and with the central portion of the membrane electrode 212 as it is most readily pulled away from its seated position. The central portion of the membrane electrode 212 is the least resilient portion as it is farthest from fixed ends of the membrane electrode 212. Also, fluid pressure from the inlet 220 is nearby. The central pad 228 reduces the gap but also allows the membrane electrode 212 to deform sufficiently into the microcavites 224 for fluid flow.

In the embodiment shown in FIGS. 15G and 15H, the five microvalve system has a normally closed position and will also fail in the closed position. Typically, the fluid will flow from the inlet 220 to the outlet 222, but different flow paths and bi-directional configurations may be made by moving the location of the inlet 220 and outlet 222 and center pad 228 as needed. The membrane electrode 212 will be attracted to the upper fixed electrode 210 or lower fixed electrode 214 depending on which side has a voltage potential applied between the membrane electrode 212 and the upper fixed electrode 210 or lower fixed electrode 214. The upper fixed electrode 210 normally touches the membrane electrode 212, blocking flow from the inlet 220 to the outlet 222. Fluid pressure from the pressure balance layer 226 assists in maintaining this position and may be sufficient to maintain the closed position in the absence of applied voltage.

When a potential, V1, is applied to the membrane electrode 212 with respect to the upper fixed electrode 210, an electrostatic force attracts the membrane electrode to the upper fixed electrode 210, and the membrane electrode 212 will seat tightly and can hold off very large forward pressures at the inlet 220 (up to more than 20 atm or higher depending on the area of the inlet 220 vs. the surrounding membrane electrode area). When the voltage is equalized between the membrane electrode 212 and the upper fixed electrode 210, and a potential, V2, is applied to the lower fixed electrode 214 with respect to the membrane electrode, an electrostatic force pulls the membrane electrode 212 away from the upper fixed electrode 210 towards the lower fixed electrode 214.

The lower fixed electrode 214 may have the central pad 228 disposed centrally in the microcavity 224. The pad 228 may be much closer (about 10 microns or less versus about 100 microns for the microcavity 224) to the membrane electrode 212 than the remaining portions of lower fixed electrode 214 that define the microcavity 224. From the closed position, the central pad 228 generates a much stronger force (up to the order of 100 times stronger) on the central portion of the membrane electrode 212 than the remaining portions lower electrode 214 do because of the increased force caused by the decreased gap. The stronger force pops the membrane electrode 212 off the upper electrode 210, creating a faster response for fluid to flow between the inlet 220 and the outlet 222. The larger volume beneath the membrane electrode 212 in the lower electrode microcavity 224 between the central pad 228 and edge of the lower electrode microcavity 224 allows the fluid to flow more easily, and reduces the squeeze film damping that occurs between the membrane electrode 212 and lower electrode 214.

The size of the central pad 228 also determines how much pressure the lower electrode microcavity 224 can have with respect to the inlet 220 and outlet 222 in order to open and close quickly. In general, the larger the central pad 228, the faster the opening time for a given applied voltage, gap distance, and pressure at the pressure balance layer 226. However, for the same conditions, the closing time will slow with increasing central pad size. Preferably, the central pad 228 and microcavity 224 are sized to produce comparable fast open and close times.

The depth of the microcavity 224 into which portions of the membrane electrode move is also determined in part by the flow rate of the fluid moving through the device. Making the microcavity 224 surrounding the central pad 228 deeper than the gap between the membrane electrode 212 and the central pad 228 creates a larger cross-sectional area for fluid to flow between the inlet and outlet, than that permitted by the distance to the central pad 228 itself. This feature prevents excessive pressure drop across the device, and permits variable flows to be controlled by adjusting the voltage. Higher voltages will pull the membrane electrode 212 further into the microcavity 224 by capacitive action without touch-mode actuation, creating a larger cross-sectional area and thus a lower pressure drop. However, if the depth of the microcavity 224 creates a much larger cross-sectional area than that of the inlet and outlet ports, the benefit of further increases diminishes. In addition, a greater depth requires a higher voltage to pull the membrane electrode 212 into the microcavity 224, requiring higher voltages to adjust the flow rates. Therefore, microcavity depths much more than 500 microns have little practical use for microscale fluid flows.

The upper fixed electrode 210, membrane electrode 212, and the lower fixed electrode 214 have substantially flat surfaces and are preferably semiconductor fabricated layers. The lack of curves and complicated shapes permits the use of semiconductor materials and semiconductor fabrication techniques.

The membrane electrode 212 may include a Cr/Au/Cr imbedded metal layer in polyimide, for example. Other flexible polymers may be used including, but not limited to parylene, Teflon®, Nafion®, Viton®, polyester, polybutylene, PDMS, and other dielectric polymers with reasonable electrical breakdown strength. In addition, other suitable polymer dielectrics for imbedding the metal layer of the membrane electrode 212 may include, but are not limited to parylene, Teflon®, Nafion®, polyester, polybutylene, and polydimethylsiloxane (PDMS).

For example, the membrane electrode 212 may be fabricated using a polyimide polymer that is spun on and cured in a low pressure environment absent of any water vapor, referred to as vacuum cure, on a separate glass carrier plate. Vacuum curing is found to substantially enhance breakdown voltage. Curing of polyimide may be performed from about 350° C. to about 450° C. The membrane electrode 212 may be at least 0.1 microns thick to avoid premature failure. For example, the membrane electrode 212 may be between 1 and 3 microns thick. Membrane electrodes 212 thicker than about 20 microns are typically too stiff for the five microvalve system, but larger devices may utilize thicker membranes.

The polyimide polymer may be metallized with thin layers of chrome, gold, and then chrome, which are then patterned to provide an electrically conductive layer within the membrane. A second polyimide polymer layer is spun on and vacuum cured over the metal layer. Holes are patterned with photoresist and etched using oxygen plasma to open up electrical contacts to the metal layer within the stack. The oxygen etches down and stops on the upper chrome layer, which is subsequently removed using a commercially available chrome etchant, exposing the gold layer to allow electrical contact. The polymer/metal/polymer sandwich stack is then transferred, aligned, bonded, and released to a silicon layer using an adhesive that may be applied to the silicon via contact printing, for example.

The bonding of the layers together enables higher pressures to be switched, since without the adhesive bonding, leakage from the inlet 220 to the outlet 222, as well to the outside environment can occur more easily. For example, the adhesive layer may be an epoxy adhesive made from a mixture of Dow Corning solid epoxy novolac-modified resin with curing agent in a 2.5:1 mass ratio, and various solvents (2-methoxyethanol 15 to 50% by mass range, anisole 15 to 50% by mass range, and PGMEA 0 to 10% by mass range, the exact amounts depend upon the adhesive layer thickness desired). Most often, the solvents are selected to modify the viscosity of the adhesive in order to achieve a thickness of 1 µm via spin coating and to achieve sharp interfaces. For a complete description of the spin coating process, see Flachsbart, B. R., K. Wong, J. M. Iannacone, E. N. Abante, R. L. Vlach, P. A. Rauchfuss, P. W. Bohn, J. V. Sweedler, and M. A. Shannon, "Design and fabrication of a multilayered polymer microfluidic chip with nanofluidic interconnects via adhesive contact printing," *Lab-On-A-Chip*, 6, 667-674, 2006.

Other adhesives may be used, including those made from biphenol compounds which cure at a higher temperature and demonstrate higher bond strengths. The key issues of the adhesive layer are that it is thin (less than 20 microns and in a range of 1-3 microns), it bonds the interfaces together to enable the device to sustain high pressures, it is aligned and contact printed on the microvalve interfaces and the membrane electrode is free to move from the upper fixed electrode 210 toward the lower fixed electrode 214, and so that the low surface energy and low surface charge trapping coatings are not affected by the adhesive layer.

The adhesive may be applied by contact printing, or any other method known in the art. Steps for contact printing may include first coating a temporary carrier with adhesive (e.g., a PDMS (Polydimethylsiloxane) stamp). The adhesive is then pressed onto the upper fixed electrode 210 or the lower fixed electrode 214 to be bonded with the membrane electrode 212 and is cured under pressure with heat. During the process, the adhesive is contact printed only onto the areas of the fixed electrodes 210 and 214 that have been patterned to not have a low surface energy film coating, which is discussed further below. The adhesive may be applied first to the upper fixed electrode 210 (by pressing the compliant PDMS stamp that has the adhesive spun onto it), and then the membrane assembly is pressed onto the upper fixed electrode 210 and is cured under pressure and heat. Then the adhesive is applied to the PDMS stamp again, and it is pressed onto the lower fixed electrode 214. The lower fixed electrode 214 is then pressed onto the upper fixed electrode 210 and membrane electrode 212 and is cured.

Solvents may be used to modify the viscosity of the adhesive in order to achieve a thickness of preferably less than 10 µm, and most preferably about 1 µm via spin coating and to achieve sharp interfaces between the those areas printed with the adhesive, and those areas without adhesive. In other embodiments, the adhesive may be applied to the membrane electrode 212.

The adhesive may bond the layers together by covalent bonding or by being physically keyed into the layer (for example, by the adhesive flowing into a pore having an opening smaller than the interior, prior to curing). Since the layers are held on the carrier plate by non-covalent forces, for example by hydrogen bonding, they can be released from the carrier plate without affecting the adhesive. The adhesive preferably forms a solid resin, such as a bisphenol, a resin-based adhesive. Examples include DER 642U, DER 662, DER 663U, DER 664U, DER 665U, DER 667 and DER 672U, all from Dow Corning. These adhesives use a hardener, such as DEH 82, DEH 84, DEH 85 and DEH 87, all from Dow Corning. The adhesive may also be an epoxy adhesive mixture of solid epoxy novolac modified resin with curing agent in a 2.5:1 mass ratio.

A solvent may be added to the adhesive to control the viscosity, for example 2-methoxyethanol (15 to 50% by mass), anisole (15 to 50% by mass), and PGMEA (0 to 10% by mass) range. The layers may be bonded by heating and applying pressure to cure the adhesive, for example at 130° C. and 5.2 MPa under vacuum for 10 minutes. The temporary adhesive carrier is an elastic polymer, such as a 3 mm thick 50 mm diameter PDMS disk. The carrier plate may be released from the layer using a hot water bath at approximately 50° C. for 5 minutes. The adhesive may be given a final cure, for example by heating the completed device for 12 hours at 130° C. Then the silicon layer may be bonded to the membrane using the same process.

The resulting microvalve is then placed in a plastic package developed to apply pressure and electrical potentials using standard fittings. The plastic package may also be used to hold the pieces together instead of bonding, particularly for lower operating pressure devices.

The upper fixed electrode 210 and the lower fixed electrode 214 may include a semiconductor and its oxide with an additional nitride film, for example. The nitride film may only be a few monolayers thick. This film provides low surface charge trapping and is preferably used with a low surface energy film, e.g., Teflon®, and such a thin multi-layer is effective both in preventing stiction and surface charge build up. In another embodiment, a dielectric oxide and nitride monolayers may be used to isolate the metal layer of the membrane electrode 212. Additionally, low surface charge trapping and low surface energy coatings may be added to the electrodes during semiconductor fabrication techniques.

The microcavity 224, central pad 228, upper fixed electrode 210, and membrane electrode 212 have flat surfaces. The flat surfaces are readily fabricated by conventional semiconductor microfabrication techniques, without resort to machining steps. Machining steps, such as those required for curved or arched surfaces increase the lowest possible size limit and do not readily translate to mass fabrication techniques.

In the five microvalve system, voltage rises rapidly as the gap between the central pad 228 and the membrane electrode 212 increases. High voltages may create difficulty because they create a large electric field when the microvalve opens and the membrane electrode 212 touches the central pad 228. With a gap of about 250 microns, the electric field exceeds the breakdown voltage of most polymers. For example, the electric field may be below 200 V/micron and preferably below 50 V/micron to prevent long-term degradation of the membrane. That limits the distance to be below about 150 microns and preferably below about 25 microns. Fabrication may be difficult if the distance is less than about 1 micron. 0.1 microns represents a practical lower limit with conventional MEMS fabrication tools.

The time response of the microvalve is determined by the specific application, in particular which are much more important factors in gas chromatograph injector microvalve, chemical analysis, and etc. The important factors can be injector pressure (which depends on the pressure across the microvalve), flow rate (which depends on both the pressure across the microvalve, the microvalve orifice size, the membrane electrode 212 thickness and size), and the microcavity 224 size, the voltage across the membrane electrode 212, and the current through the microvalve (which depends on the applied voltage, the capacitance and resistance of the microvalve and circuit). Pressure from the pressure balance layer 226 also factors into response time. The balance pressure is added to balance pressure on both sides of the membrane electrode 212, thereby decreasing the net pressure across the membrane electrode 212 to increase both the pressure the microvalve can handle and speed of opening and closing. The pressure can be adjusted to be different on both sides of the membrane electrode 212 to apply a pneumatic actuation in addition to the electrostatic force, to control open and closing times, as well as to determine if the device fails open or closed.

This allows, for example, the pneumatic action across the microvalve to be adjusted as desired to create faster opening microvalves (by reducing the pressure in the pressure balance layer 226 on the lower electrode 214 side) or faster closing microvalves with lower leakage of fluid from the inlet 220 to the outlet 222 (by increasing the pressure at the pressure balance layer 226 on the lower electrode 214 side). For the embodiment shown in FIGS. 15G and 15H, even when the pressure is initially equal on both sides of the membrane when the microvalve is closed, once fluid starts flowing from the inlet 220 to the outlet 222, the pressure acting on the upper side of the membrane electrode 212 will decrease due to Bernoulli forces and the pressure at the pressure balance layer 226 will be higher than at the inlet 220, acting to help close the microvalve. A regulator and/or orifice may also be added to either the inlet 220, outlet 222, or at the pressure balance layer 226 to adjust the pneumatic actuation to the value desired for other embodiments of this invention.

Another embodiment of a micropreconcentrator of the invention features high surface area micropost structures that may be coated with sorbents to form a micropreconcentrator. Microposts are three-dimensional structures that increase the surface area of the substrate they are formed on due to their geometry. In particular, the microposts may be cylindrical in shape and thus have surface area along their cylindrical wall and top.

Figure 19A:
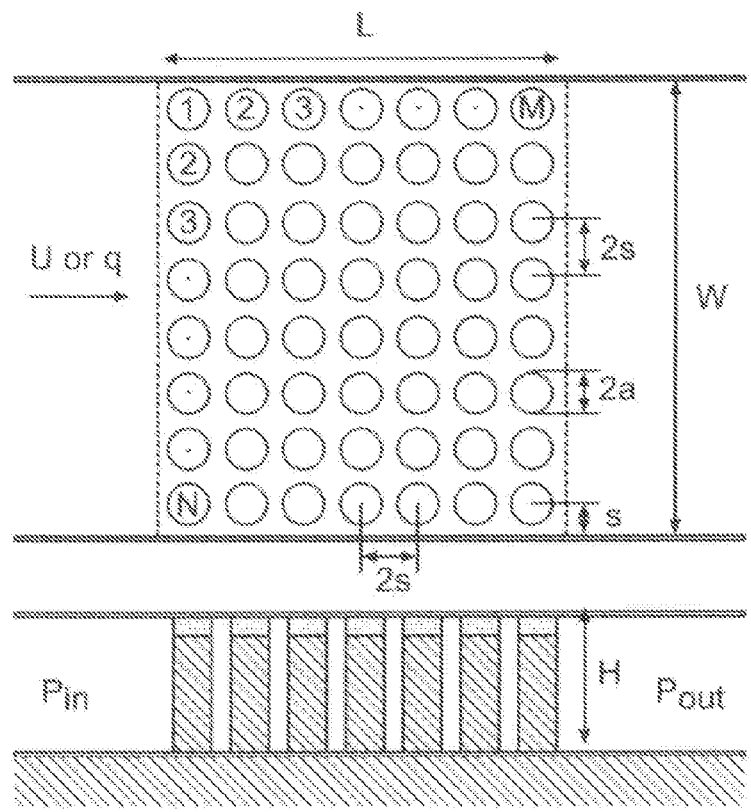
FIG. 19A is a schematic diagram of a microchannel filled with an N by M array of microposts constructed according to the principles of the invention.
Figure 19B:
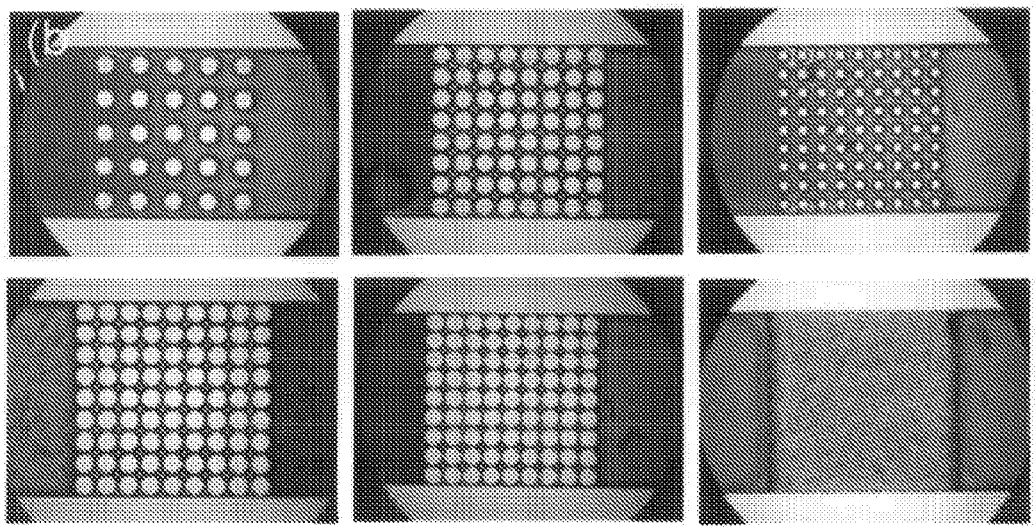
FIG. 19B shows optical microscope images of exemplary silicon micropost arrays constructed according to the principles of the invention.

Micropost structures are arranged in an array within the micropreconcentrator and they are coated with a sorbent. For example, in one embodiment of the invention, micropost arrays may be used to increase the surface area of a sorbent when they are deposited inside the surface of a collection chamber of a microvalve preconcentrator of the invention, as described in detail below. Alternatively, microposts may be deposited on intermediate structures and then placed inside the collection chamber. The microposts may be aligned in a staggered configuration, for example, as shown in FIGS. 19A and 19B, below, or in other spacing configurations. The sorbent coating allows the microposts to collect and trap analytes that pass through the micropost array. Since the surface area of a micropost array is itself very high, this embodiment of the invention can be used with sorbents that have lower surface areas than MOFs.

The micropreconcentrators of the invention may release molecules in milliseconds and may selectively provide high gain (about 1000 times) for analytes of interests and little gain for common interferents, depending on the sorbent used. The micropost arrangement has been developed to provide a comparable surface-area-to-volume-ratio to microporous media, but with a shorter effective path length and lower pressure drop per unit length. A smaller pressure drop in the micropreconcentrator implies faster response time and less power consumption.

Figure 16A:
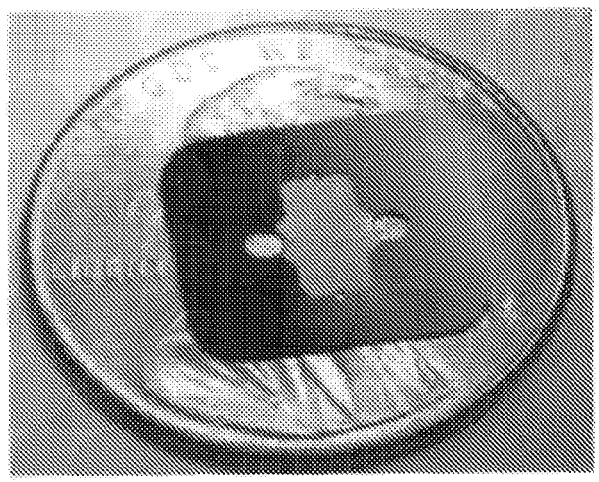
FIG. 16A is a photograph of the micropreconcentrator constructed according to the principles of the invention on top of a penny.

FIG. 16A is a photograph of a micropreconcentrator constructed according to an embodiment of the invention on top of a standard U.S. penny. As is evident from the picture, the entire micropreconcentrator is a fraction of the size of a penny and has a correspondingly low volume, which makes it highly suitable for use in a micro GC.

Micropost structures are formed on a substrate using any method known in the art to increase its surface area and allow higher sorption of the analyte. Using a highly controlled inductively coupled plasma deep reactive ion etching (ICP-DRIE) process, for example, highly anisotropic structures can be etched into the silicon. The ICP-DRIE process may employ a well-known $SF_6$ etching gas step followed by a $C_4F_8$ passivation step, which are repeated for many cycles until the desired depth is achieved. In addition, silicon microposts may also be grown using well-known thermally-initiated chemical vapor deposition processes on catalysts, such as NiFe or Pd/Au patterned or deposited on the silicon substrates.

Figure 16B:
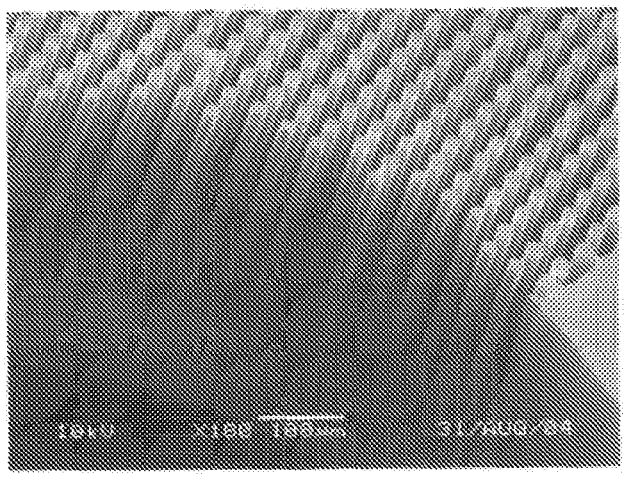
FIG. 16B is an SEM photograph of silicon microposts that may be employed in a micropreconcentrator constructed according to the principles of the invention.

For example, using any method known in the art, densely packed micron diameter silicon posts of predetermined dimensions may be formed uniformly over a micropreconcentrator, such as shown in the SEM photograph of FIG. 16B. The microposts may then be doped and electrochemically etched to produce nanometer size etch pits within the microposts. These nanometer size etch pits further enhance the inherently high surface area of the microposts without increasing the pressure drop. The combination of high sorbent capacity due to high surface area and a very small volume allow for high-gains in concentration that improve sensitivity of analyte detection.

Figure 16C:
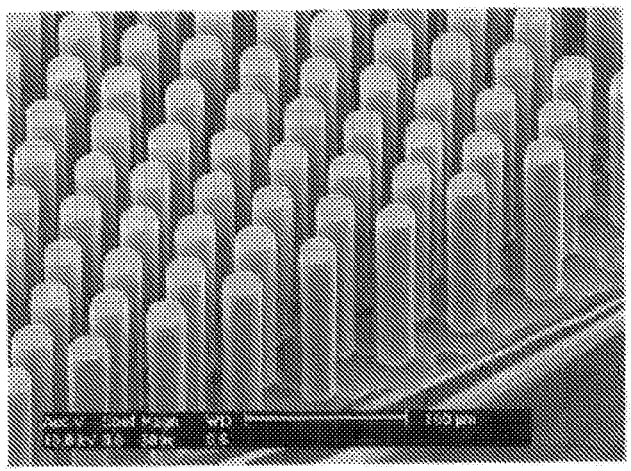
FIG. 16C is an SEM photograph of microposts of the invention coated with sorbents.

The microposts may be coated with a wide range of sorbents such as low surface area compounds including polymers. In addition, high surface area compounds such as MOFs may be coated on the microposts, although the use of MOFs is not required since the micropost array itself produces very high surface areas for enhanced sorption, as described earlier. FIG. 16C is an SEM photograph of silicon microposts coated with sorbents according to the invention. Thus, the micropost structures of the invention can provide high surface area instead of requiring the sorbent to have an inherently high surface area.

Sorbents may be coated on the microposts by any method known to one skilled in the art. One particularly novel and advantageous coating method has been developed by Applicants to coat the micropost structures with selective sorbents, and is disclosed in U.S. Provisional Patent Appl. No. 60/828,266 (filed Oct. 5, 2006, in the name of inventors Mark A. Shannon, et al.), the disclosure of which has been incorporated by reference herein in its entirety. This method involves surface modification to covalently attach preformed sorbents to a micropost surface. For example, a polymer layer may be deposited on the micropost by providing an anchor on the micropost surface to attach the polymer by nucleophilic substitution. As a result, adherent polymer layers provide the ability to control fluid transport characteristics within micro- and nano-channels.

This surface modification method involves four main steps. First, surface activation of the preconcentrator substrate with water-vapor plasma introduces surface hydroxylation that is chemically bonded to the surface. Next, treatment of the plasma-treated substrate with a solution containing trichlorosilane or trimethoxysilane forms a functional surface layer that reacts with the hydroxyl groups. The reaction between the trichlorosilane or the trimethoxysilane, or any other reactive silane forms a covalently bonded silicon compound at the surface of the preconcentrator. Bromoalkyltrichlorosilane may be used as the initial functional surface layer, for example.

After this functional layer is formed, surface azides are then introduced via a $S_N2$ nucleophilic substitution with the azides. Finally, functionalized alkynes may be added to modify the surface through to 1, 2, 3,-triazole linkages. This method allows rapid and facile modification of a wide range of surfaces including glass, silicon, silicon oxide and nitride, alumina, and other ceramics. The key step for the substrate material is that it can be hydroxylated. Preconcentrator substrates can also be made from polymers that may include, but are not limited to, polymethyl methacrylate (PMMA), polyethylene glycol (PEG), polyamidoamine (PAMAM), polyimide, polyethylene, polypropylene, polystyrene, polyoxymethylene, polyethylene terephthalate (PET), and silicone rubber.

Typically, preconcentrators with high-surface area to volume ratios also have high pressure drops across the system, which require more power to move gases through it. Such systems also often have relatively long sorption and desorption times, leading to longer and less sensitive detection by a GC or other analytical instrument. The pressure drop across the micropreconcentrator of this invention, however, is very small due to the low fluid resistance enabled by its open structure. The micropost packing density increases continuously as the diameter of the posts scales down to nanometer size, but the pressure drop does not increase.

These unique features allow the micropreconcentrator to have a very small volume while maintaining low power consumption and shorter analysis cycles and still providing high concentration gain and higher sensitivity of the GC. In particular, according to one embodiment, the micropreconcentrator of the invention may consume only 1 μl of sample for each analysis and is able to complete at least 4 analyses per minute using 40 cc of analyte. Further, only one (1) J is required for each analysis, thus minimizing the power consumption.

This design also allows the micropreconcentrator to have low dead volume, which provides a sharper desorption peak and accordingly boosts the performance of the microprecon-centrator preconcentrator and the GC system. To minimize the volume of the micropreconcentrator and achieve low power consumption, short analysis cycles, and high gain, the dimensions of the microposts and the geometry of channel may be carefully designed. In particular, design parameters including the radius-half spacing ratio, β, and the aspect ratio, which will be defined later, may be optimized according to the principles of the invention. Using these design parameters, a dimensionless objective function (DOF) may be derived to minimize the pressure drop while maximizing the surface area-to-volume ratio for a given channel geometry of the micropost-filled preconcentrator. As a result of the optimization achieved by the invention, the number of molecules sorbed and desorbed for a given flow rate and channel geometry is maximized. Applying the optimization techniques of the invention, it was found that as the number of microposts increases for a given channel size, a higher surface area-to-volume ratio is available for a fixed pressure drop.

Figure 17:
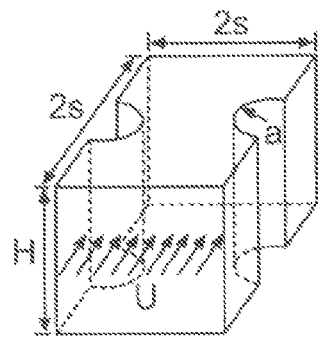
FIG. 17 is a schematic diagram of a unit cell in a micropost array that is used for modeling fluid flow according to the principles of the invention.

To begin the mathematical optimization of the surface area-to-volume ratio for a given pressure drop according to the invention, the dimensions of the microposts and geometry of the channel must be considered. FIG. 17 is a schematic diagram of a unit cell in a square micropost array includes cylindrical microposts with circular cross section. As shown in FIG. 17, each micropost has a radius of a, a half-spacing between adjacent posts of s, and a height of H. The aspect ratio, AR, is defined as the ratio of the height, H, of the posts to the half spacing, s, between adjacent posts, which thus may be expressed as H/s.

The pressure drop can be expressed solely as a function of a dimensionless parameter, β (=a/s), which is the ratio of the radius of each post to the half-spacing between two adjacent posts. β is then used to estimate the drag per unit length of the cylinder. Two independent models from literature, the lubrication Stokes model and the Oseen approximation of the Navier-Stokes equation for fluid flow, were used by Applicants to predict the pressure drop across the micropost-filled channels with low Reynolds number flow past a square array of the circular cylinders, as shown in FIG. 17. The model was extrapolated from one unit cell to arrays of unit cells.

In the first mathematical model, Keller (Joseph B. Keller, "Viscous flow through a grating or lattice of cylinders", J. Fluid Mech. 18 (1964) 94-96) assumed that most of the flow resistance came from the narrow gap between adjacent cylinders and applied the lubrication model derived from the Navier-Stokes equation to determine the flow in the gap. With a few more approximations, the normalized drag per unit length ($\hat{D}$) on each cylinder can be then expressed as a function of β in Equation 1 below:

$$\hat{D} = \frac{D/H}{\mu U_{cell}} = \frac{12\beta}{(1-\beta^2)^2} + \frac{18\beta^2}{(1-\beta^2)^{5/2}}\left(\arctan\left(\frac{\beta}{\sqrt{1-\beta^2}}\right) + \frac{\pi}{2}\right) \quad (1)$$

where $U_{cell}$ is a uniform upstream velocity per unit cell and μ is fluid viscosity. Equation 1 is more accurate as β approaches unity. Since a large value of β means a closely spaced array of cylinders, the viscous effect of the flow on a cylinder readily interferes with its adjacent ones and dominates over the inertia effect.

As β gets smaller, however, the inertia term in the Navier-Stokes equation becomes more significant and can no longer be ignored. Thus, others skilled in the art have used Oseen's linearized equations of motion to study a 2-D steady flow past an array of cylinders at low Reynolds numbers. (See, e.g., K. Tamada and H. Fujikawa, "The steady two dimensional flow of viscous fluid at low Reynolds numbers passing through an infinite row of equal parallel circular cylinders", Quart. J. Mech. Appl. Math., 10 (1957) 425-432) and H. Hasimoto, "On the periodic fundamental solutions of the Stokes equations and their application to viscous flow past a cubic array of spheres", J. Fluid Mech., 5 (1959) 317-328). As both the Tamada and Fujikawa method and the Hasimoto method suggest solutions that coincide relatively well, one of their approaches can be taken as an example. Applying the Tamada and Fujikawa method, the Applicants applied Oseen's equations and calculated the drag per unit length of a cylinder in the form of power series function of β, as shown below in Equation 2.

$$\hat{D} = \frac{8\pi}{\Lambda_0} + O(Re^2) \quad (2)$$

where $$\Lambda_0 = 1 - 2\ln(\pi\beta) + \frac{1}{6}(\pi\beta)^2 - \frac{1}{144}(\pi\beta)^4 + \frac{1}{1080}(\pi\beta)^6 + O((\pi\beta)^8)$$

Figure 18A:
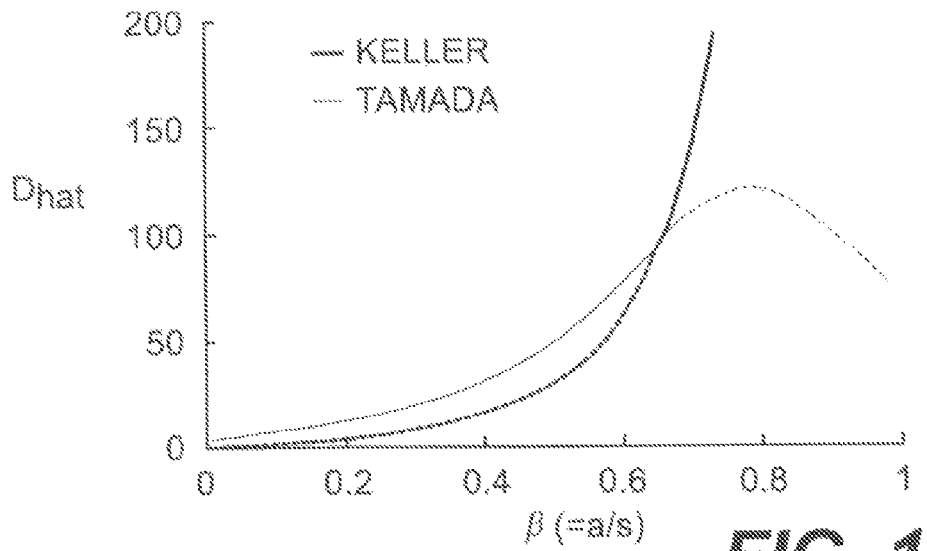
FIG. 18A shows curves for the normalized drag per unit length as a function of the dimensionless parameter, $\beta$, that may be employed in modeling the unit cell of FIG. 15.

This solution is true only for small β values. FIG. 18A shows curves for the normalized drag per unit length as a function of the dimensionless parameter β. As the normalized drag per unit length on a cylinder is plotted with β, as shown in FIG. 18A, both solutions correctly predict the limiting case of β approaching zero. However, in the other extreme case (β→1) only Keller's model shows the diverging trend in $\hat{D}$. The intersection of two curves at β~0.65 is shown in FIG. 18A and the valid region of each model is indicated by a solid line.

Using these drag models, the calculation of the surface area-to-volume ratio (SA/V) per unit cell is straightforward except for whether or not the upper and lower bounded walls should be included in calculating the surface area of the unit cell. The SA/V per unit cell is a function of not only the radius-half spacing ratio, β, but also the aspect ratio of the channel, i.e., AR (=H/s). From FIG. 17, the SA/V per unit cell can be written as Equation 3 below.

$$SA/V_{cell} = \frac{2a\pi H + 2(4s^2 - \pi a^2)}{4s^2 H - \pi a^2 H} = \frac{1}{H}\left(\frac{2\pi\beta AR}{4 - \pi\beta^2} + 2\right) \quad (3)$$

Note that the SA/V per unit cell has a unit of inverse length and the term '2' in the bracket is the contribution from the top and bottom of the bounded walls.

An objective function for the minimal pressure drop and maximal surface area-to-volume ratio is defined by dividing the normalized drag per unit length on a cylinder, $\hat{D}$, by the SA/V per unit cell. This function is not yet dimensionless so further manipulation is required to obtain a unitless objective function. The pressure drop per unit cell, $\Delta P_{cell}$, can be written according to Equation 4 below.

$$\Delta P_{cell} = \frac{D}{2sH} \quad (4)$$

Setting $\hat{D}$ equal to in $f(\beta)$ in Equation 1 and Equation 2 and plugging Equation 4 into Equation 1, the normalized pressure drop per unit cell is written as in Equation 5 below.

$$\frac{\Delta P_{cell}}{\mu U_{cell}} = \frac{f(\beta)}{2s} \quad (5)$$

Finally, a dimensionless objective function (DOF) can be written as the ratio of the normalized pressure drop to the SA/V in a unit cell, as shown in Equation 6 below:

$$DOF = \frac{\Delta P_{cell}/\mu U_{cell}}{SA/V_{cell}} = \frac{ARf(\beta)}{4\pi\beta AR/(4-\pi\beta^2)+4} \quad (6)$$

with $f(\beta)$ being $\hat{D}_{Keller}$ for $\beta > 0.65$ and $\hat{D}_{Tamada}$ for $\beta < 0.65$.

Figure 18B:
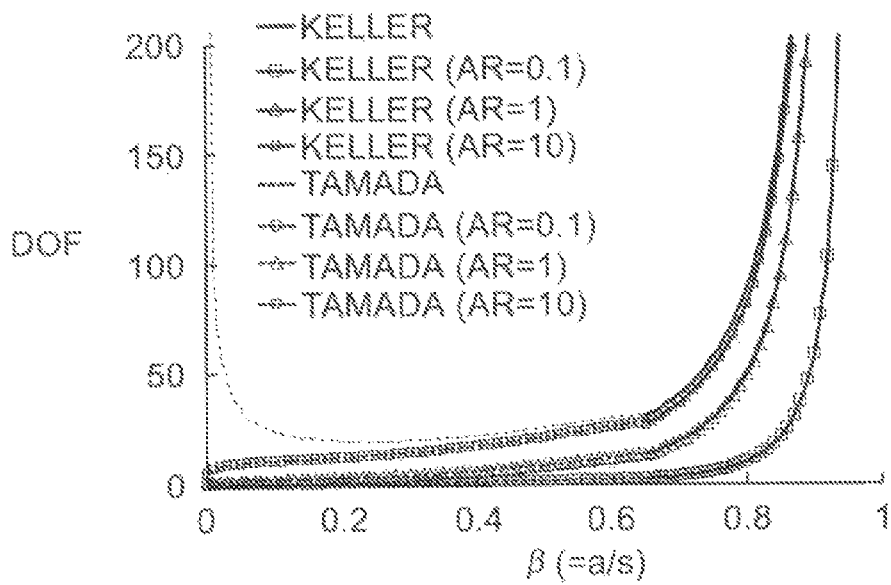
FIG. 18B shows a family of curves of the dimensionless objective function (DOF) vs. $\beta$ for a range of aspect ratios of the micropost, that may be employed in modeling the unit cell of the invention.

FIG. 18B shows a family of curves of the DOF vs. β for a range of aspect ratios. The DOF curves with higher aspect ratios (represented by darker thin lines) asymptotically approach the thick solid line of the DOF with an infinite aspect ratio, where the contribution to the SA/V per unit cell from the top and bottom of the walls becomes negligible, and Equation 6 can be reduced to Equation 7 below.

$$\frac{\Delta P_{cell}/\mu U_{cell}}{SA/V_{cell}} = \frac{(4-\pi\beta^2)f(\beta)}{4\pi\beta} \quad (7)$$

An optimal design of the microposts may be achieved if β is selected such that DOF is at a minimum for a given desired surface area to volume ratio, which is determined by the desired gain of the preconcentrator. The smaller DOF becomes, the less pressure drop is present, or the more SA/V available per unit cell. FIG. 18B demonstrates that all DOF curves monotonically increase except the infinite aspect ratio case in which a minimum exits. According to these findings, arrays of posts with nanometer diameters and spacing can be an optimal structure for a micropreconcentrator with high surface area yet small flow resistance.

To experimentally verify the results of the analytical optimizations, a number of millimeter channels filled with DRIE-etched microposts of various β values were fabricated. FIG. 19A is a schematic diagram of a microchannel filled with an N by M array of microposts. FIG. 19A shows the configuration of 2-D fluid flow across the channel and an N by M array of microposts. The diameter of the microposts ranges from 200 μm to less than 10 μm, and the spacing between them from 400 μm to 40 μm. In these experiments, $AR_0=0.1$. These dimensions are chosen to allow β to vary between 0.2 and 0.95 and are recorded using the calibrated optical microscope to account for any discrepancy that may arise during the lithographic and etching processes. FIG. 19B shows optical microscope images of the exemplary silicon (Si) micropost arrays constructed according to principles of the invention. The optical microscope images of an array of the microposts with different β values are shown FIG. 17B. In total, 27 devices were fabricated on a 100 mm diameter Si wafer (Silicon Quest International®, N-type <100>, 1-10 Ω·cm) using a conventional double-sided photolithography and subsequent DRIE etching (Plasma-Therm® SLR770). Each Si die was etched to a uniform depth (c.a. 200 μm) and bonded with a 1 mm-thick microscope slide that had been cut in the same size of a Si die. A thermally curable epoxy based adhesive was transferred to a Si die via the contact printing, and a glass top was then pressed down to the adhesive-coated Si die on 130° C. hotplate for a gas-tight seal.

All bonded samples were housed in the SLA packages that provide a leak-free fluidic connection to via holes in a Si die. High purity $N_2$ gas (S. Smith®, 99.9%) from the high pressure source tank was filtered and fed to the flow meter (MKS®, 2179A) which regulates flow rate of the gas via the computer software of the data acquisition system. Two commercial pressure sensors (Omega Engineering Inc.®, PX142) that have a linear response up to 7000 Pa with a 5 V span (meaning the resolution of about 1.4 Pa/mV) were placed in the inlet and outlet of the SLA package to measure pressure at each point. First, the pressure drop ($\Delta P = P_{inlet} - P_{outlet}$) in all 24 samples was measured individually at a flow rate of 10 sccm. Then, the pressure drop across a dummy sample of the same channel dimensions but with no micropost structures was measured as a control and later subtracted from the previous pressure drop measurements of the channel with micropost structures. Therefore, $\Delta P_{corrected} = \Delta P - \Delta P_{control}$. The pressure drop measurements were repeated five times to provide a statistical basis on the error analysis.

The Reynolds number of the flow depends on which dimension is chosen as a characteristic length for calculation. A diameter of each post, a center-distance between two adjacent posts, and the height of the channel may all be the characteristic length. With 10 sccm of a fixed flow rate, the Reynolds number depending on the choice of the characteristic length ranges from 0.1 to 0.5, in which the Stokes approximation is valid.

Since the number of microposts varies sample by sample along with different β values, a direct comparison of these pressure drop measurements with the analytical solutions would not be appropriate. The pressure drop per unit cell, i.e., the contribution of each micropost to the overall pressure drop, can be calculated by dividing the corrected pressure drop by the number of the microposts in the channel. From FIGS. 15 and 19A, the pressure drop in the cell can be written as shown below in Equation 8.

$$\Delta P_{cell,measured} = \frac{\Delta P_{corrected}}{NM} \quad (8)$$

Figure 20A:
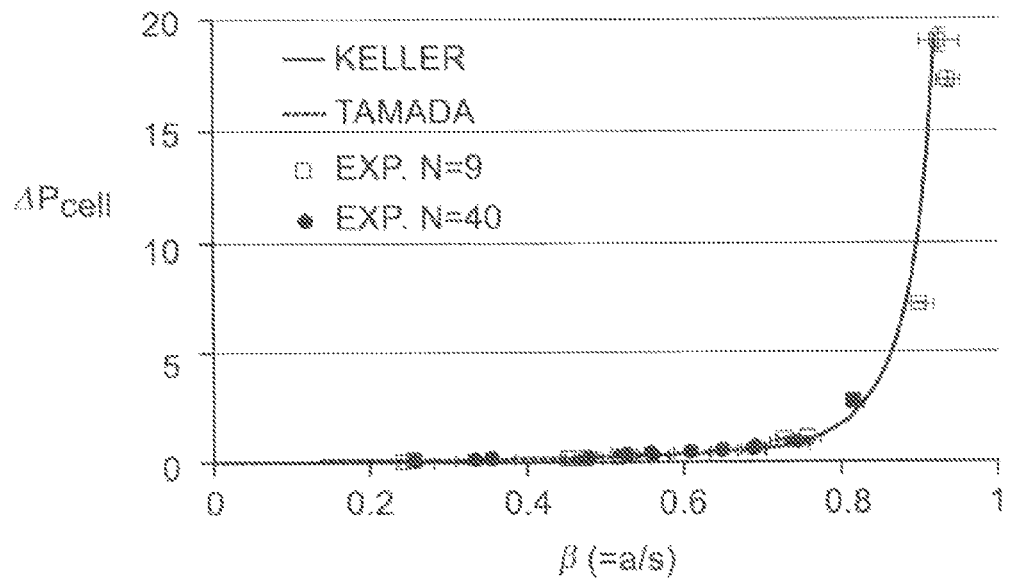
FIG. 20A is a graph of the pressure drop per unit cell of the micropost array of the invention vs. the dimensionless parameter $\beta$.
Figure 20B:
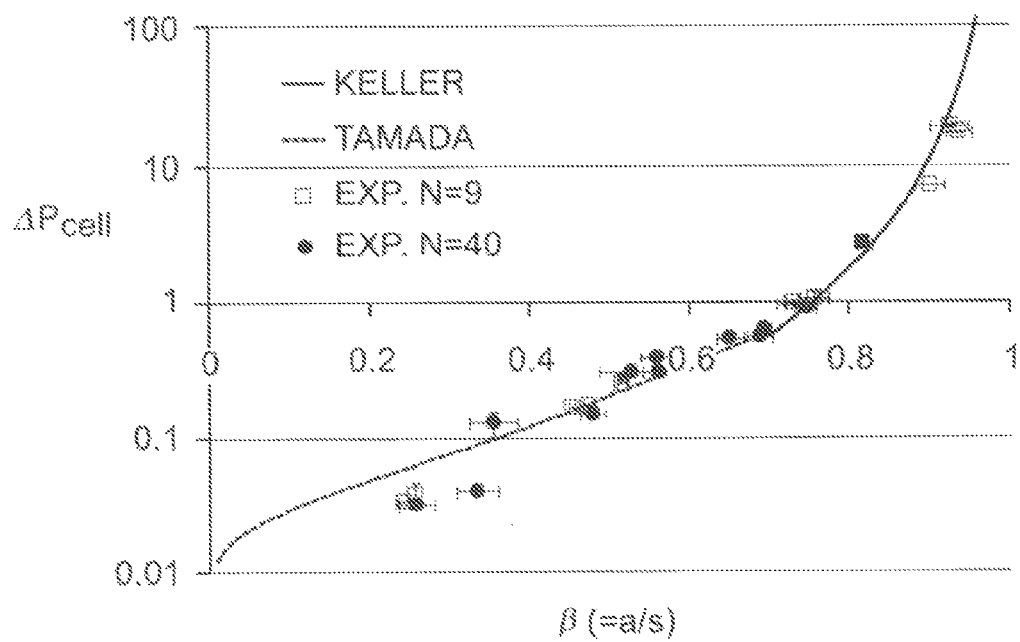
FIG. 20B is a semi-logarithmic version of FIG. 18A.

The measured pressure drop per unit cell can be directly compared to the theoretical solutions using the following relationship, derived from Equation 5, as shown below in Equation 9.

$$\Delta P_{cell} = \mu U \frac{f(\beta)}{W} \quad (9)$$

where $U=U_{cell}N$. FIG. 20A and FIG. 20B show that each theoretical model well represents the experimental results for its applicable β range.

For β greater than 0.65, the agreement of the pressure drop data to Keller's model using the Stokes equation suggests that the viscous effect is indeed prevailing in the pressure drop of the closely spaced posts. As β gets smaller, both viscous and inertial components of the pressure drop in the channel become important. Therefore, Tamada's solution to Oseen's equation better predicts the pressure drop behavior for lower β values. It is evident from FIG. 18A that Keller's model underestimates the pressure drop for β less than 0.65 because it includes the viscous component of the flow only. Due to the fabrication challenges faced when etching very small diameter post structures, samples with β<0.2 were unavailable.

When an array of the posts is considered as shown in FIG. 19A, it is more instructive to express the SA/V per unit cell and DOF in terms of the number of posts in a column, N, rather than aspect ratio, AR. Equation 3 and Equation 6 can be rewritten using the geometrical identities, W=2sN and L=2sM (see FIG. 19A), $$SA/V_{cell} = \frac{1}{H}\left(\frac{4\pi\beta NAR_0}{4-\pi\beta^2} + 2\right) \quad (10)$$

$$FOM = \frac{AR_0 N f(\beta)}{4\pi\beta AR_0 N/(4-\pi\beta^2) + 2} \quad (11)$$

where $AR_0$=H/W, fixed by the geometry of the channel.

Figure 21A:
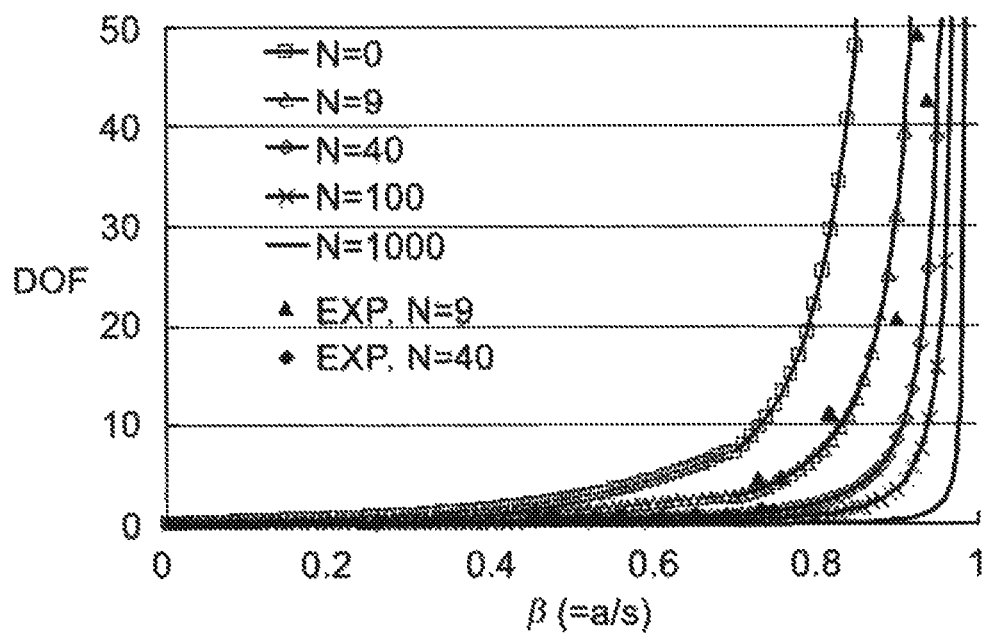
FIG. 21A is a graph that shows that each theoretical fluid flow model for the unit cell corresponds to the experimental results for its applicable range.
Figure 21B:
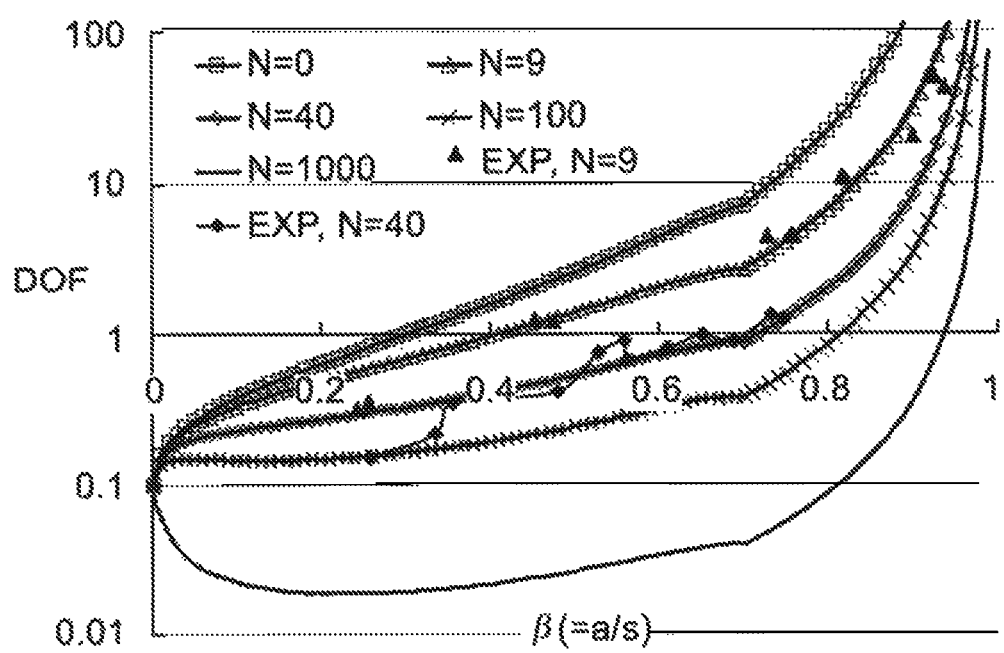
FIG. 21B is a semi-logarithmic plot of the graph shown in FIG. 19A.

Note that the pressure drop per unit cell is independent of the number of posts, N, and a function of only β. The dependence of the DOF on N stems purely from SA/V. Therefore, the N dependence of the DOF disappears as N goes to infinity, and Equation 11 is reduced to Equation 7. As shown in FIG. 21A and FIG. 21B, the DOF is plotted with β for a wide range of N. The solid lines represent the calculations based on the Keller and Tamada models, and data points for two different N values exhibit basic agreement of the calculated DOF.

In sum, based on the Keller and Tamada models, the mathematical findings indicate that the DOF decreases with increasing N. Therefore, for fixed β value and channel geometry, microposts should be packed densely for minimal pressure drop and maximal surface-area-to-volume-ratio. In order to increase N with a fixed β, the size of the post has to be smaller and smaller.

In another embodiment of the invention, microposts may be disposed inside the collection chamber of a MEMS valve system, such as the five microvalve system used as a micropreconcentrator, as described earlier. For example, the microposts may be disposed on the inner walls of the collection chamber so that the sample gas can pass through it. The microposts may line the microchannel in which the sample gas passes through from valve 1 to valve 3, while loading the preconcentrator.

More particularly, FIG. 22A is a cross-sectional schematic view of a micropreconcentrator 300 constructed according to principles of the invention housing a MEMS valve system incorporating microposts. In this embodiment, the micropreconcentrator is located between two microvalves that open and close to admit sample gas and carrier gases that are routed from a trap and purge system shown in FIG. 14. As shown in FIG. 22A, the carrier gas 312 enters the system through the carrier gas inlet 314. Sample gas enters the system through the sampling gas inlet 316 and is directed to collection chamber 310, which contains microposts constructed according to the principles of the invention as shown in FIG. 22B described below. The membrane electrode 318 is electrostatically actuated to allow flow through a first valve 320 and a second valve 322. For desorption, a microheater 324, such as a nickel-chromium (NiCr) microheater is positioned near the collection chamber 310, which contains microposts constructed according to the principles of the invention as shown in FIG. 22B. Desorbed analyte flows to the column of an analytical instrument through the outlet 326.

FIG. 22B is an SEM photograph that provides an expanded view of the microposts 328 present in the collection chamber 310. The design of the microposts and the micropost array may be optimized according to the principles discussed above to produce a high surface area to volume ratio and a low pressure drop across the micropost array. The microposts may be coated with a suitable sorbent for collection of analyte using any method known in the art, including those discussed above. With this configuration, use of a high surface area sorbent, such as a MOF, is not necessary since the microposts provide an inherently high surface area for the analyte to be collected in the collection chamber. However, the chamber may also be designed to have a lower density of microposts to permit MOF's to be inserted into the preconcentrator.

In addition to the advantageous design and optimization of microposts in the micropreconcentrator discussed above, preconcentrators of the invention may also utilize catalytic heater technology for desorbing the analyte to substantially reduce the electricity needed in the device, such as a nickel-chromium microheater known in the art. Hydrides may also be used for heating the micropreconcentrator during desorption since hydrides can be stored at the equivalent of 1000 w-hr/L and the hydrogen can act as a carrier and then be reused to provide heat. Other techniques known in the art for desorption may also be employed.

Other embodiments of micropreconcentrators that may incorporate the use of MOFs and/or MEMS valves and micropost arrays according to the principles of the invention include a dosimeter, which is any device used to measure an individual's exposure to a hazardous environment and is often portable. Examples include the dosimeters described in U.S. Pat. Nos. 4,235,097, 4,040,085, 3,985,017, 6,607,700, 5,482, 677, 5,110,551 and U.S. Patent Application No. 2005/0101027. In addition, the preconcentrators may be in disc or pellet form as described in U.S. Pat. Nos. 3,925,022, 4,301, 114, 5,014,541, and 6,978,657, for example. Additional examples of preconcentrators that may use the principles of the invention are given in U.S. Pat. Nos. 3,168,823, 3,345, 858, 3,357,232, 3,568,411, 3,585,863, 3,769,837, 3,797,318, 3,807,217, 3,897,679, 3,923,461, 3,950,980, 4,084,440, 4,128,008, 4,180,389, 4,293,316, 4,399,688, 4,451,816, 4,541,268, 4,599,095, 4,698,071, 4,701,306, 4,759,210, 4,805,441, 4,819,477, 4,915,051, 4,915,843, 4,977,095, 5,083,010, 5,092,155, 5,092,218, 5,123,276, 5,142,143, 5,162,652, 5,173,264, 5,224,972, 5,288,310, 5,294,418, 5,328,851, 5,395,589, 5,465,607, 5,551,278, 5,585,575, 5,753,832, 5,763,360, 5,795,368, 5,854,431, 5,970,804, 6,085,601, 6,165,254, 6,223,584, 6,345,545, 6,455,003, 6,523,393, 6,604,406, 6,610,125, 6,656,738, 6,814,781, 6,910,394, 6,984,524, RE38,797, 6,749,826, 5,465,607, 5,092,217, 6,848,325.

Yet, further embodiments of the micropreconcentration systems of the invention may be designed to detect substances using an integrated cartridge that is attached to a handheld vacuum-like device, such as for non-contact gas sampling of explosives. The handheld vacuum may draw sample particles and other molecules off of a person or object and trap them on a filter that contains special sorbents, such as MOFs. These sorbents catch and grab the sample particles and molecules out of the air. The filter may then be manually transferred to a commercial off-the-shelf ion mobility spectrometer (COTS IMS) based detector for analysis. Examples of possible substances that may be detected by a COTS IMS may include, but are not limited to dimethyl dinitrobutane (DMNB), triperoxides, TATP and HMTD.

Although the various micropreconcentrator embodiments have been described for use in a gas chromatograph, micropreconcentrators of the invention may also be used in a number of different detection devices, including, but not limited to a surface acoustic wave (SAW), an evanescent wave detector, a piezoelectric detector, an ion mobility spectrometer, and a chemiresistor detector. Examples of these devices are given in U.S. Pat. Nos. 3,168,823, 3,345,858, 3,357,232, 3,568,411, 3,585,863, 3,769,837, 3,797,318, 3,807,217, 3,897,679, 3,923,461, 3,950,980, 4,084,440, 4,128,008, 4,180,389, 4,293,316, 4,399,688, 4,451,816, 4,541,268, 4,599,095, 4,698,071, 4,701,306, 4,759,210, 4,805,441, 4,819,477, 4,915,051, 4,915,843, 4,977,095, 5,083,019, 5,092,155, 5,092,218, 5,123,276, 5,142,143, 5,162,652, 5,173,264, 5,224,972, 5,288,310, 5,294,418, 5,328,851, 5,395,589, 5,465,607, 5,551,278, 5,585,575, 5,753,832, 5,763,360, 5,795,368, 5,854,431, 5,970,804, 6,085,601, 6,165,254, 6,223,584, 6,345,545, 6,455,003, 6,523,393, 6,604,406, 6,610,125, 6,656,738, 6,814,781, 6,910,394, 3,925,022, 4,301,114, 5,014,541, 6,978,657, RE38,797. 6,967,193, 6,840,120, and 6,773,674.

The micropreconcentrators of the invention may be used with detection devices for a variety of applications, including, but not limited to air quality, water quality, pollution monitoring, process monitoring, breath analysis, personal health monitoring and protection, food monitoring, and security. These security applications include passenger screening in schools, airports, subways, train stations, buses, shipping containers/truck screening, building security, first responder sensors, sensors for water and food safety, and the military.

While the invention has been described in terms of exemplary embodiments, those skilled in the art will recognize that the invention can be practiced with modifications in the spirit and scope of the appended claims. These examples given above are merely illustrative and are not meant to be an exhaustive list of all possible designs, embodiments, applications or modifications of the invention.

What is claimed:

1. A method of using a metal organic framework ("MOF") as a sorbent of an analyte in a preconcentrator or micropreconcentrator having a microelectromechanical ("MEMS") valve system with at least three (3) valves in the preconcentrator or micropreconcentrator, said method comprising the steps of:
    a) concentrating an analyte by sorbing it on a MOF highly selective to the analyte;
    b) desorbing the analyte from the MOF; and
    c) conducting the desorbed analyte to a device for analysis.

2. The method of claim 1, wherein one of the preconcentrator or micropreconcentrator is a purge and trap system, personal respirator, array of microstructures, dosimeter, disc, pellet, or swab.

3. The method of claim 1, wherein the MEMS valve system has 4 or 5 valves.

4. The method of claim 1, wherein the MOF has a thermal stability of up to about 300° C. to about 400° C.

5. The method of claim 1, wherein the MOF sorbs substantially all of the analyte.

6. The method of claim 1, wherein after sorbing the analyte, the MOF releases the analyte.

7. The method of claim 6, wherein the MOF releases the analyte by thermal desorption.

8. The method of claim 1, wherein the MOF comprises particles or a film.

9. The method of claim 8, wherein the MOF particles have a diameter of between about 20 nanometers to about 500 microns.

10. The method of claim 9, wherein the MOF particles have a diameter of between about 100 nanometers to about 50 microns.

11. The method of claim 1, wherein the MOF comprises one or more materials selected from the group consisting of Zn-MOF1, Zn-MOF2, Zn-MOF3, Zn-MOF4, Zn-MOF5, Cu-MOF1, Cu-MOF2, Tb-MOF1, Tb-MOF2, Cd-MOF1, Cd-MOF2, Cd-MOF3, CoMOF1, Co-MOF2, Zn-MOF6, MOF-5, $Cu(4,4'-bpy)_{1.5}NO_3(H_2O)_{1.25}$, IRMOF2, $[Cu_3(TMA)_2]_n$, $[Cu(OH)—(C_5H_4NCO_2)]$, MOF-38, $Ag(4,4'-bpy)NO_3$, IRMOF3 and IRMOF7.

12. The method of claim 1, wherein the MOF is selective to a predetermined analyte or group of analytes.

13. The method of claim 1, wherein the MOF sorbs analytes selected from the group consisting of explosives and chemical warfare agents.

14. The method of claim 1, wherein the MOF sorbs analytes selected from the group consisting of XV, sarin, DMMP, PMP, diethyl methylphosphonate (DEMP), diisopropyl methylphophonate (DIMP), dichlorohexane, malathion, acetic anhydride, TNT, and RDX.

15. A system for collecting an analyte from a sample comprising a preconcentrator or micropreconcentrator including:
    a) an inlet to receive the sample;
    b) a collection chamber containing a sorbent comprising a metal organic framework ("MOF"); and
    c) a microelectromechanical ("MEMS") valve system in the preconcentrator or micropreconcentrator having at least three (3) valves to control the flow of the sample through the system.

16. The system of claim 15, wherein said MEMS valve system has 4 or 5 valves.

17. The system of claim 15, wherein the MEMS valve system can be positioned in at least a first position, a second position, and a third position, wherein:
    when the MEMS valve system is positioned in the first position, the collection chamber containing the MOF is exposed to a carrier gas optionally comprising an analyte,
    when the MEMS valve system is positioned in the second position, the collection chamber containing the MOF is coupled to a means for desorption of analyte present on the MOF, and
    when the MEMS valve system is positioned in the third position, the collection chamber containing the MOF can be exposed to a purge gas.

18. The system of claim 15, wherein the MOF has a thermal stability of up to about 300° C. to about 400° C.

19. The system of claim 15, wherein the MOF comprises particles or a film.

20. The system of claim 15, wherein the MOF particles have a diameter of between about 20 nanometers to about 500 microns.

21. The system of claim 20, wherein the MOF particles have a diameter of between about 100 nanometers to about 50 microns.

22. The system of claim 15, wherein the MOF comprises one or more materials selected from the group consisting of Zn-MOF1, Zn-MOF2, Zn-MOF3, Zn-MOF4, Zn-MOF5, Cu-MOF1, Cu-MOF2, Tb-MOF1, Tb-MOF2, Cd-MOF1, Cd-MOF2, Cd-MOF3, CoMOF1, Co-MOF2, Zn-MOF6, MOF-5, $Cu(4,4'-bpy)_{1.5}NO_3(H_2O)_{1.25}$, IRMOF2, $[Cu_3(TMA)_2]_n$, $[Cu(OH)—(C_5H_4NCO_2)]$, MOF-38, $Ag(4,4'-bpy)NO_3$, IRMOF3 and IRMOF7.

23. The system of claim 15, wherein the MOF sorbs analytes selected from the group consisting of explosives and chemical warfare agents.

24. The system of claim 15, wherein the MOF sorbs analytes selected from the group consisting of XV, sarin, DMMP, PMP, diethyl methylphosphonate (DEMP), diisopropyl methylphophonate (DIMP), dichlorohexane, malathion, acetic anhydride, TNT, and RDX.

* * * * *

UNITED STATES PATENT AND TRADEMARK OFFICE
CERTIFICATE OF CORRECTION

| | | |
|---|---|---|
| PATENT NO. | : 8,123,834 B2 | |
| APPLICATION NO. | : 11/539405 | |
| DATED | : February 28, 2012 | |
| INVENTOR(S) | : Masel et al. | |

It is certified that error appears in the above-identified patent and that said Letters Patent is hereby corrected as shown below:

--In the specification, right before "Background of the Invention" please delete "The U.S. government may have certain rights in the invention." and insert --The U.S. government has certain rights in the invention.--

Signed and Sealed this
Fifteenth Day of May, 2012

David J. Kappos
*Director of the United States Patent and Trademark Office*